(12) United States Patent
Shepherd et al.

(10) Patent No.: US 11,701,245 B2
(45) Date of Patent: Jul. 18, 2023

(54) ELECTROHYDRAULIC BATTERIES AND DEVICES AND SYSTEMS INCLUDING SAME

(71) Applicant: Cornell University, Ithaca, NY (US)

(72) Inventors: Robert F. Shepherd, Ithaca, NY (US); James Pikul, Philadelphia, PA (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 17/605,996

(22) PCT Filed: Apr. 23, 2020

(86) PCT No.: PCT/US2020/029668
§ 371 (c)(1),
(2) Date: Oct. 22, 2021

(87) PCT Pub. No.: WO2020/219780
PCT Pub. Date: Oct. 29, 2020

(65) Prior Publication Data
US 2022/0218500 A1    Jul. 14, 2022

Related U.S. Application Data

(60) Provisional application No. 62/837,710, filed on Apr. 23, 2019.

(51) Int. Cl.
*A61H 3/00* (2006.01)
*H01M 8/18* (2006.01)
(Continued)

(52) U.S. Cl.
CPC .............. *A61F 2/74* (2021.08); *A61F 2/586* (2013.01); *A61H 1/0288* (2013.01); *A61H 3/00* (2013.01);
(Continued)

(58) Field of Classification Search
CPC .......... A61H 1/0288; A61H 3/00; A61F 2/74; A61F 2/586; H01M 8/00; H01M 8/04186
(Continued)

(56) References Cited

U.S. PATENT DOCUMENTS 4,710,438 A   12/1987 Leben et al.
5,506,065 A   4/1996 Tribioli et al.
(Continued)

FOREIGN PATENT DOCUMENTS

EP      0307292 B1    9/1992

OTHER PUBLICATIONS

Katzschmann, Robert et al, Hydraulic Autonomous Soft Robotic Fish for 3D Swimming (Year: 2014).*
(Continued)

*Primary Examiner* — Timothy A Stanis
(74) *Attorney, Agent, or Firm* — Barnes & Thornburg LLP

(57) ABSTRACT

The present disclosure provides an electrohydraulic device. The device includes a battery having a vessel containing a flowable electrolyte. The battery may be a flow cell battery, such as, for example, a redox flow cell battery. In a flow cell battery, the flowable electrolyte may a catholyte and/or an anolyte. An actuator is in fluidic communication with the vessel of the battery. The actuator is configured to be actuated using the flowable electrolyte. A cation exchange membrane may separate the vessel into an anolyte side and a catholyte side. The actuator may be in fluidic communication with either side (anolyte side or catholyte side) of the vessel.

17 Claims, 41 Drawing Sheets

(51) Int. Cl.
  *H01M 8/04186* (2016.01)
  *A61F 2/74* (2006.01)
  *A61F 2/58* (2006.01)
  *A61H 1/02* (2006.01)

(52) U.S. Cl.
  CPC ....... *H01M 8/04186* (2013.01); *H01M 8/188* (2013.01); *A61H 2201/1238* (2013.01)

(58) Field of Classification Search
  USPC .......................................................... 429/8
  See application file for complete search history.

(56) References Cited

U.S. PATENT DOCUMENTS

| | | | |
|---|---|---|---|
| 5,532,079 A | 7/1996 | Tribioli et al. | |
| 2006/0102455 A1* | 5/2006 | Chiang | H01M 50/443 429/231.9 |
| 2009/0021106 A1* | 1/2009 | Baughman | H02N 11/006 60/527 |
| 2014/0004437 A1* | 1/2014 | Slocum | H01M 8/04201 429/443 |
| 2014/0057141 A1* | 2/2014 | Mosso | H01M 8/188 429/51 |
| 2014/0208731 A1* | 7/2014 | Shepherd | B25J 9/1075 60/407 |
| 2016/0218375 A1* | 7/2016 | Chiang | H01M 8/0215 |

OTHER PUBLICATIONS

Xu, Yao et al, Electrically Acutated Soft Acuator Integrated With an Electrochemical Reactor, Extreme Mechanics Letters (Year: 2022).*
Marchese, Andrew et al, A Recipe for Soft Fluidic Elastomer Robots, Soft Robotics, vol. 2, No. 1, p. 7-25 (Year: 2015).*

* cited by examiner $Zn \leftrightarrow Zn^{2+} + 2e^-$  $E^0 = -0.7626$ V vs SHE
$I_3^- + 2e^- \leftrightarrow 3I^-$  $E^0 = +0.5360$ V vs SHE

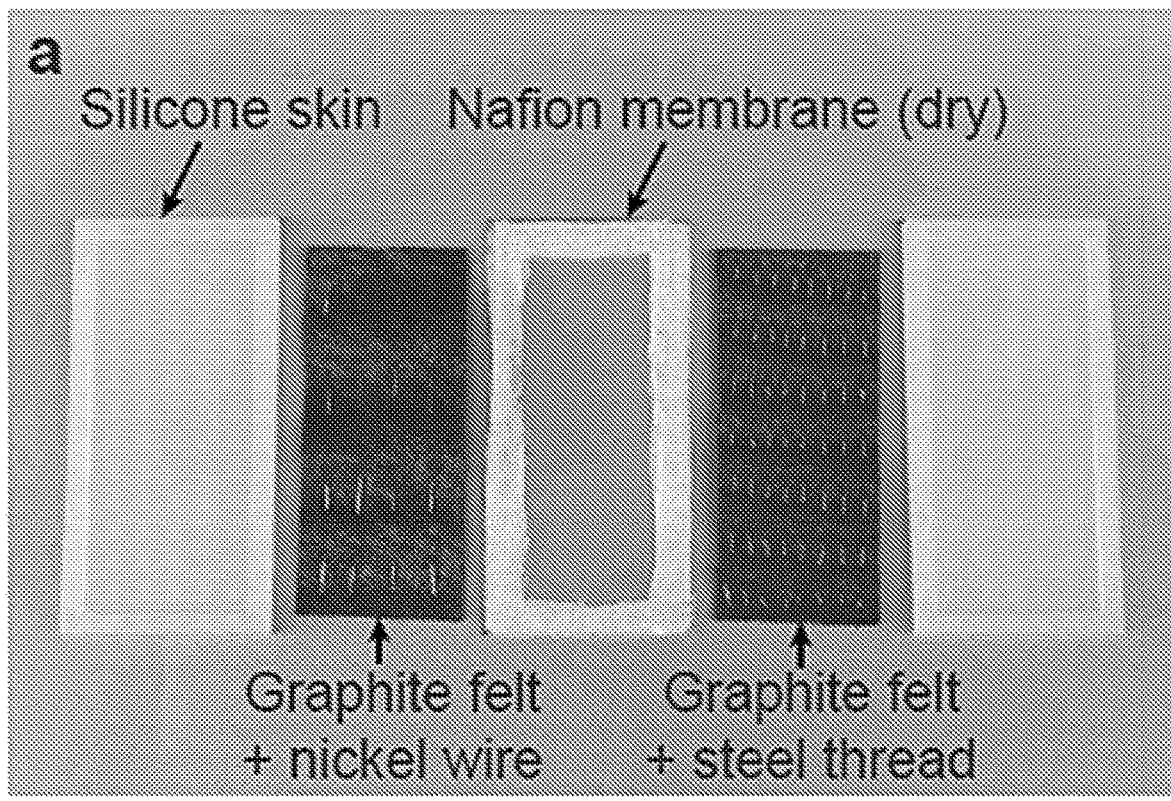
Fig. 4A
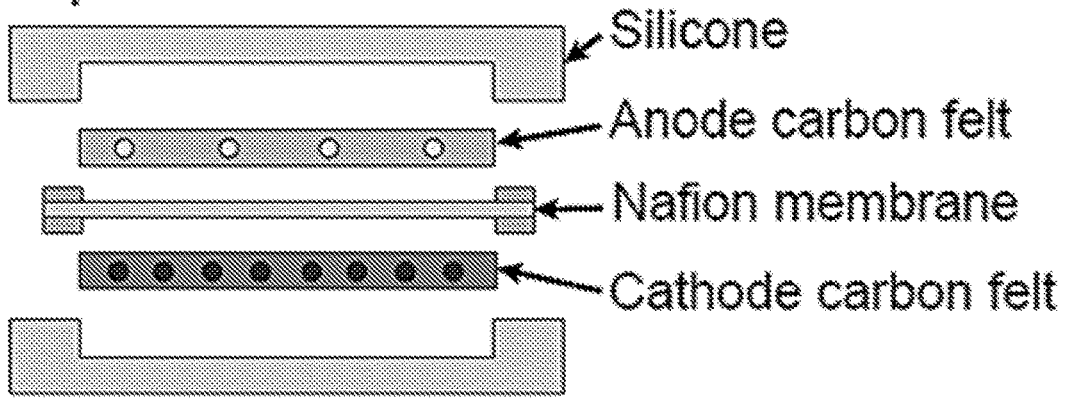
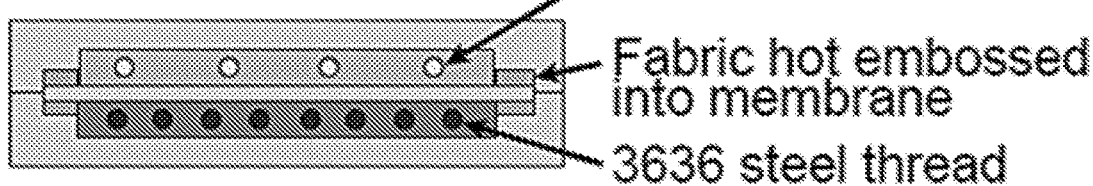
Fig. 4B

Pelvic Fin Battery Cell

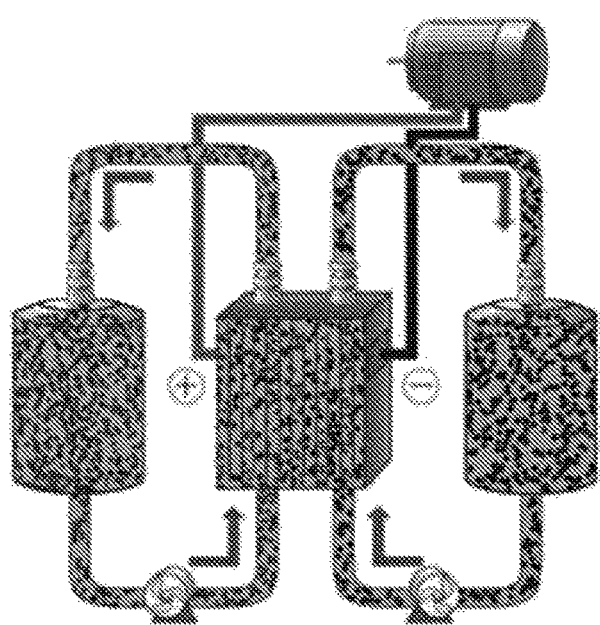 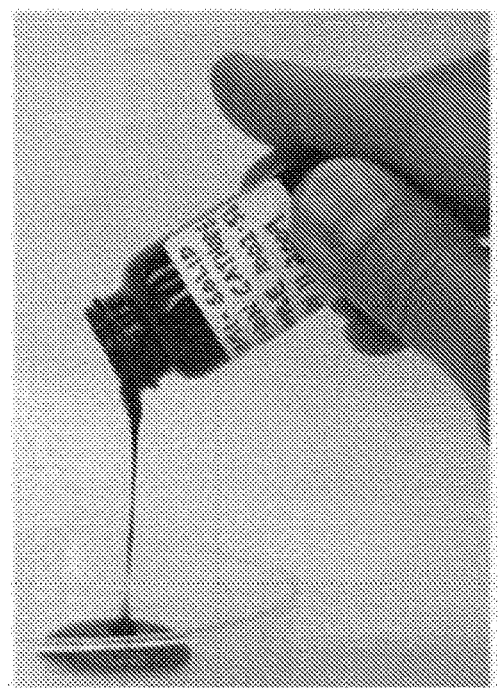
Fig. 11A　　　　　　　　Fig. 11B
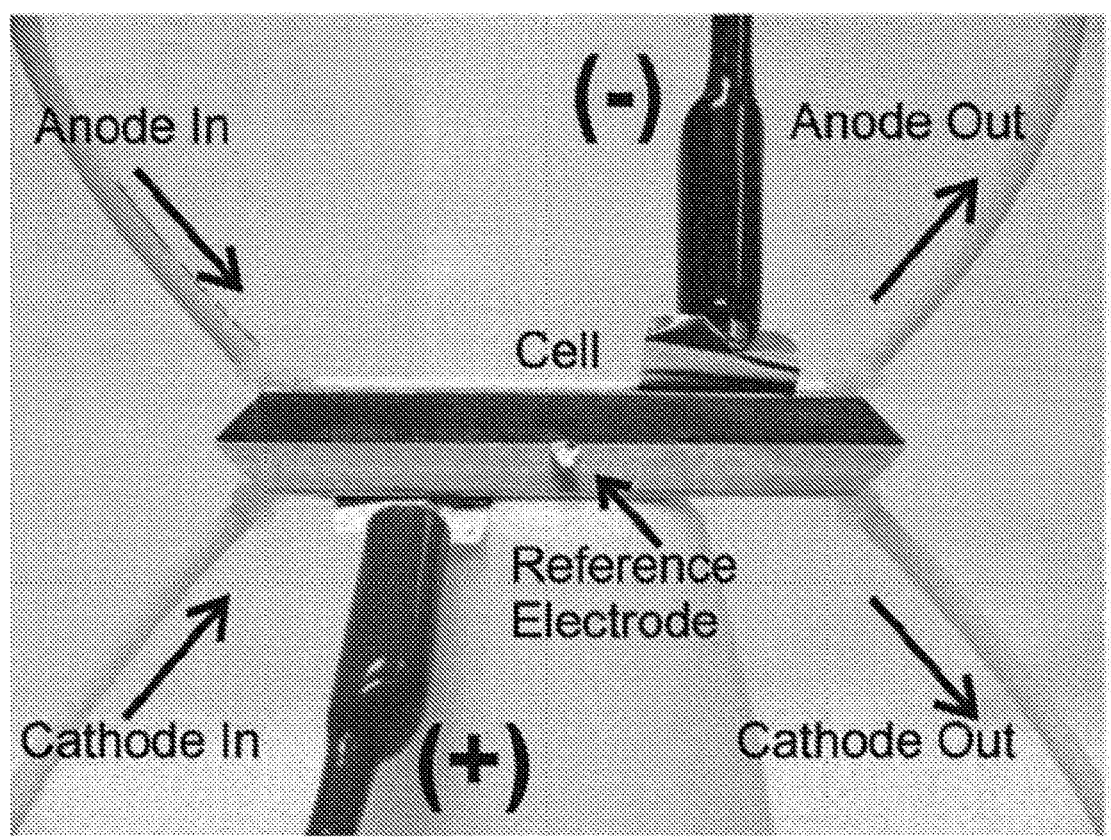
Fig. 11C

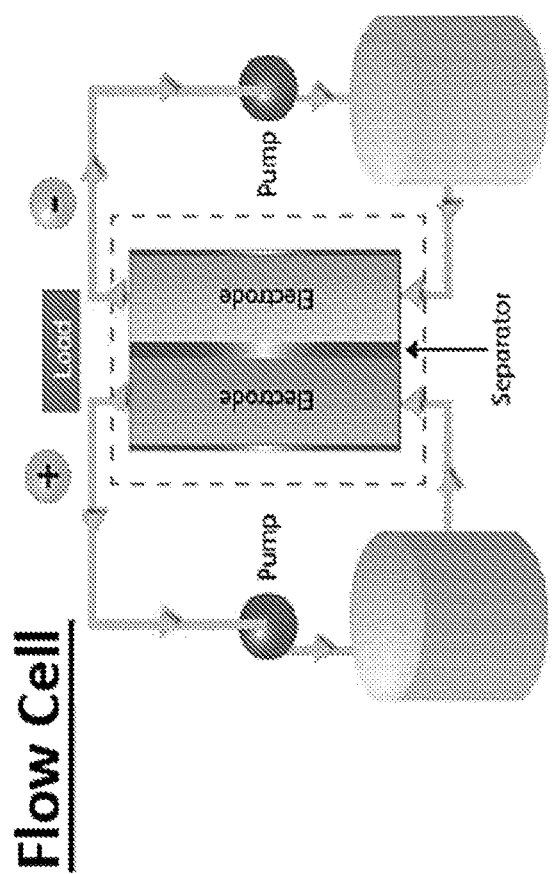
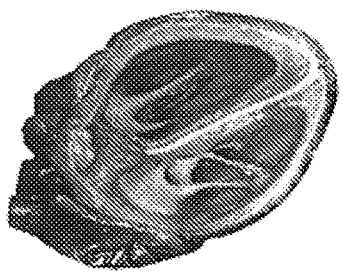
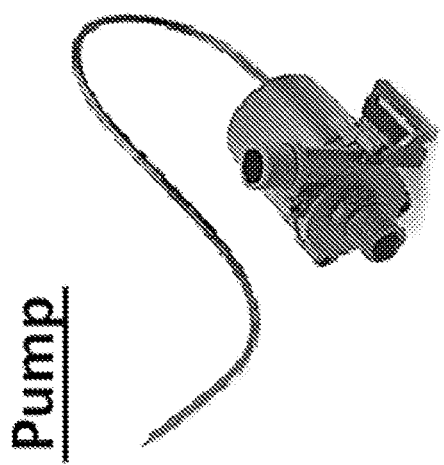
Fig. 15A

Table 1.

| Selected muscles | Image | Function |
|---|---|---|
| Trapezius (Lower) | | Stabilize the *adduction* and rotation of the scapula |
| Deltoideus Medialis | | Perform **abduction* of shoulder joint |
| Pectoralis Major (Upper) | | Perform flexion and medial rotation of the shoulder joint |
| Subscapularis (Ventral surface) | | Perform medial rotation of the shoulder joint |
| Bicep Brachii Long Head | | Perform flexion of the arm at the elbow joint and supination of the forearm |
| Bicep Brachii Short Head | | Assists with shoulder adduction |
| Triceps Brachii Long Head | | Perform extension of the elbow joint. Assists in adduction and extension of the shoulder joint |
| Flexor Carpi Radialis | | Perform flexion of the wrist |
| Brachioradialis | | Perform flexion of the elbow |
| Abductor Pollicis Brevis | | Perform abduction of fingers |
| Flexor Digiti Minimi Brevis | | Perform flexion of fingers |

Fig. 22

Table 2. Definitions of states

| State | Inflating valve | Deflating valve | Comment |
|---|---|---|---|
| 1 | Off | Off | Target region |
| 2 | On for 1 period, then Off for X period | Off | Small positive error |
| 3 | Off | On for 1 period, then Off for Y periods | Small negative error |
| 4 | On | Off | Large positive error |
| 5 | Off | On | Large negative error |

Fig. 24

ELECTROHYDRAULIC BATTERIES AND DEVICES AND SYSTEMS INCLUDING SAME

CROSS-REFERENCE TO RELATED APPLICATIONS

This application claims priority to U.S. Provisional Application No. 62/837,710, filed on Apr. 23, 2019, now pending, the disclosure of which is incorporated herein by reference.

STATEMENT REGARDING FEDERALLY SPONSORED RESEARCH

This invention was made with government support under contract no. N00014-17-1-2837 awarded by the Office of Naval Research (ONR). The government has certain rights in the invention.

FIELD OF THE DISCLOSURE

The present disclosure relates to batteries, and in particular flow cell batteries.

BACKGROUND OF THE DISCLOSURE

Modern robots suffer from lackluster efficiency and autonomy. Energy storage systems are among the most visible limitations of robotic systems, adding to their size and weight. Wearable robotic systems provide muscle augmentation for individuals, but current systems are generally cumbersome, inhibit the wearer's flexibility, and suffer from inadequate battery life.

BRIEF SUMMARY OF THE DISCLOSURE

Here we present an electrohydraulic device that enables a new combination of functions in a mobile robot: hydraulic force transmission, actuation, and energy storage for a geometric increase in system energy density. The ability to store chemical potential in a liquid circulatory system is a direct analogy to the oxygen rich blood we use in our metabolism to power muscle contraction. This use of electrochemical energy storage in hydraulic fluids could facilitate increased energy density, autonomy, efficiency, and multifunctionality in robot designs.

In some embodiments, the present disclosure provides an electrohydraulic device. The device includes a battery having a vessel containing a flowable electrolyte. The battery may be a flow cell battery, such as, for example, a redox flow cell battery. In a flow cell battery, the flowable electrolyte may a catholyte and/or an anolyte. An actuator is in fluidic communication with the vessel of the battery. The actuator is configured to be actuated using the flowable electrolyte. A cation exchange membrane may separate the vessel into an anolyte side and a catholyte side. The actuator may be in fluidic communication with either side (anolyte side or catholyte side) of the vessel.

In some embodiments, the actuator has a hydraulic chamber configured to be pressurized by the flowable electrolyte. The actuator may be a soft actuator configured to be inflated and/or deflated by the flowable electrolyte. The soft actuator comprises polyurethane or a styrene-butadiene compound. The actuator may be a linear actuator. The actuator may comprise an impeller configured to be rotated by a flow of the flowable electrolyte. In some embodiments, the actuator makes up at least a portion of the vessel.

In some embodiments, the electrohydraulic device includes a pump for selectively pressurizing or depressurizing the actuator with flowable electrolyte. In some embodiments, the electrohydraulic device includes a heat exchanger in fluid communication with the battery, wherein the flowable electrolyte is cooled by passage through the heat exchanger. The electrohydraulic device may include a sensor configured to detect movement of the actuator.

In some embodiments, the present disclosure may be embodied as a muscle augmentation system, such as, for example, an exoskeleton (exosuit), or a partial exoskeleton, prosthetic, etc. The muscle augmentation system includes at least one electrohydraulic device according to any of the embodiments herein. The muscle augmentation system may include a poroelastic skin configured to be selectively expanded or collapsed for thermal management.

The present disclosure may be embodied as a method making an electrohydraulic battery. The method includes providing a battery having a vessel for containing a flowable electrolyte; and providing an actuator in fluidic communication with the vessel, wherein the actuator is configured to be actuated using the flowable electrolyte. The method may include filling the vessel with a flowable electrolyte.

DESCRIPTION OF THE DRAWINGS

For a fuller understanding of the nature and objects of the disclosure, reference should be made to the following detailed description taken in conjunction with the accompanying drawings.

FIG. 4A: A photograph of the components of a composite cell testing blank.

FIG. 4B: Cross-sectional diagrams of the assembled testing blank.

FIG. 11A: A diagram of a semi-solid flow cell (SSFC) battery configuration.

FIG. 11B: A photograph depicting liquid properties of an exemplary catholyte-cathode suspension.

FIG. 11C: A photograph showing a simple configuration of SSFC battery.

FIG. 15A: Schematic of pump analogy to a heart pump and flow cell battery that would also function as the hydraulic fluid, pump motors, and electrochemical storage.

FIG. 22: Table describing exemplary placements of sensor channels corresponding to specific movements of an exemplary exosuit.

FIG. 24: State table for the exemplary state machine of FIG. 23.

DETAILED DESCRIPTION OF THE DISCLOSURE

Although subject matter of the present disclosure is described in terms of certain embodiments and examples, other embodiments and examples, including embodiments and examples that do not provide all of the benefits and features set forth herein, are also within the scope of this disclosure. For example, various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

The steps of the method described in the various embodiments and examples disclosed herein are sufficient to produce a fabric of the present disclosure. Thus, in an embodiment, a method consists essentially of a combination of the steps of the methods disclosed herein. In another embodiment, a method consists of such steps.

The present disclosure provides electrohydraulic batteries and electrohydraulic devices. The present disclosure also provides method of making and uses of same.

In a first aspect, the present disclosure may be embodied as an electrohydraulic device 10. The device 10 includes a battery 12 having a flowable electrolyte 16. In some embodiments, the battery may be a flow battery, such as, for example, a redox flow battery. In some embodiments, the battery may be a hybrid flow battery, such as, for example, a hybrid redox flow battery. Other batteries having flowable electrolytes may be used. By flowable, it is intended that the electrolyte is a liquid, gel, semi-solid, or any other material that is capable of use as a hydraulic working fluid (e.g., aqueous, non-aqueous, etc.)

Figure 1:
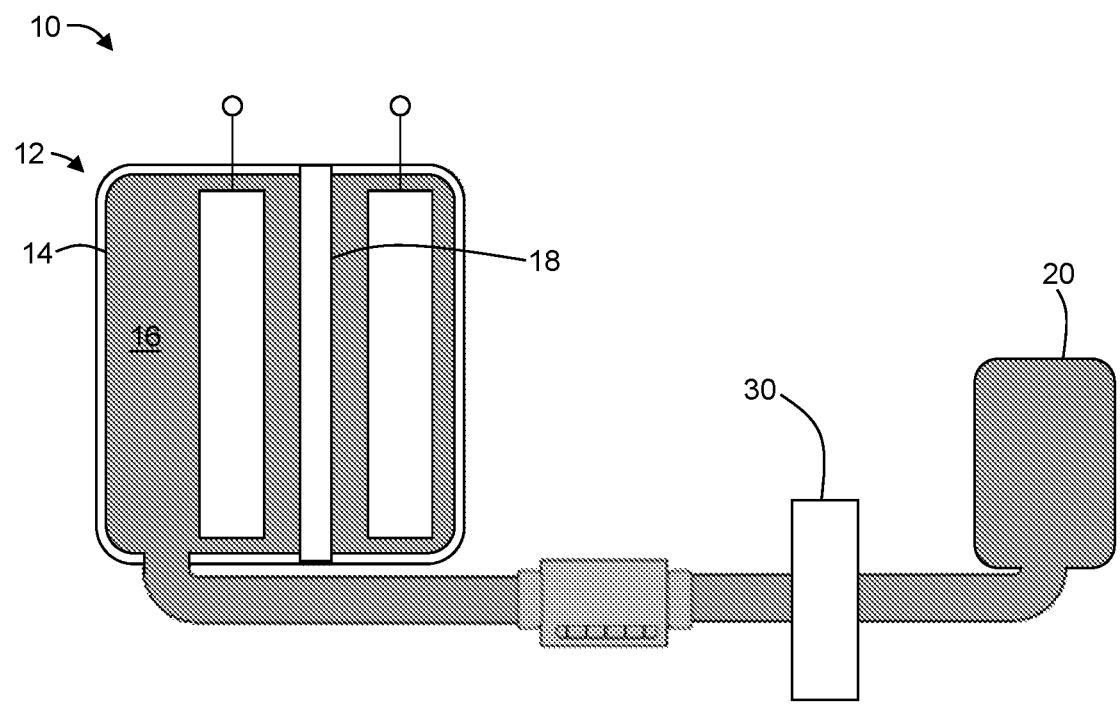
FIG. 1: A diagram of a electrohydraulic device according to an embodiment of the present disclosure.

The battery 12 includes a vessel 14 configured to contain the flowable electrolyte 16. The device also includes an actuator 20 in fluidic communication with the vessel 14 of the battery 12. In some embodiments, such as that depicted in FIG. 1, the actuator may be physically apart from the vessel—e.g., in fluidic communication via, for example, a tube or similar fluidic channel. In some embodiments, such as that depicted in FIGS. 2B and 3A, the actuator makes up a portion of the vessel itself and is in fluidic communication as a result of making up a portion of the vessel. For example, the actuator may be a soft actuator (e.g., an elastomeric material, etc.) and make up a wall of a walled vessel. In another example, the vessel is a chamber in which the actuator (e.g., in the form of a piston) is able to move. The vessel may be made from rigid and/or non-rigid (e.g., soft) materials. For example, the vessel may be made from metals, plastics, glass, composites, elastomers, or combinations of these and/or other materials.

The vessel 14 may include a cation exchange membrane 18 separating an anolyte side of the vessel from a catholyte side of the vessel. The actuator may be in fluidic communication with the catholyte side or the anolyte side, depending on the application.

Redox flow batteries (RFBs) are a potential candidate for this application. RFBs utilize flowable liquid or semi-solid components and are known for their fast response times, safety, and design flexibility. RFBs also have lower energy and power densities relative to lithium-ion batteries. Their use has historically been limited to large-scale stationary applications where cost and scalability are more important than portability and form factor. Examples of suitable flow cell batteries include zinc-iodide batteries, vanadium batteries, and the like. The electrolyte may comprise a suspension of an active lithium ion compound (e.g., $LiCoO_2$—$Li_4Ti_5O_{12}$, $LiCoO_2$-graphite, etc.), a suspension of vanadium (HI) salt (e.g., vanadium (III) chloride, etc.), a suspension of iron (III) salt (e.g., iron (III) chloride, etc.), or the like.

In an exemplary hybrid RFB suitable for use in the present device, energy is stored between a redox couple of solid zinc in the anode and highly soluble (theoretically, up to 7.0 M) triiodide in the aqueous catholyte. The zinc is oxidized during discharge, releasing electrons and soluble zinc ions. The electrons flow through external circuits powering one or more loads. The zinc ions simultaneously flow through an electrolyte and a cation exchange membrane to the catholyte where they balance the charge as triiodide is reduced to iodide. The catholyte is able to circulate so as to replenish the local concentration of $I_3^-/I^-$, which maintains a constant power density during cycling. The combination of a solid anode and highly soluble catholyte enables a high theoretical energy density (I'~322 Wh $L^{-1}$), about half that of a Tesla model S lithium ion battery (I'=676 Wh $L^{-1}$).

The actuator may comprise a hydraulic chamber configured to be pressurized by the flowable electrolyte. For example, the flowable electrolyte may be pumped into the hydraulic chamber so as to actuate the actuator. In some embodiments, the actuator is a soft actuator—having at least one soft member able to stretch (e.g., thereby expanding a hydraulic chamber) when pressurized by the flowable electrolyte and able to contract when the pressure of flowable electrolyte is reduced. Such a soft actuator may inflate and deflate according to the pressure of the flowable electrolyte within the actuator. The soft actuator may be made from any suitable material including, for example, rubbers such as polyurethane, styrene-butadine compounds, silicone, latex, pleated plastic films such as polyethylene, polystyrene, polypropylene, etc.

In some embodiments, the actuator makes up at least a portion of the vessel. For example, the actuator may make up a wall of a walled vessel. In a particular example, the actuator may be a soft actuator and able to actuate by stretching with as increase in pressure of the flowable electrolyte within the vessel. In another example, the vessel may be configured as a piston chamber with the piston as the actuator. As pressure within the vessel increases (for example, due to an inflow of flowable electrolyte), the piston is urged to move (actuated) in order to increase the volume of chamber.

The device 10 may further comprise a heat exchanger 30 for heating and/or cooling the flowable electrolyte. For example, a heat exchanger can be incorporated so as to cool the flowable electrolyte using the ambient environment (e.g., air in a land-based application, water in an underwater application, etc.)

In some embodiments, the actuator is a linear actuator. For example, the actuator may be a hydraulic piston as is known in the art. In other embodiments, the actuator may be an impeller configured to be rotated by a flow of the flowable electrolyte. The actuator may be made from rigid and/or non-rigid materials. For example, the actuator may be made from metals, plastics, glass, composites, elastomers, or combinations of these and/or other materials.

In an aspect further discussed below under the heading "Example 2," the present disclosure may be embodied as a muscle augmentation system. For example, the muscle augmentation system may be an exo-skeleton (i.e., exosuit), prosthetic limb, etc. An exo-skeleton may be a full-body suit or a partial body system (e.g., a system wearable to supplement strength in one or both arms, lower body, back, etc.) The muscle augmentation system comprises at least one electrohydraulic device according to any embodiment provided herein. In some embodiments, the muscle augmentation system includes a poroelastic skin configured to be selectively expanded or collapsed for thermal management. For example, a system for use as a dive suit may include a poroelastic skin to provide insulative properties while underwater. Additional details are provided in Example 2 below.

Flow Cell Batteries

Unlike the more familiar lithium-polymer (LiPo) batteries with high energy density (~2 MJ $L^{-1}$), redox flow batteries typically have lower energy densities (~0.2 MJ $L^{-1}$) but are much less costly and have other benefits such as rapid charging by switching out the discharged, liquid anolyte and catholyte. Recently, semi-solid flow cells (SSFCs) using suspensions of lithium oxides (e.g., $LiCoO_2$—$Li_4Ti_5O_{12}$ and $LiCoO_2$-graphite) with networks of percolated carbon electrodes show volumetric energy densities of ~2 MJ $L^{-1}$ approaching that of solid state LiPo batteries.

Figure 11D:
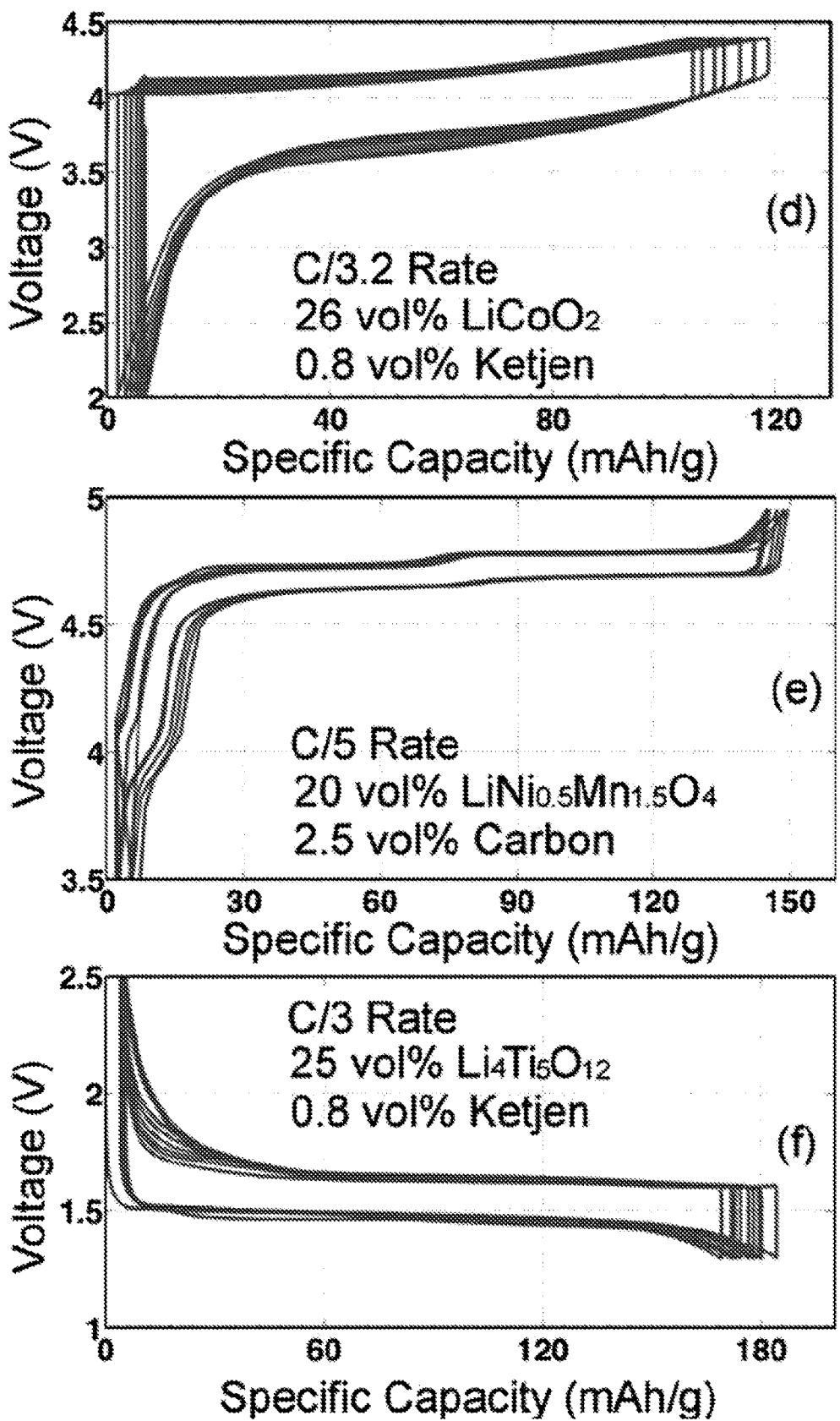
FIG. 11D: Graphs showing relatively high voltages possible in an exemplary SSFC half cell.

The benefit of SSFCs to for example, robotics and exoskeletons, beyond the low cost and rapid battery recharge ability, is the ability of the material to flow under a pressure gradient (FIGS. 11A-11C). FIG. 11D also demonstrates the relatively high voltages possible in SSFC half cells. Research in this space involves increasing the loading of electroactive solids into the anolyte and catholyte suspension while maintaining flowable rheology. To this end, biphasic suspensions are being pursued for semi-solid electrode networks and there is an opportunity for polydisperse particles to drive the solids loading beyond 40 volume % while still maintaining the ability to flow in a hydraulic system.

Example 1

Electrolytic Vascular Systems for Energy Dense Robots

Modern robots lack the multifunctional, interconnected systems found in living organisms and, consequently, exhibit reduced efficiency and autonomy. Energy storage systems are among the most visible limitations to robot autonomy, but their size, weight, material, and design constraints can be reexamined in the context of multifunctional, bio-inspired applications. Here we present a synthetic, energy-dense circulatory system embedded in an untethered, aquatic soft robot. Modeled after redox flow batteries, this vascular system combines the functions of hydraulic force transmission, actuation, and energy storage into a single integrated design that geometrically increases the energy density of the robot to enable long duration operation. The fabrication techniques and compliant materials used in its construction also allow the vascular system to be shaped into complex form factors that bend and deform with robot movement. This use of electrochemical energy storage in hydraulic fluids could facilitate increased energy density, autonomy, efficiency, and multifunctionality in future robot designs.

Animals are composed of multifunctional, biological systems that allow them to grow, extract and store energy from their environment, and respond to sensory input. The human circulatory system is an excellent example of this multifunctionality. In addition to transporting oxygen and nutrients throughout the body, the circulatory system also removes waste products, regulates internal temperature and cellular pH levels, and assists in fighting off diseases and infection. Furthermore, the network of blood vessels comprising the circulatory system is deeply intertwined with muscles, bones, and other organ systems. Robots, in contrast, are typically composed of isolated power, actuation, sensory, and control systems, each optimized for specific tasks. The clear gaps in mobility, adaptability, and efficiency between robots and animals motivate tighter integration between these fundamental functional components via bioinspired design.

Energy storage is one of the most significant barriers to achieving long-duration autonomy in robots. Typically, a block of material serves a singular function as a robot's storage battery, which results in sub-linear scaling of system energy density with total energy—added battery packs increase weight and necessitate additional modifications to maintain overall performance. These size, weight, and power tradeoffs can be re-evaluated when multifunctionality is considered. Some examples of batteries serving multiple functions are (i) heavy lead-acid batteries used for weight balancing in forklifts (ii) flexible batteries that function as flapping wing surfaces, and (iii) structural batteries that simultaneously act as load bearing members and energy storage elements in satellites and unmanned aerial vehicles. We have identified hydraulic fluids, used as force transmission and actuating media in the machinery of robots, as another area of opportunity for multifunctional energy storage.

Redox flow batteries (RFBs) are a potential candidate for this application. RFBs utilize flowable liquid or semi-solid components and are known for their fast response times, safety, and design flexibility. RFBs also have lower energy and power densities relative to lithium-ion batteries. Their use has historically been limited to large-scale stationary applications where cost and scalability are more important than portability and form factor.

Figure 2A:
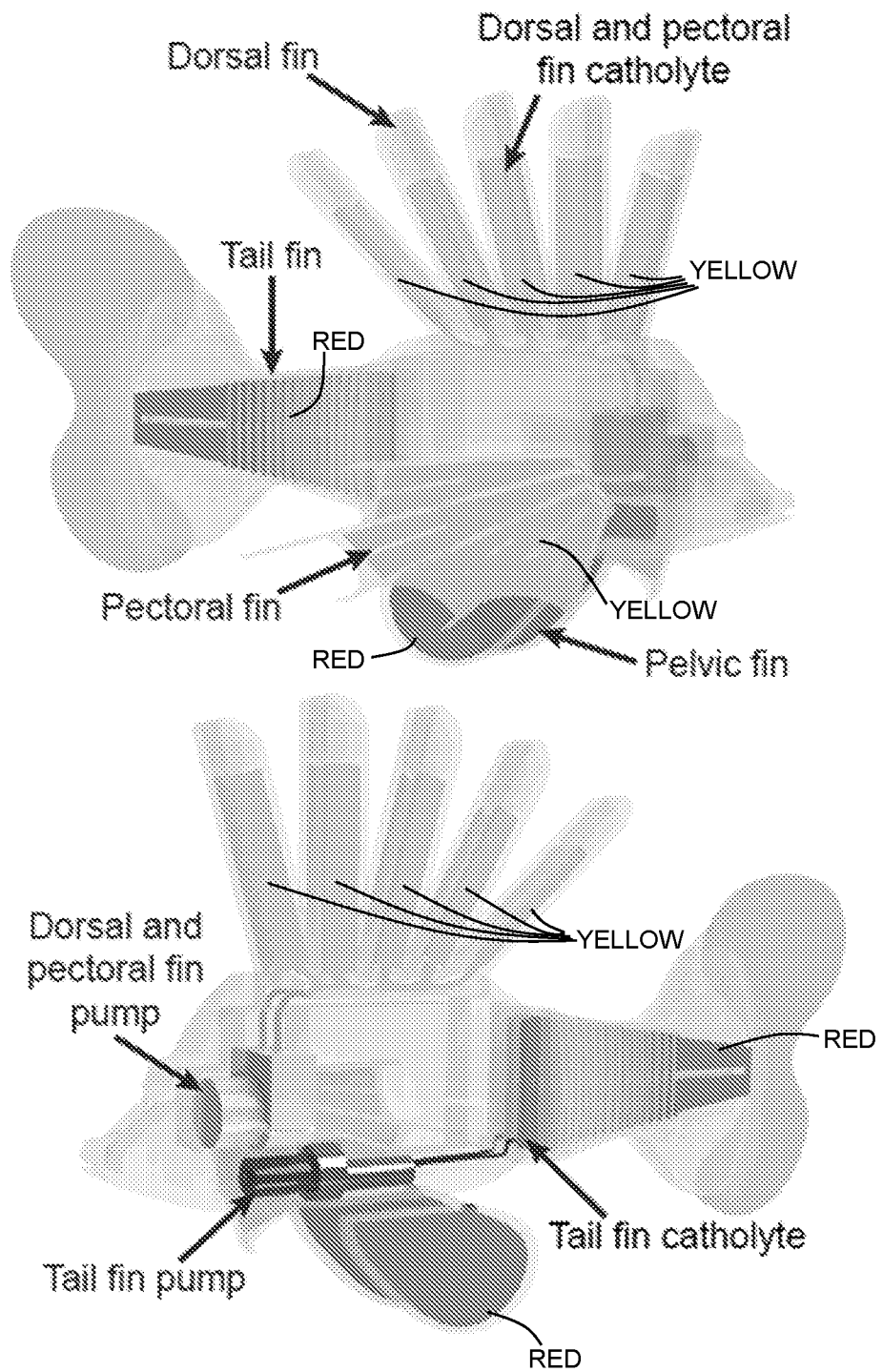
FIG. 2A: Renderings of a lionfish-inspired robot powered by a multifunctional Zinc-Iodide redox flow battery, showing the liquid catholyte in the tail fin (red) and dorsal/pectoral fins (yellow) highlighted.
Figure 2B:
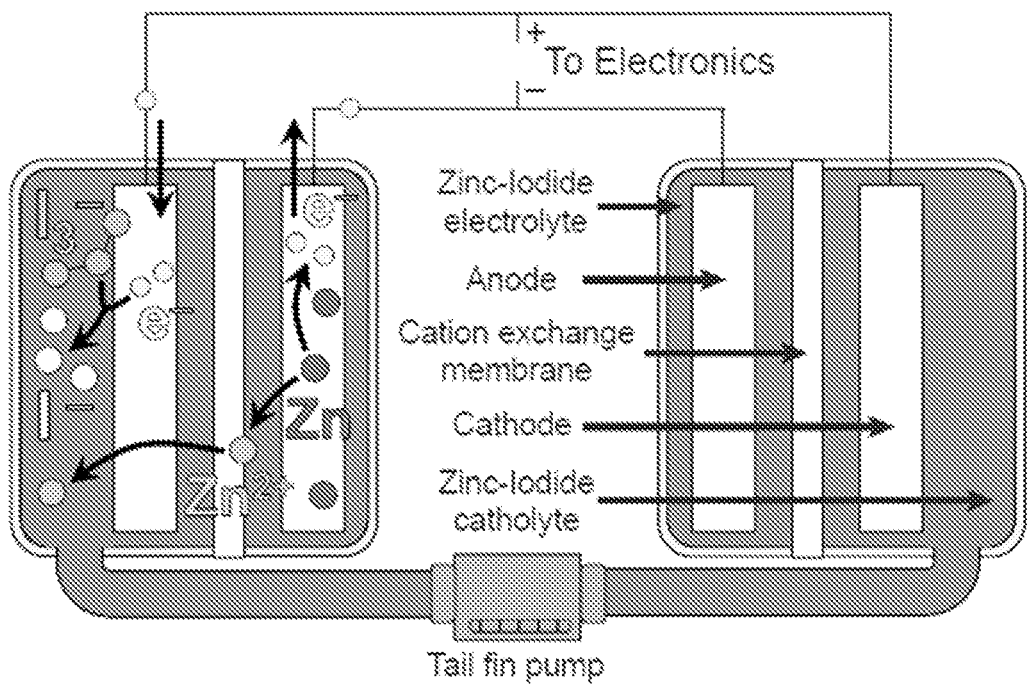
FIG. 2B: A schematic of the zinc-iodide redox flow battery used for the exemplary robot shown in FIG. 2A.
Figure 2C:
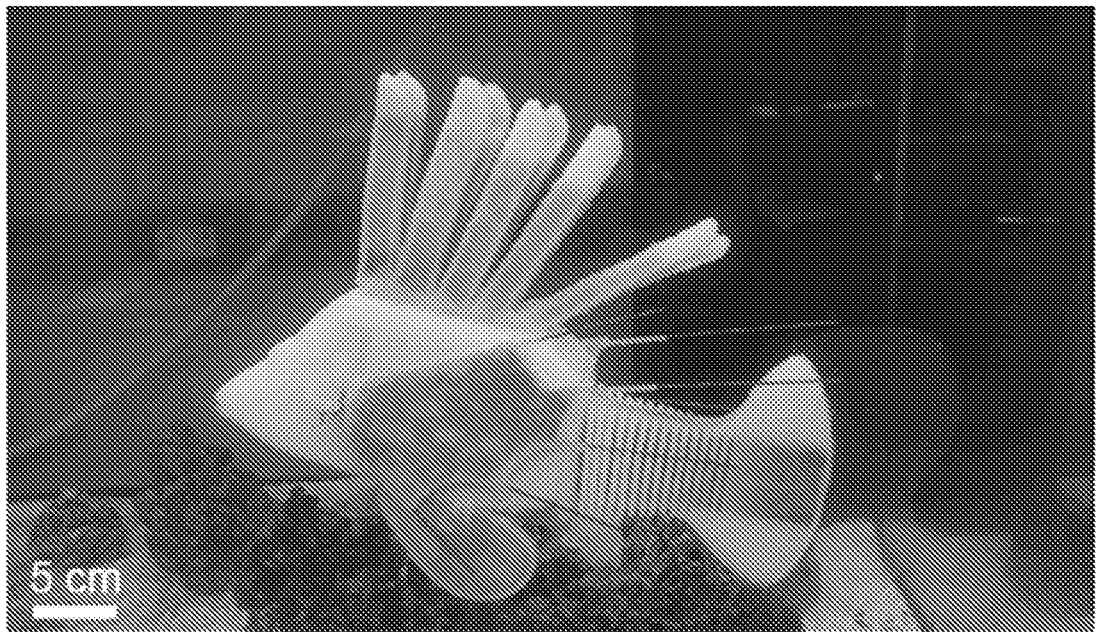
FIG. 2C: The assembled robot of FIGS. 2A and 2B swimming underwater via tail fin actuation.

In an exemplary embodiment of the present disclosure, an electrohydraulic RFB-based device is provided that enables a new combination of functions in a mobile robot: hydraulic force transmission, actuation, and energy storage for a geometric increase in system energy density. While this concept is generalizable to many machines and robots, its effectiveness is demonstrated here through an untethered, lionfish-inspired, aquatic soft robot (FIGS. 2A and 2C). This robot contains an energy dense, synthetic vascular system comprised of interconnected zinc-iodide flow cell batteries that supply power to onboard pumps and electronics through electrochemical redox reactions (FIG. 2B). Simultaneously, the pumping of the liquid half-cell transmits mechanical work to the fins, allowing the robot to swim. The complete robotic fish has a system energy density of 53 J $g^{-1}$ and can swim for long durations (max theoretical operating time=36.7 hours) at 1.56 body lengths per minute, up stream. The exemplary robot can also fan its pectoral fins, a behavior lionfish use to communicate.

The example robot's energy storage mechanism utilizes hybrid redox flow battery chemistry, as the liquid catholyte contains a solid species (zinc) that is deposited on an electrode (anode) during charging. The device shares many of the advantages of RFBs, including independent control over power density (electrode area) and energy density (electrolyte/catholyte volume), design flexibility, and low material cost. While conventional RFB designs are made from rigid materials, the exemplary synthetic vascular system contains flexible electrodes and a cation exchange membrane encased in a soft silicone skin, allowing it to bend (Bending stiffness K=7.17 N $cm^2$) and dilate to accommodate fin movement. Zinc-iodide chemistry was used due to its previously demonstrated high energy density ($I^->200$ Wh $L^{-1}$) relative to many other RFB chemistries, near neutral pH, and low viscosity. The traditional drawbacks of aqueous RFB designs (lower volumetric power density and operating voltage) were circumvented by wiring the fin battery cells in series to increase output voltage and by distributing the battery electrodes throughout the large fin areas ($A_{total}$=432 $cm^2$) to maximize power density.

Results

FIG. 2B shows a schematic representation of our multifunctional battery. Energy is stored between a redox couple of solid zinc in the anode and highly soluble (theoretically, up to 7.0 M) triiodide in the aqueous catholyte. The zinc is oxidized during discharge, releasing electrons and soluble zinc ions. The electrons flow through the robot's electronics to the catholyte, powering the microcontroller and pumps that circulate the catholyte solution. The zinc ions simultaneously flow through the electrolyte and cation exchange membrane to the catholyte where they balance the charge as triiodide is reduced to iodide. The circulating catholyte replenishes the local concentration of $I_3^-/I^-$, which maintains a constant power density during cycling. The combination of a solid anode and highly soluble catholyte enables a high theoretical energy density ($I'\sim 322$ Wh $L^{-1}$), about half that of a Tesla model S lithium ion battery ($I'=676$ Wh $L^{-1}$) (See supplementary information).

Figure 3A:
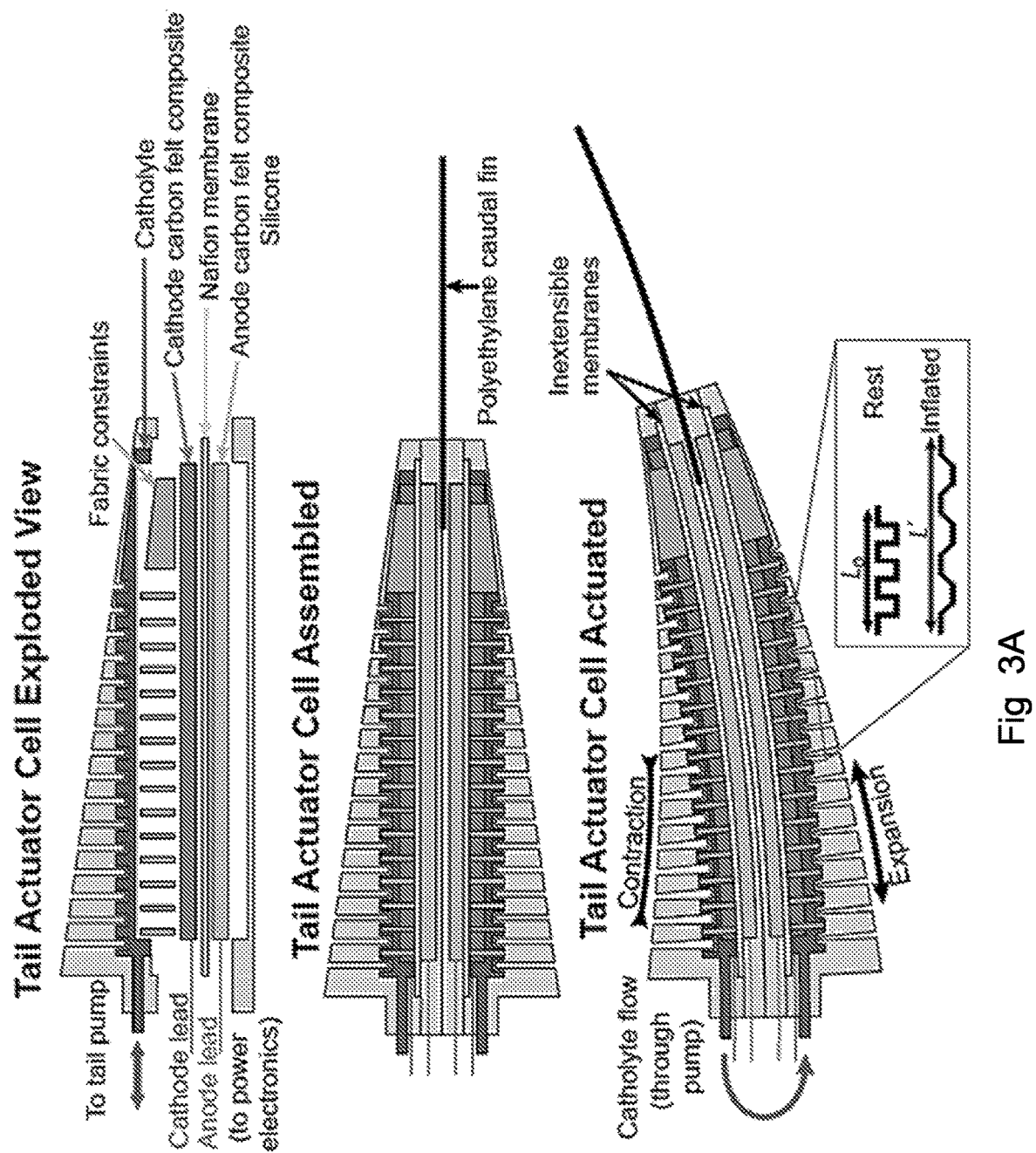
FIG. 3A: Schematic representations of the tail fin of the robot of FIGS. 2A-2C, and a diagram detailing actuation of the tail fin.
Figure 3B:
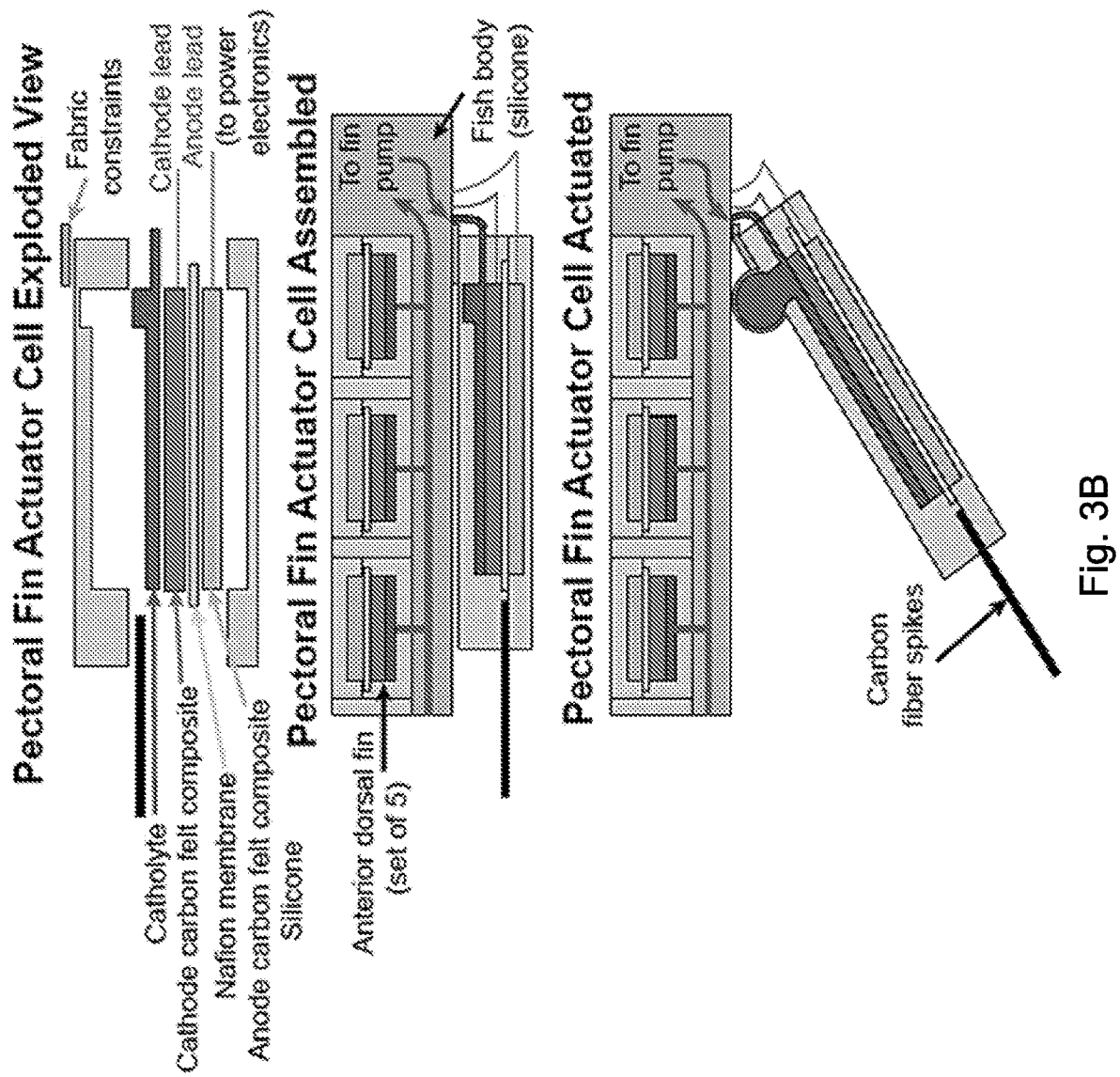
FIG. 3B: Schematic representations of a pectoral fin of the robot of FIGS. 1A-1C, and a diagram detailing actuation of the pectoral fin.
Figure 7:
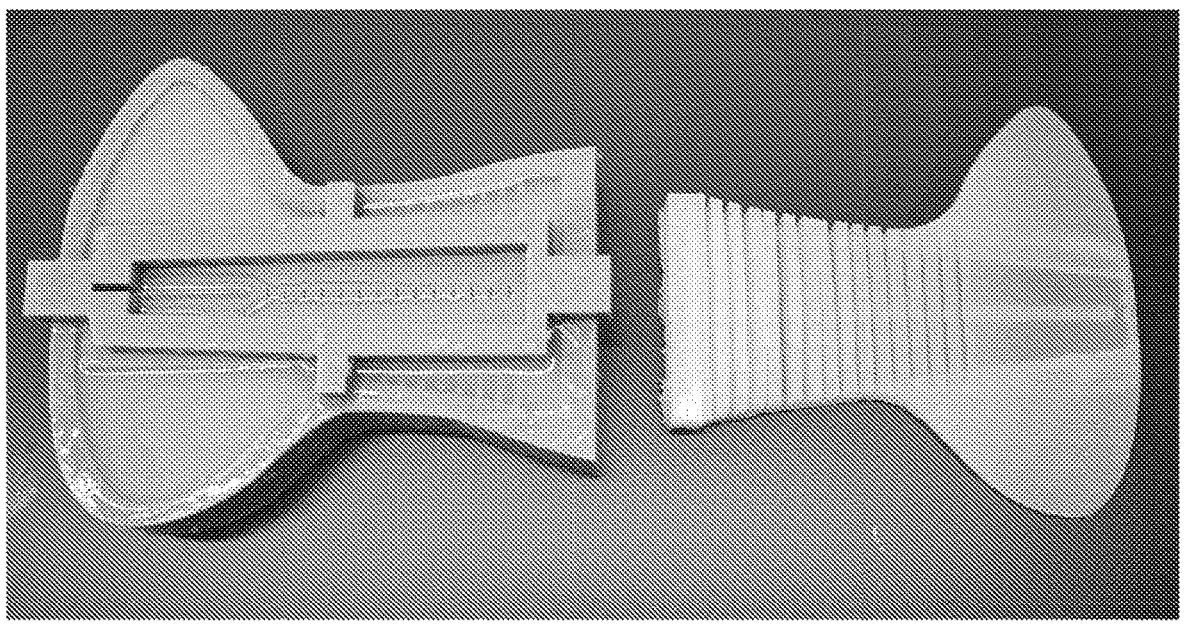
FIG. 7: Replica Molding of Robot Parts. One half of the robot's silicone tail is being cast (left) in a 3D printed mold, with the finished part (right) also shown. A two-part mold was used in the fabrication process to generate the pleats and fluidic channels in the final part.

FIGS. 3A and 3B shows a cross sectional diagram of the tail and pectoral fin actuator cells. Replica molding was used to create the silicone exterior of the robot, within which internal channels were patterned for fluidic actuation and larger cavities to hold the pumps and control hardware (see FIG. 7).

1 mm thick pieces of carbon felt (G150, AvCarb®) were used to create the flexible anode and cathode electrodes. Nickel wire (0.25 mm diameter) and 3 ply stainless steel thread (Adafruit) were woven into the anode and cathode felts respectively to improve the electrical conductivity. The resulting anode felt composite was capable of mechanically supporting electroplated zinc as the active material, while the cathode felt composite provided an oxidation resistant, high surface area electrode for the iodide reaction. A Nafion® 115 (Dupont) cation exchange membrane was placed between these felt composites and used a silicone epoxy sealant (Silpoxy, Smooth-On) to create a watertight design.

Figure 3C:
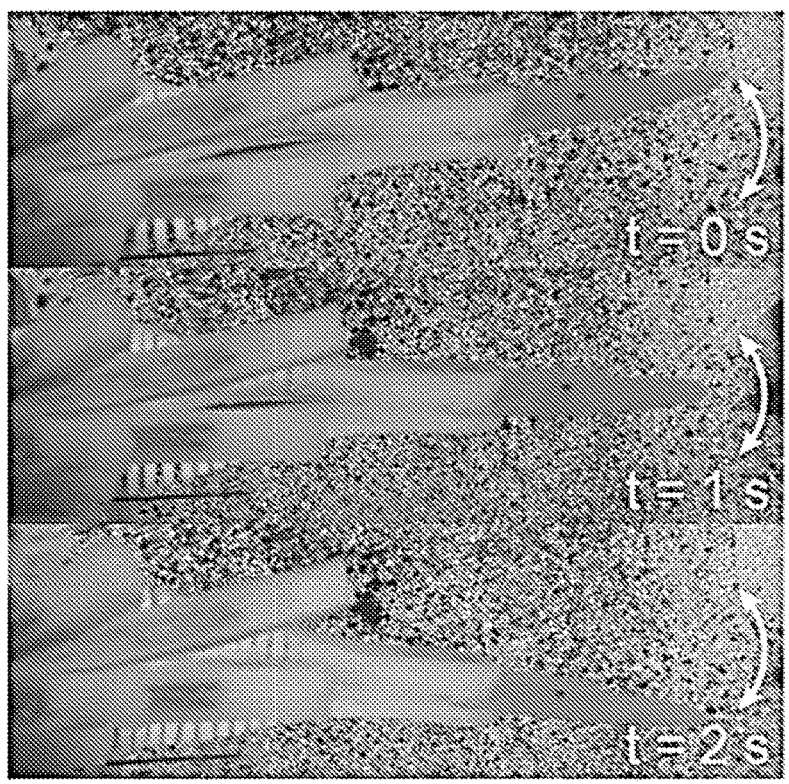
FIG. 3C: A series of photographs showing underwater tail fin actuation.

Tail actuation (FIGS. 3A and 3C) was initiated when catholyte was pumped from the left (sinistral) side of the tail to the right (dextral). FIG. 3A shows how the pumped catholyte pressurizes and inflates the sinistral pleated segments and produces subatmospheric pressure to compress the dextral ones. The opposing pressures provide a torque around the stiffer components at the tail's center, which translates into a bending motion. Cycling the catholyte between the sides of the tail results in a swimming motion that is approximately carangiform in nature.

Figure 3D:
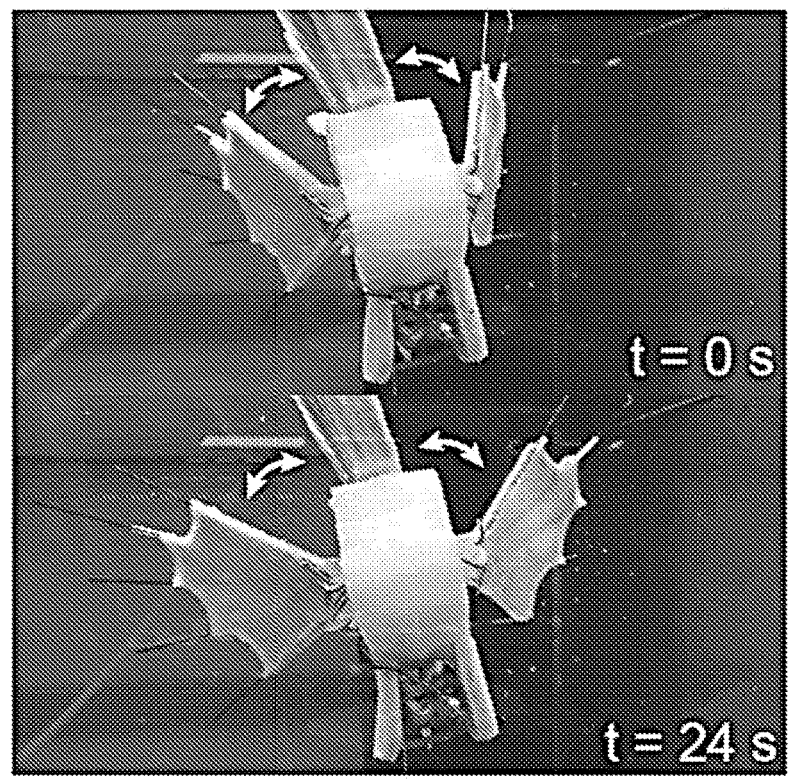
FIG. 3D: Photographs showing underwater fanning of the pectoral fins.

A separate peristaltic pump controls the fanning of the pectoral fins. Catholyte is stored in the two sets of dorsal fins, which are each linked to either the left or right pectoral fin. As catholyte is pumped from the dorsal fins to the pectoral fins, the influx of liquid pushes the pectoral fins outward from the fish body (FIGS. 3B and 3D). The movement of the catholyte from the dorsal fin to the pectoral fins is fully initiated in under 5 seconds. The tail fin and pectoral fin RFB cells are separate in this design, and an embedded microcontroller selects the pump that is operational while controlling the direction of catholyte flow.

Figure 4C:
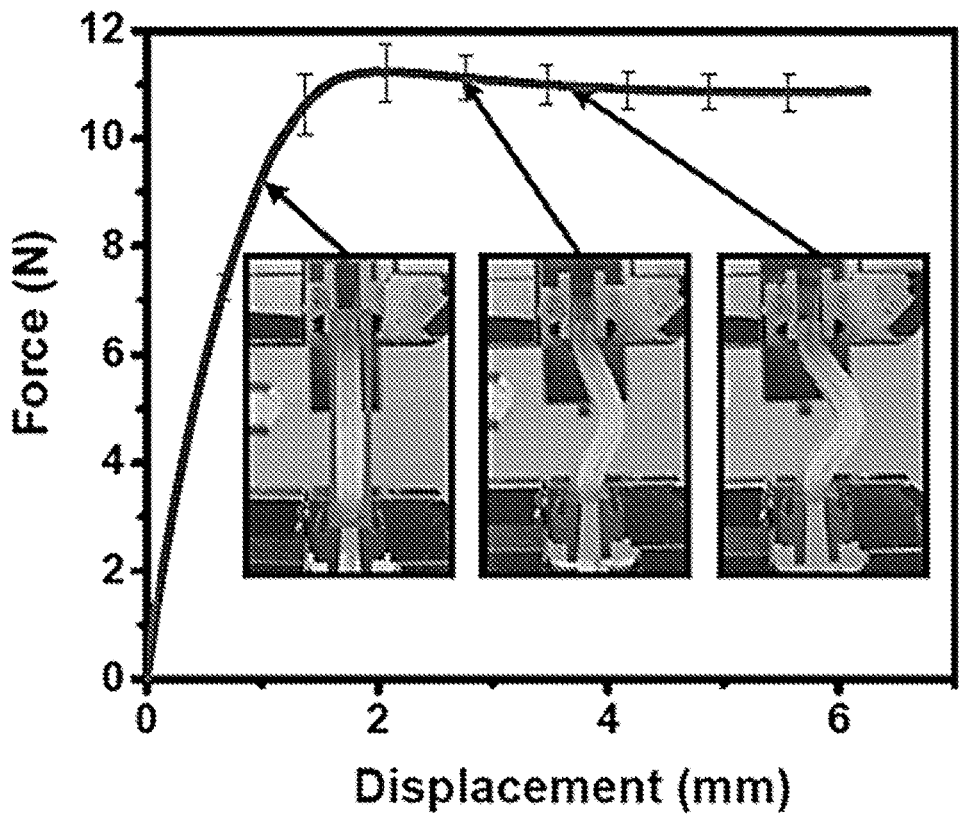
FIG. 4C: A graph of the measured force vs test grip displacement during buckling testing of the composite cell (n=8, mean±s.d.) of FIGS. 4A and 4B.
Figure 4D:
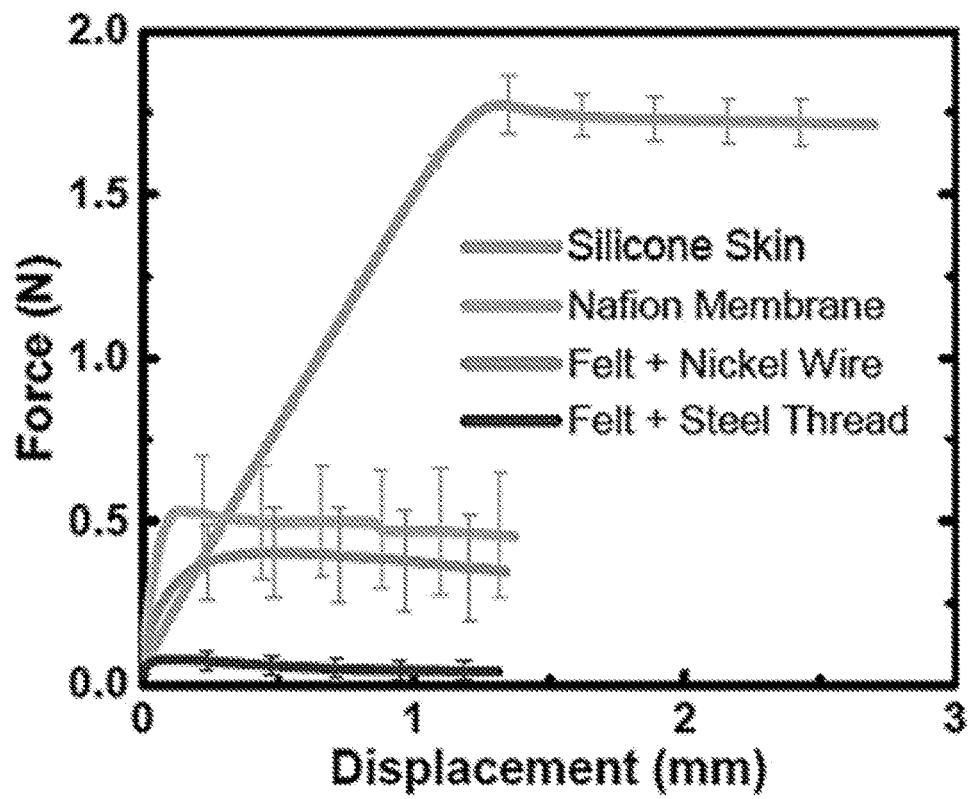
FIG. 4D: A graph of the measured force of the individual cell components (n=8, mean±s.d.) of FIG. 4A.

We used soft materials in the construction of our battery cells to enable bending and flexing of the fins during actuation without sacrificing power or performance. We determined the bending stiffness of the cells to quantify battery compliance. Sometimes referred to as "flexural rigidity" or "flexural stiffness", bending stiffness, $K=EI$, is defined as the product of a material's elastic modulus, E, and its area moment of inertia, I. The bending stiffness of fish bodies and tails has been studied at length by scientists to better understand their swimming biomechanics. We calculated the bending stiffness of the cells, in a simplified geometry, by performing buckling experiments on both the batteries and their individual component materials. By measuring the maximum force that initiates buckling, F, we could determine the bending stiffness using Euler's equation for the buckling of columns, $$F = \frac{\pi^2 EI}{(\alpha L)^2} \tag{1}$$

where $\alpha$ is the column effective length factor, and L is the unsupported length of the column. We employed the manufacturing techniques discussed previously to create a rectangular battery cell with the same cross section of materials found within the body of the fish (FIGS. 4A and 4B). FIG. 4C shows the buckling data for this composite cell and its component materials. The results for each material are tabulated in Table 1 (below). The bending stiffness of the composite battery cell was $K=7.17$ N $cm^2$. Among the component materials, the silicone skin had the greatest bending stiffness at $K=1.13$ N $cm^2$.

TABLE I

Bending Stiffness of the Battery Cell Testing Blank

| Material | Bending Stiffness, EI [N $cm^2$] | Conductivity, $\sigma$ [S $m^{-1}$] | $\sigma/EI$ [S $N^{-1}$ $m^{-3}$] |
|---|---|---|---|
| 2-ply steel thread | | $5.90 \times 10^5$ | |
| 3-ply steel thread | | $5.99 \times 10^5$ | |
| Nickel wire | | $1.02 \times 10^6$ | |
| Graphite felt | 0.05 | $4.46 \times 10^2$ | 0.89 |
| Graphite felt + 3-ply steel thread composite | 0.04 | $4.69 \times 10^2$ | 1.17 |
| Graphite felt + nickel wire composite | 0.05 | $4.81 \times 10^2$ | 0.96 |
| Graphite felt + 2-ply steel thread composite | 0.27 | $4.81 \times 10^2$ | 0.18 |
| Cation exchange membrane | 0.35 | | |
| Silicone skin | 1.13 | | |
| Composite cell | 7.17 | | |

Figure 5A:
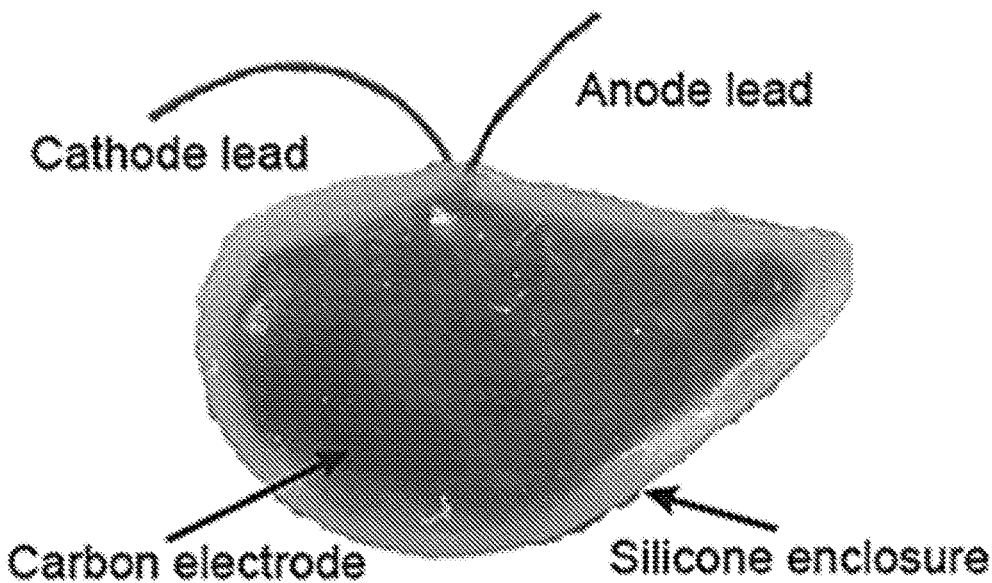
FIG. 5A: A exemplary pelvic fin battery cell used in an embodiment of the present disclosure.
Figure 5B:
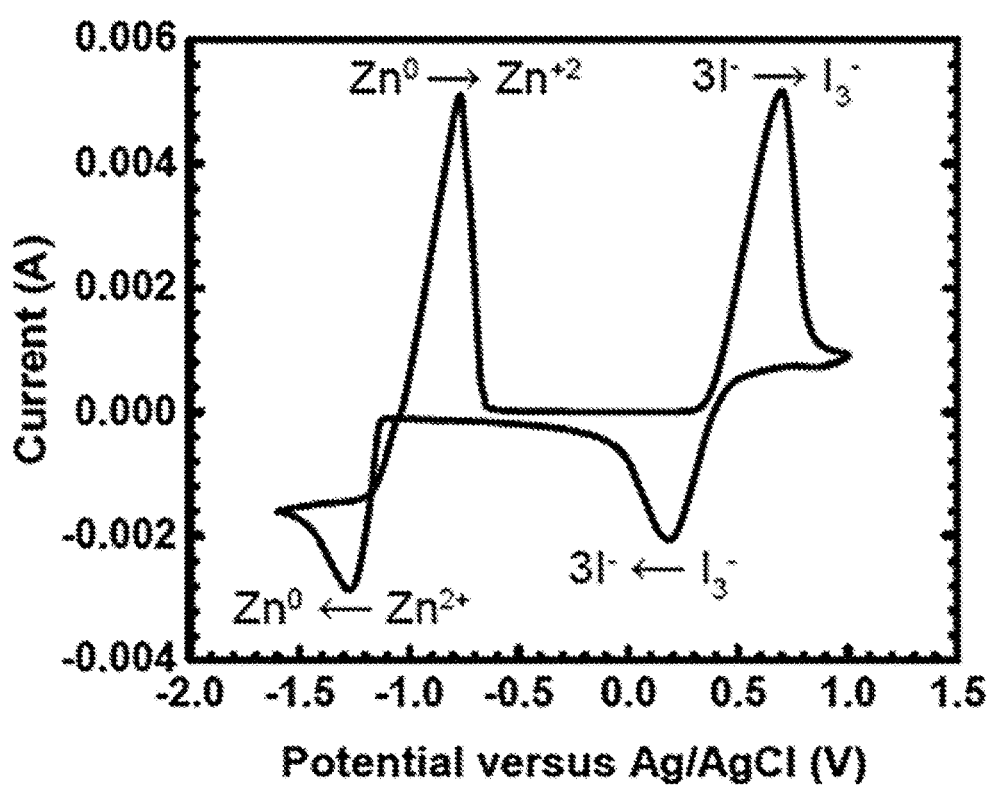
FIG. 5B: A graph showing cyclic voltammetry measurements on 0.1 M zinc iodide electrolyte.
Figure 5C:
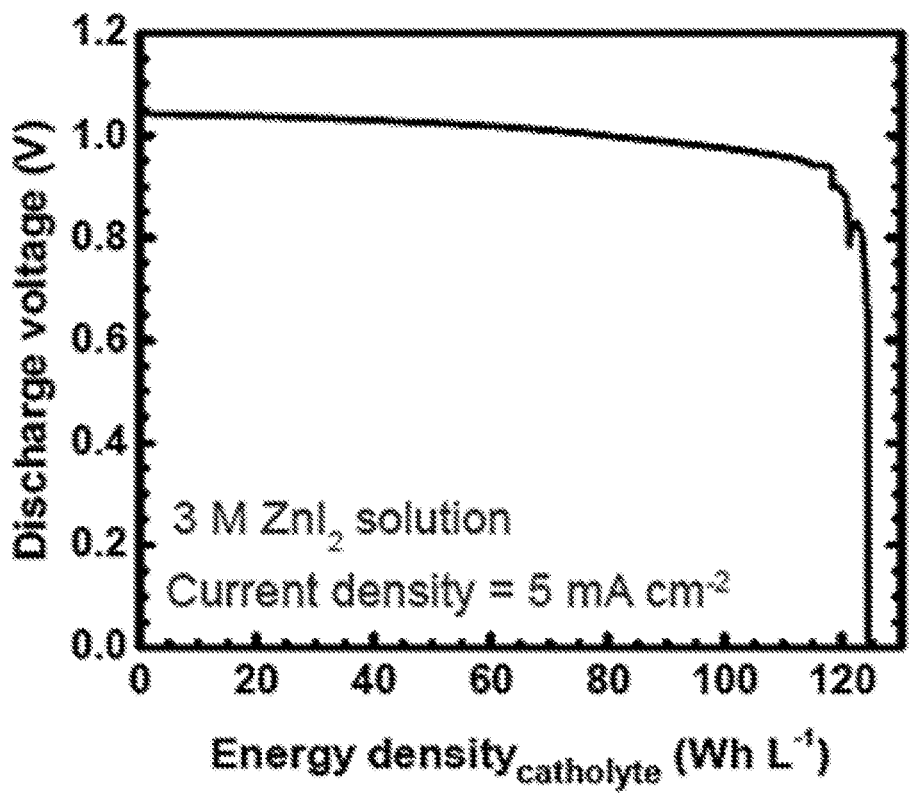
FIG. 5C: A graph showing a galvanostatic discharge curve of the pelvic fin battery of FIG. 5A at 5 mA cm$^{-2}$.

The energy storage performance of the RFB cells was characterized using the pelvic fin batteries (FIG. 5A). FIG. 5B shows cyclic voltammetry measurements of 0.1 M $ZnI_2$ electrolyte with 10% EtOH scanned at 50 mV $s^{-1}$. The −1.1 V and 0.5 V peaks correspond to $Zn/Zn^{2+}$ and $I_3^-/I^-$ redox pairs. The sharp zinc reduction peak indicates that there is little water reduction, which is important for preventing hydrogen gas buildup. We measured the pelvic fin energy density and power density using galvanostatic discharge at different current densities. FIG. 5C shows our measured energy density, $I'\sim 124$ Wh $L_{catholyte}^{-1}$ at $J\sim 5$ mA $cm^{-2}$ discharge current density. The maximum and average discharge voltages were 1.06 V and 1.00 V respectively.

Figure 5D:
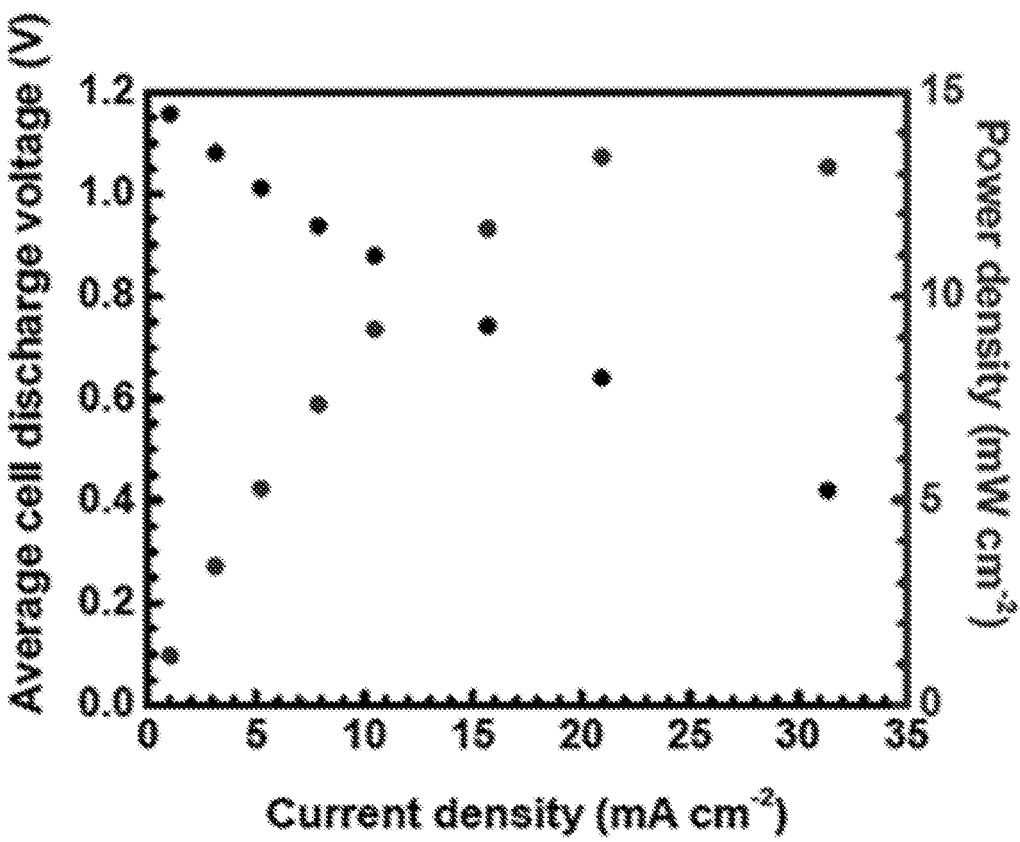
FIG. 5D: A polarization plot for the fin cell of FIG. 5A.
Figure 5E:
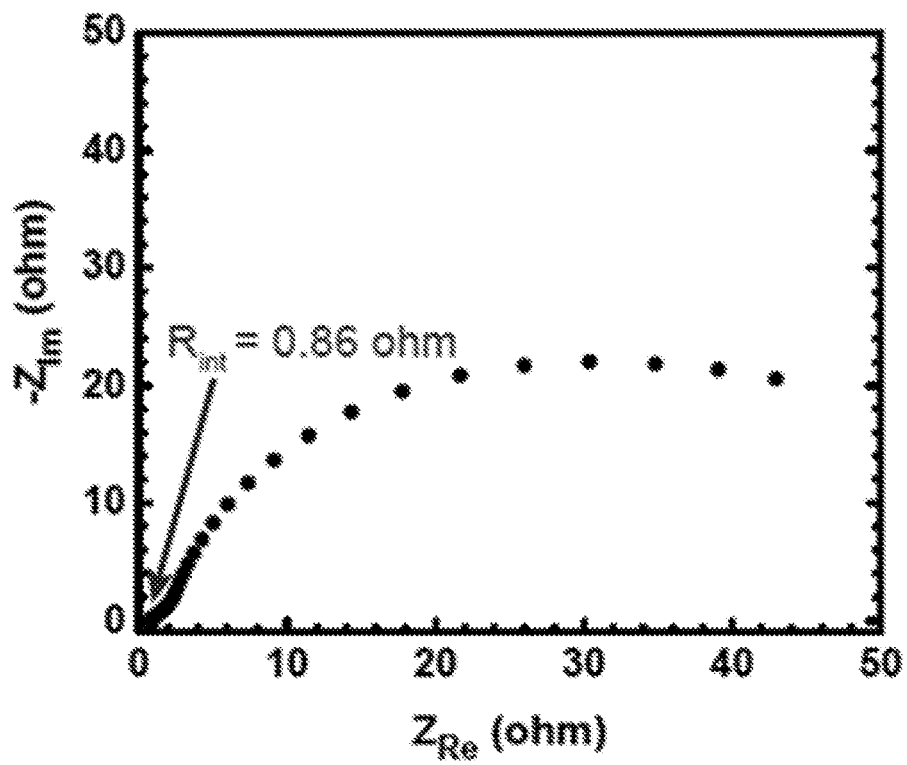
FIG. 5E: A graph showing electrochemical impedance spectroscopy results for the fin cell of FIG. 5A.
Figure 5F:
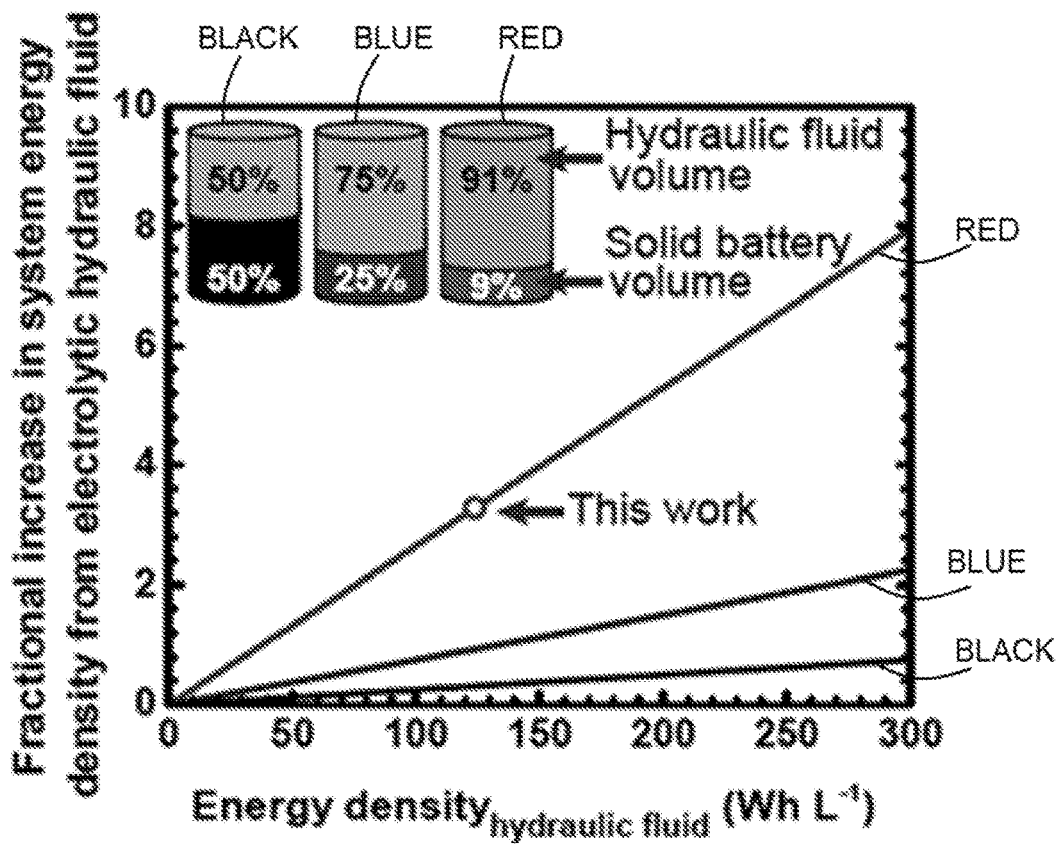
FIG. 5F: A plot showing the fractional increase in the energy density of an embodiments of the present system (red) due to the inclusion of an electrolytic hydraulic fluid as a function of the fluid energy density. This plot also shows the potential effect of different volume fractions of liquid and solid battery (blue and black). The solid battery is represented by a high energy density (400 Wh $L^{-1}$) lithium-ion battery.

To meet the power requirements of the electric pump and onboard electronics (2.05 W, see supplementary information), the electrode materials and component spacing were designed to reduce internal ohmic voltage losses. FIG. 5D shows a polarization curve for the pelvic fin cell, which achieved a peak power density of $Z\sim 13.4$ mW $cm^{-2}$. The voltage loss from $0<J<15$ mA $cm^{-2}$ is primarily ohmic and low due to the 0.86 ohms full cell resistance, measured using electrochemical impedance spectroscopy (FIG. 5E). The maximum power density of the robot, when normalized by the total fluid volume in the vascular system, was determined to be 19.2 mW $cm^{-3}$. FIG. 5F shows how the inclusion of electrolytic fluid 124 Wh $L^{-1}$; $V_{catholyte}=0.22$ L; $\rho\sim 1.64$ g $mL^{-1}$) increases the energy density of hydraulically actuated systems. For the exemplary embodiment of the presently disclosed system, this increase was more than 325%. The y-axis indicates the fractional increase in the total volumetric energy density of the exemplary robot relative to an identical, hypothetical design that uses a non-energized liquid, such as water, as its hydraulic fluid. This simple model can be modified and applied to other systems infused with electrolytic fluids to evaluate how different design considerations, such as the volume fraction of fluidic and solid energy sources (FIG. 5F), the energy content of those sources, and the concentration of electrolyte (FIG. 8), contribute to increases in system energy density.

Figure 9:
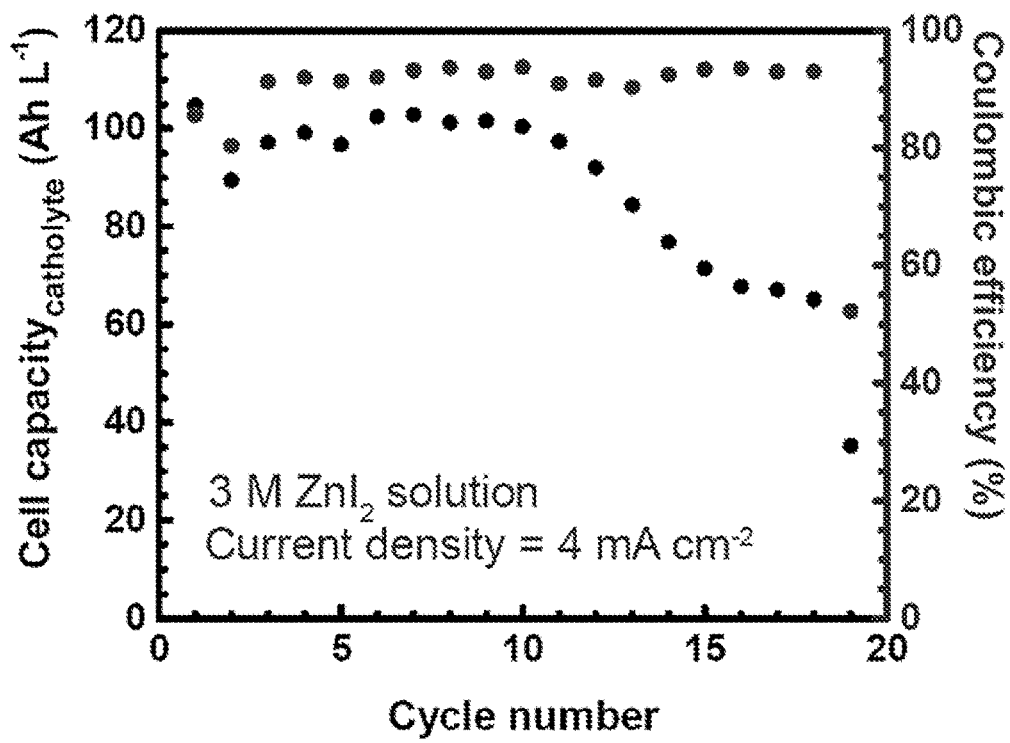
FIG. 9: Cell capacity and cycling efficiency data for the pelvic fin cell.

The catholyte capacity and coulombic efficiency of the exemplary pelvic fin battery were measured after more than 100 hours of continuous charge and discharge cycles at J~4 mA cm$^{-2}$ (FIG. 9). The capacity starts to fade after approximately 10 cycles due to dehydration and catholyte absorption into the silicone. Better encapsulation techniques can solve this issue, as demonstrated by known, optimized $ZnI_2$ RFBs capable of operating for more than 1,000 cycles. Using the data collected from the pelvic fin cells, the maximum operating time of the robot were calculated to be 36.7 hours during tail fin actuation. The swimming performance of the robot is expected to remain consistent during operation as the discharge voltage remains constant for the majority of the battery's discharge (FIG. 5C).

Figure 6A:
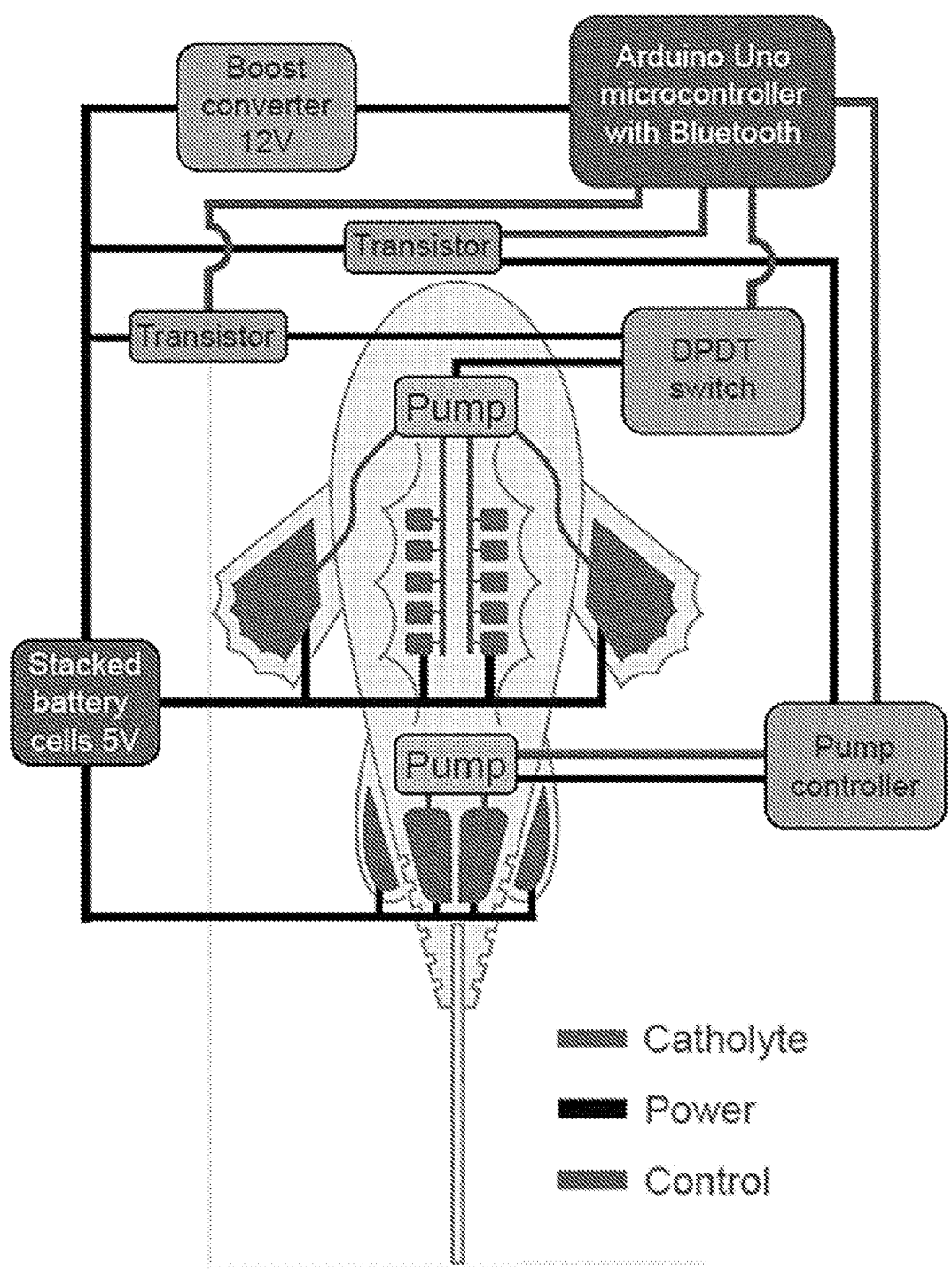
FIG. 6A: A block diagram showing the configuration of pumping, control, and electronic components of the "vascular" system of the lionfish exemplary embodiment.
Figure 6B:
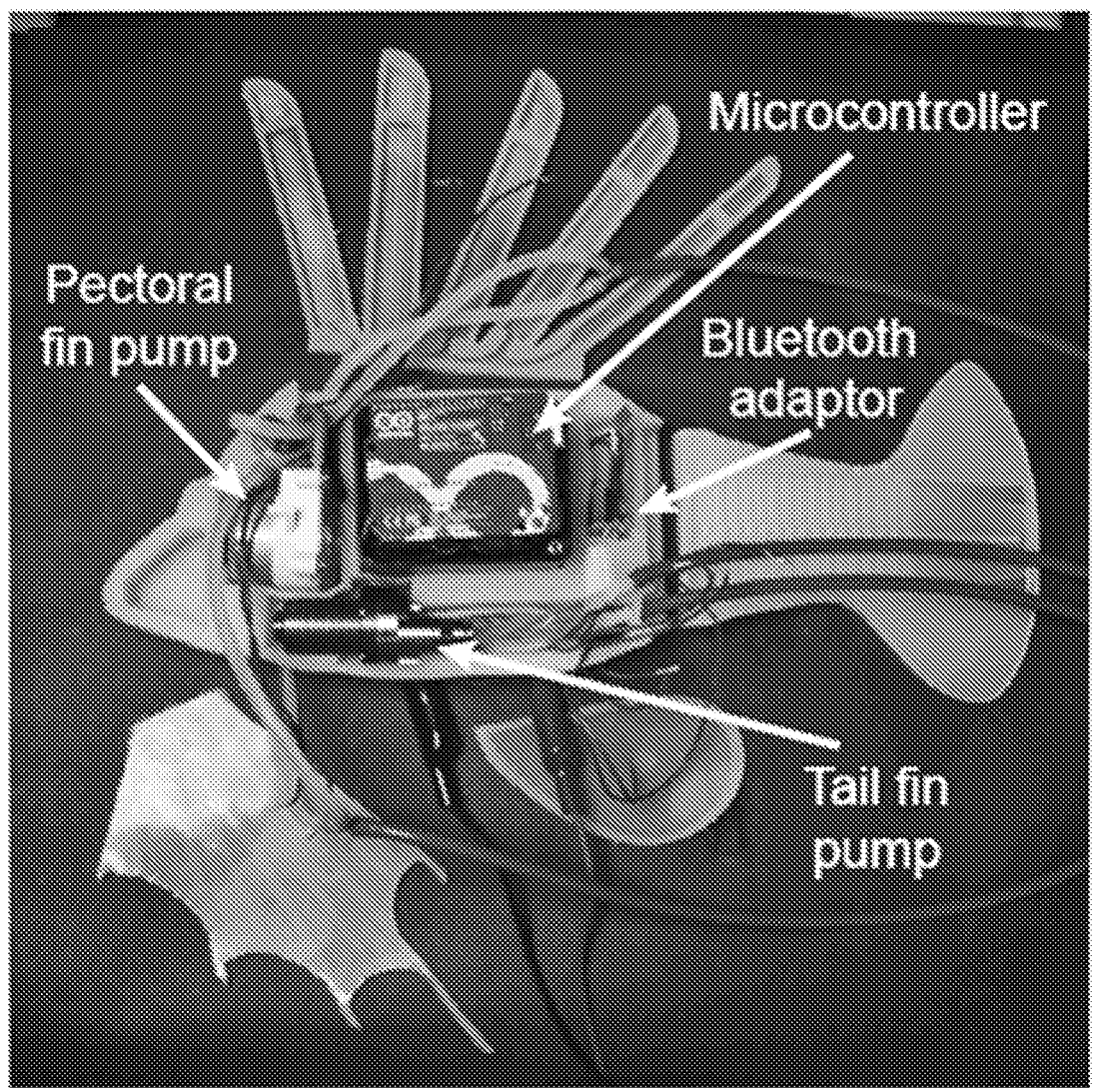
FIG. 6B: A partially disassembled exemplary robot, showing how the pumps and control hardware are housed internally.
Figure 6C:
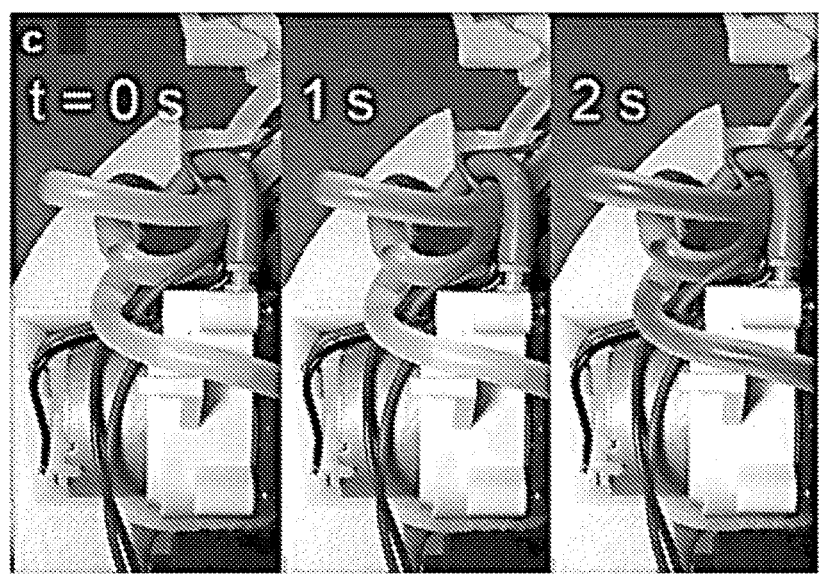
FIG. 6C: A peristaltic pump for transporting catholyte from the dorsal fins to the pectoral fins of the exemplary robot.

FIGS. 6A and 6B display the robot actuation control components. Power from the battery cells was delivered to either the tail fin pump (MGD1000S-PK-V, TCS Micropumps) or the pectoral fin pump (Yosoo16325, Yosoo) by way of transistor switches connected to the microcontroller (Arduino Uno), which was remotely toggled via a wireless Bluetooth adaptor (HC-05, DSD Tech). During tail actuation, a pump controller (EQi-MG1, TCS Micropumps) modulated by the microcontroller alternated the catholyte flow direction. To control the catholyte flow direction in the pectoral fins, a double-pole double-throw (DPDT) relay (RY5W-K, Fujitsu) was used to alternate the pectoral fin pump polarity. The tubing and the pelvic fin pump was configured to resemble a heart pumping blood throughout the fish's body (FIG. 6C).

To power the microcontroller for each of the pumps, the combined output voltage of the batteries was stepped up to 12 V using a boost converter (DD2412SA_12V, Canton Electronics). During testing, a 3 V CRV3 Li-ion battery was used in series with the RFB cells to maintain the minimum voltage requirement for the boost converter and to ensure a high power conversion efficiency. The additional battery allowed more than 5 V to be delivered to the input terminal of the boost converter. However, the battery was not essential to the electronics configuration, and could be replaced by a second, low input voltage boost converter.

Figure 6D:
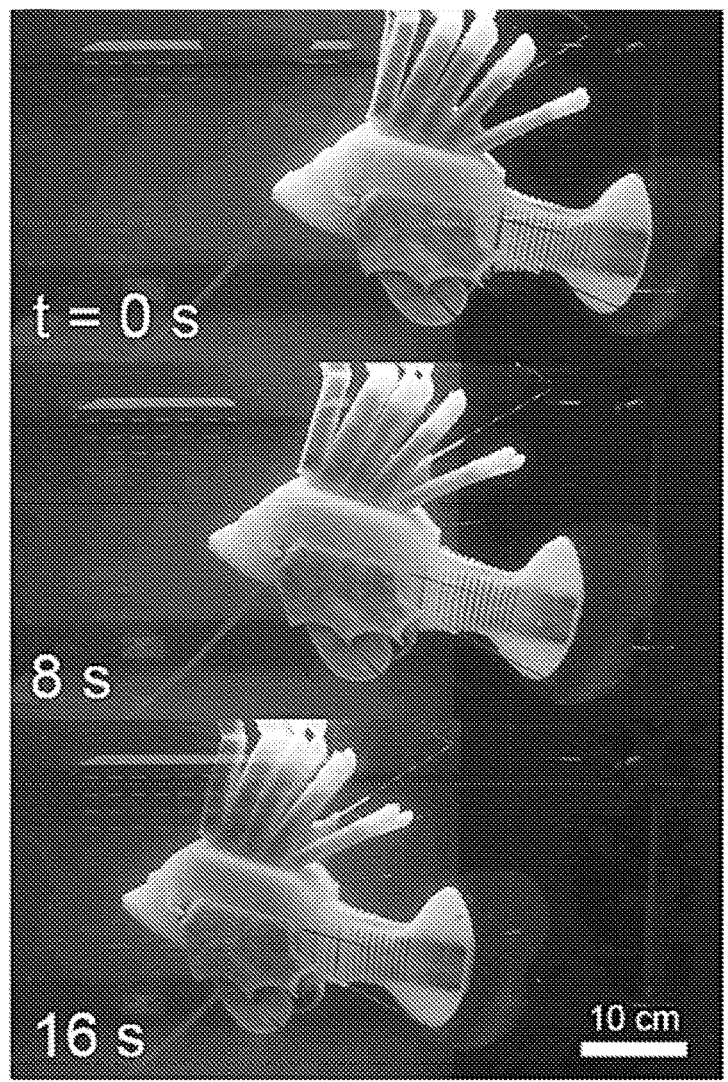
FIG. 6D: Untethered swimming demonstration in a salt water tank.

Underwater actuation tests were performed with the fully assembled robot in a 200-gallon salt water tank. The robot achieved a forward swimming speed of 1.56 body lengths per minute, against a current, when the tail fin was actuated (FIG. 6D). The swimming performance of the robot was partly limited by its buoyancy, which was not optimized in this first demonstration study (a weight was attached to the underside of the robot to ensure it was fully submerged in the tank). Future designs could circumvent this problem with fewer air pockets embedded in the fish body, or by filling those pockets with an appropriate ballast material, or otherwise.

Our work shows that energy dense hydraulic liquids can be embedded and circulated within robots to both mechanically actuate and electrically power them with large increases in system energy density. We implemented this multifunctional, synthetic vascular system into the body of an untethered, aquatic robot and demonstrated appreciable swimming speeds against a current via tail fin actuation, as well as the ability to fan the pectoral fins. We used a safe and established zinc-iodide RFB chemistry, and measured the maximum energy density (I'=124 Wh $L_{catholyte}^{-1}$ at J=5 mA cm$^{-2}$) and power density (Z=13.4 mW cm$^{-2}$ at J=20 mA cm$^{-2}$), full cell resistance (0.86 ohms), and cycling characteristics of the pelvic fin cells. We also created a compliant (K=7.17 N cm$^2$) half flow-cell battery with biologically-inspired form factors that comprise structural elements of the robot analogous to muscle and cartilage in fish.

We used soft robots to demonstrate this vascularized "robot blood," as they are a versatile platform for illustrating new methods of energy storage and conversion into motion. Several fish-inspired robots, both fully and partially soft-bodied, have been exhibited previously, with MIT's SoFi being notable for its exploration and remote control capabilities, as well as its superior 3-dimensional maneuverability. Our work differs from these other robots in that it combines structure, actuation, force transmission, and electro-chemical energy storage, through the synthetic vascular system to create a fully integrated, multifunctional design. However, further optimization of the battery chemistry, electronics configuration, hydraulic systems, and structural design of the robot will be needed to match the performance of robots like SoFi.

The actuation force and frequency of the tail fin were limited in this test embodiment due to the pumping configuration, which switches the direction of pump shaft rotation to reverse flow. Other designs, such as, for example, a continuously circulating pump with a flow reversing manifold, would increase swimming performance, as would electronics or different catholyte compositions that boost the battery voltage to deliver maximum power to the pumps. Additionally, optimized actuator designs and a more hydrodynamic form factor would decrease drag and increase swimming efficiency.

RFBs with power densities in excess of 1,300 mW cm$^{-2}$ have been achieved previously through optimization of the spacing, thickness, design, and configuration of battery components. Compressing felt electrodes, employing smaller actuators with reduced spacing between electrodes, or using improved current collectors, like stacked carbon paper, are additional methods of increasing power density that would maintain the flexibility in flow cells. Synthetic vascular systems that increase system energy density favor implementation in cm-scale or larger actuators, due to the increases in total energy and actuation amplitude associated with larger electrolyte volumes. Synthetic vascular systems implemented into smaller robots would benefit from higher power density, but would likely require increases in fluidic energy density and improvements in microscale pumps.

Example 1 Methods

Redox Flow Battery Components

The anode and cathode electrodes in the RFB cells were composed of a soft graphite felt (G150, AvCarb®) that was cut to the desired form factor and reduced to approximately 1 mm in thickness (25% of the original thickness). For the anode, strands of nickel wire (0.01 gauge Monel, Malin Co.) were woven through the felt to increase electrical conductivity. For the cathode, 3 ply, 316L stainless steel conductive thread (no. 641, Adafruit) was woven into the felt, which was resistant to oxidation from the triiodide in the catholyte.

The cation exchange membrane was composed of Nafion 115 (DuPont) cut to the desired shape. A layer of Sulky Soft n' Sheer fabric (Sulky) was embossed around the perimeter of the membrane using an impulse heat sealer to reinforce the Nafion. Excess fabric was trimmed away before final assembly. Silicone parts were fabricated by mold casting. The molds were 3D printed on a polyjet printer (Objet30 Scholar Stratasys) using Veroblue material. After printing, the molds were heated at 70° C. for 3 hours to prevent cure inhibition. Silicone prepolymer (Dragonskin 20 or EcoFlex 30, Smooth-On) was mixed, de-gassed, poured into the molds, and leveled before curing overnight. To improve the locomotion efficiency of the tail fins, a polyethylene mesh was inserted into the molds before silicone was cast to prevent unnecessary stretching (which naturally directs energy away from the desired tail bending). Only areas of the tail fin that remain flexible, but do not stretch, during actuation were reinforced with the mesh.

Catholyte

The catholyte was made with 0.1-3 M zinc iodide in distilled water. 10% ethanol was added to reduce zinc dendrite formation and increase triiodide stability.

Battery Assembly

The flexible battery cells were fabricated by assembling an anode, cation exchange membrane, and cathode in series. These components were placed into the recessed cavity between two molded silicone layers, which formed the exterior skin of the battery (FIGS. 3A, 3B, 4B). The anode and cathode electrodes were free-standing and not attached to the silicone skins, except where the steel thread and nickel wire were threaded through the silicone. The silicone layers that both directly contacted the catholyte and were not stretched during robot actuation were laminated with a polypropylene film. The silicone skins, along with the cation exchange membrane between them, were compression sealed together using a silicone epoxy (Silpoxy, Smooth-On). Finally, the catholyte was injected into the cathode compartment of the battery. The injection holes were then sealed with the silicone epoxy.

Mechanical Testing

Buckling tests were performed on a Zwick Roell z010 instrument to determine the bending stiffness of the battery cell and its component materials. We used the same battery assembly procedure detailed previously to create a 10 cm×5 cm rectangular battery cell with the same cross section of materials found within the robot. The catholyte was omitted from the battery cell for convenience (see FIG. 10). All tests on the battery and its component materials were conducted at room temperature using a strain rate of 25 mm min$^{-1}$, a grip-to-grip distance of 50 mm, and a preload of 0.05 N. The composite cell was tested using a 10 kN load cell, while the individual component materials of the composite were tested with a 20 N load cell. The data was averaged across common strain range and plotted (n=8) in Origin® (FIG. 4C). The peak force (critical load) recorded during buckling was used to calculate the bending stiffness of the materials.

Electronics and Robot Control

A 6 W, 2-24 V to 12 V DC step-up/step-down voltage regulator module (DD2412SA_12V, Canton Electronics) was used to increase the output voltage of the battery cells. A standard 3 V CRV3 battery was put in series with the battery cells during actuation tests to ensure that the total voltage of the cells continuously exceeded the 2 V minimum of the voltage regulator module. An Arduino Uno was fitted with a wireless Bluetooth module (HC-05, DSD Tech) and embedded in the body of the robot to allow for wireless control. A 6V DC peristaltic dosing pump (Yosoo16325, Yosoo) was used to transfer the catholyte between the dorsal fins and the pectoral fins. We chose this pump because it doesn't directly interface with the fluid and can be reversed by changing the motor polarization. A 5 V DC DPDT Signal Relay Module (RYSW-K, Fujitsu) was used with the dorsal fins to switch between forward and reverse fanning. A lightweight, self-priming pump (MGD1000S-PK-V, TCS Micropumps) was used for tail actuation. This pump's high flow rate (500 mL min$^{-1}$) for its small size (61×32×30 mm) made it ideal for our design. We controlled the direction and power of this pump using the EQi-MG1 brushless control unit (TCS Micropumps). Simple transistors were used as low power switches for turning each pump on and off.

Charge and Discharge Methods

We used a Neware CT-3008 as our battery testing system. The battery cells were galvanostatically charged and discharged.

Cyclic Voltammetry (CV)

CV measurements were conducted on CHI600 workstation (Model 600E, CH Instruments Inc.). The voltage was scanned from −1.6 V to 1.0 V versus a Ag/AgCl reference electrode at 50 mV s$^{-1}$ in 0.1 M ZnI with 10% EtOH. Graphite was used as the working and counter electrode.

Electrochemical Impedance Spectroscopy

We conducted electrochemical impedance spectroscopy measurements on a charged pelvic fin battery cell using a 1260A Solartron Impedance Analyzer from 0.1 to 50 kHz.

Statistical Information

Sample size, mean, and standard deviation are reported for all data sets where applicable. No statistical methods were used to predetermine the sample sizes for stiffness testing or battery performance characterization. All statistical analyses were performed in Microsoft Excel (Excel for Mac, Version 15.25, 2016) and Origin (Academic Version, 2016).

Lionfish Design Metrics and Calculations

Battery Membrane/Cell Areas:
Left and right tail fin cell=70 cm$^2$ each.
Left and right pelvic fin cells (electrically connected to the tail fin)=38 cm$^2$ each.
Total area of the tail fin cell system=216 cm$^2$.
Left and right pectoral fin cells=54 cm$^2$ each.
Left and right dorsal fin cells=54 cm$^2$ each.
Total area of the dorsal/pectoral fin cell system=216 cm$^2$.
Total cell area of the fins=432 cm$^2$.

Battery Electrode Areas:
Total electrode area=total area of cathode and anode components=2×(membrane area)=864 cm$^2$.

Electrolyte Volumes:
Total catholyte volume in tail cell system=216 cm$^2$×0.5 cm=0.108 L
Total catholyte volume in dorsal/pectoral fin system=216 cm$^2$×0.5 cm=0.108 L.
Total anolyte* volume in tail cell system=216 cm$^2$×0.2 cm=0.043 L.
Total anolyte* volume in dorsal/pectoral fin system=216 cm$^2$×0.2 cm=0.043 L.
Total catholyte volume=0.216 L
Total ZnI$_2$ battery volume=0.302 L
*(anolyte here refers to the electrolyte housed in the anode half-cell to facilitate ion and electron transfer)

Maximum Power and Energy Density of the Robot
Max power density of cell~13.4 mW cm$^{-2}$ (See FIG. 5D).
Power density normalized for all fluid=(13.4 mW cm$^{-2}$× 432 cm$^2$)/302 cm$^3$=19.2 mW cm$^{-3}$.
Total catholyte energy content=124 Wh L$^{-1}$× 0.216 L$_{catholyte}$=26.784 Wh.

Total CRV3 battery energy content=2700 mA hr×3V=8.1 Wh.

Total robot weight=2.38 kg.

Total robot energy content=26.784 Wh+8.1 Wh=34.884 Wh~126 kJ

Theoretical max energy density of $ZnI_2$=322 Wh $L^{-1}$ at the solubility limit of $ZnI_2$ in the water Max energy density of Tesla Model S Li-ion battery=676 Wh $L^{-1}$.

Power Required for Swimming—Tail Fin Actuation

Power through pump=5 V×0.25 A (pump)=1.25 W

Power through electronics=[5 V×0.0036 A (transistor)+5 V×0.0036 A (transistor)+[5 V×0.02 A×2 pins=0.2 W (Arduino pins)]+5 V×0.045 A (Arduino main)]/0.8 (12 V Boost efficiency)=0.58 W.

Power required for tail fin actuation=1.25 W+0.58 W=1.83 W

Current through each cell=1.83 W/5 V=0.365 A

Current density in battery=0.365 A/216 $cm^2$=1.7 mA $cm^{-2}$ (compared to ~20 mA $cm^{-2}$ at peak power)

Average battery discharge~1 V (see FIG. 5C)

Peak energy density of catholyte~124 Wh $L^{-1}$ (see FIG. 5C)

Total operating time=(124 Wh $L_{catholyte}^{-1}$×0.108 $L_{catholyte}$)/(0.365 A×1 V)=36.7 hours Power Required for Fanning Fins—Pectoral Fin Actuation Power through pump=5 V×0.1 A (pump)=0.5 W Power through electronics=[5 V×0.0036 A (transistor)+5 V; 0.16 A (DPDT)+[5 V; 0.02 A; 2 pins=0.2 W (Arduino pins)]+5 V; 0.045 A (Arduino main)]/0.8 (12 V Boost efficiency)=1.55 W Power required for pectoral fin actuation=1.55 W+0.5 W=2.05 W Current through each cell=2.05 W/5 V=0.41 A Current density in battery=0.41 A/216 $cm^2$=1.9 mA $cm^{-2}$ (compared to ~20 mA $cm^{-2}$ at peak power)

Average battery discharge~1 V (see FIG. 5C)

Peak energy density of catholyte~124 Wh $L^{-1}$ (see FIG. 5C)

Total operating time=(124 Wh $L_{catholyte}^{-1}$×0.108 $L_{catholyte}$)/(0.41 A×1 V)=32.7 hours Calculating Fractional Increase in Energy Density from Electrolytic Hydraulic Fluid.

The equation used to calculate the increase in energy density associated with the inclusion of an electrolytic hydraulic fluid is as follows:

$$\text{Fractional Increase} = \frac{\Gamma_{+energized\ fluid}^{system}}{\Gamma_{-energized\ fluid}^{system}} = \frac{(\Gamma_f V_f + \Gamma_s V_s)/V_{tot}}{(\Gamma_s V_s)/V_{tot}} - 1 \quad (2)$$

This quantity represents the ratio of energy densities between our proposed robot design, and an equivalent, identical design that uses a non-energized hydraulic fluid. This relationship isolates the energy density increase attributed to just the electrolytic hydraulic fluid.

$\Gamma_{+energized\ fluid}^{system}$=The energy density of a system with electrolytic hydraulic fluid $\Gamma_{-energized\ fluid}^{system}$=The energy density of a system without electrolytic hydraulic fluid, where a non-energized fluid (e.g., water) is used for hydraulic actuation $\Gamma_f$=The energy density of the electrolytic hydraulic fluid (124 Wh $L^{-1}$ in this work)

$\Gamma_s$=The energy density of the solid battery components (400 Wh $L^{-1}$ is used for each calculation in FIG. 5F)

$V_f$=The electrolytic fluid volume or volume fraction when normalized (91% in our system)

$V_s$=The solid battery volume, or volume fraction when normalized (9% in our system)

$V_{tot}$=The total volume of the actuation and energy storage components of the robot or system of interest.

The value 1, or 100%, is subtracted from this term so that it represents a fractional increase relative to $\Gamma_{+energized\ fluid}^{system}$ (e.g., a result of "1" when evaluating the above equation indicates a 100% increase, or a doubling, of the energy density of the system).

Figure 8:
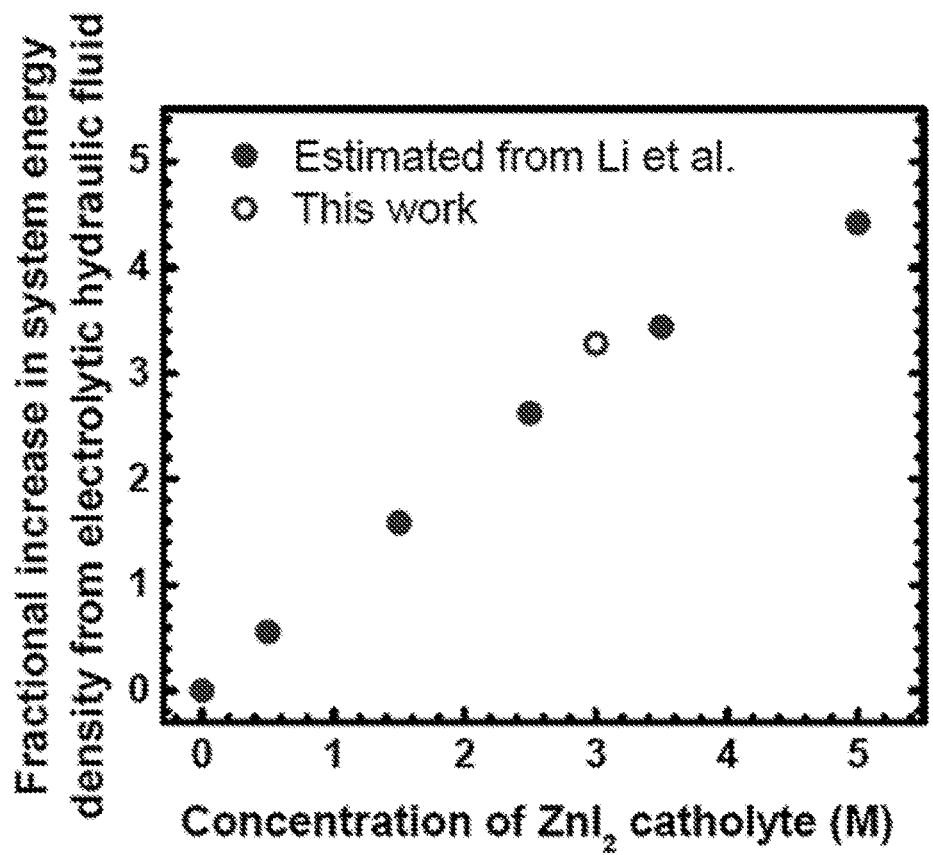
FIG. 8: A graph showing the effects of $ZnI_2$ concentration on the overall increase in system energy density for the exemplary lionfish robot.

Equation (2) can be adapted to calculate the fractional increase in energy density for other electrolytic hydraulic systems with, for example, different electrolyte and solid battery volumes (as shown in FIG. 5F), different solid battery energy densities (by varying $\Gamma_s$), and different electrolyte energy densities (by varying $\Gamma_f$) and concentrations (as shown in FIG. 8). This equation also gives insight into the design considerations and trade-offs associated with different hydraulic system configurations. As an example, the addition of solid batteries to our hydraulically powered device would increase the total energy content of the device (while decreasing the fractional increase in energy from the electrolytic hydraulic fluid), but this would also greatly diminish the dexterity of our robot. A larger volume fraction devoted to solid battery structures would increase weight and decrease actuator amplitude (due to a reduction in hydraulic fluid). At a certain point, we would need to add additional structures to the robot to support the added weight of the solid batteries, which further results in sub-linear scaling of energy density. Using a larger volume fraction of electrolytic fluid, as we show in our work, allows for larger actuation amplitudes and more complicated locomotion maneuvers, without large increases to the weight of the device. However, the lower energy density of the electrolytic fluid, relative to solid lithium-ion batteries, also results in a reduced total energy content. Future applications of our synthetic vascular system should be informed by these design trade-offs.

Testing the Bending Stiffness of Liquid-Infused Battery Cells

FIG. 4C shows the bending stiffness data for a composite battery cell and its component materials. During these tests, catholyte was omitted from the battery cell due to the risk of damaging the electronics of the compression testing device in the event of a leak. The addition of an incompressible fluid to the test cells would likely increase the stiffness of those cells.

Figure 10:
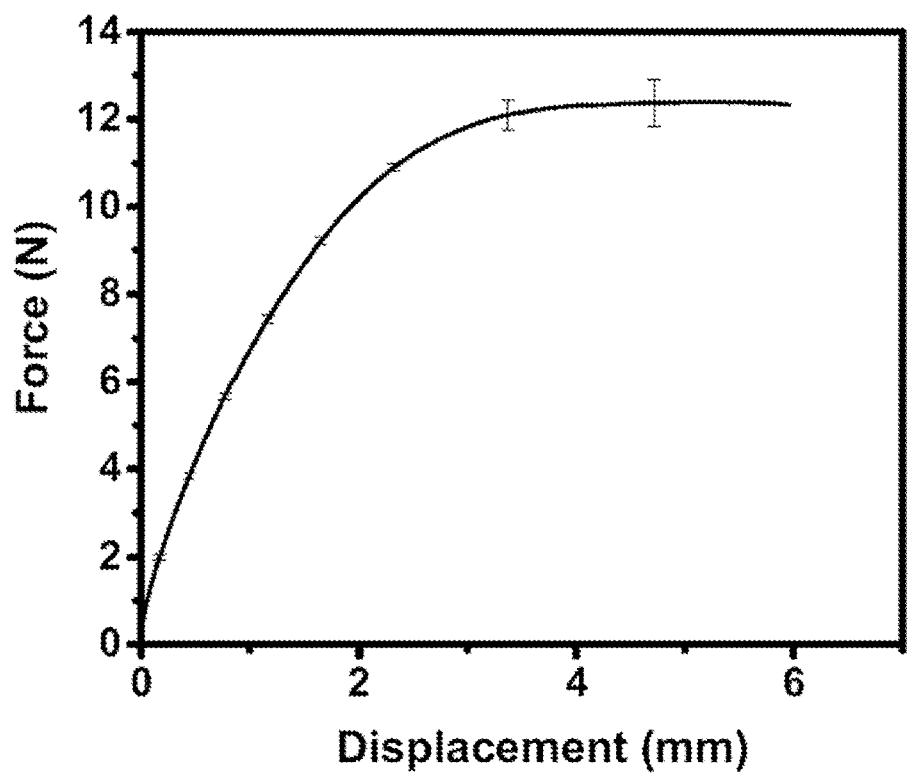
FIG. 10: Buckling test results for a fluid-filled battery actuator cell of the exemplary robot embodiment.

An additional buckling experiment was conducted with the results displayed in FIG. 10. In this experiment, an appropriate volume of water was injected into the battery test cells to simulate the presence of the $ZnI_2$ catholyte solution. When the cell was filled with water, a number of imperceptibly small leaks became visible at the edges of the composite cell, where the two silicone layers and the Nafion 115 membrane were previously attached with silicone epoxy. These leaks were sealed with a minimal amount of silicone epoxy which, upon drying, was stiffer than any individual element of the battery cell. This step was may be advantageous to ensure that no liquid escaped during the buckling tests (n=8), as this would have impacted the data and potentially damaged the testing device.

The average force F in buckling was determined to be 12.54 N, which gives a calculated bending stiffness value of 7.94 N $cm^2$. This presents a roughly 10% increase over the reported value of 7.17 N cm² for the composite cell without the added liquid. We observed that the flexible silicone (Dragonskin 20, Smooth-On) comprising the outer layer of the cells is capable of expanding to accommodate displaced fluid while maintaining the same internal volume during buckling. As a result, the encapsulated liquid does not dramatically increase the stiffness of the cells. We also believe that the added silicone epoxy contributed at least partially to the observed increase in the stiffness of the cells. Considering these associated measurement errors, we are unable to precisely quantify the increase in stiffness due to the presence of liquid in the battery cells, though we are confident that the stiffness likely increases with the addition of the liquid.

Example 2

Electrohydraulic Exoskeletons with Haptic Sensation Powered/Cooled by "Robot Blood"

Marines, warfighters, Navy divers, and those involved in search and rescue operations often encounter heavy objects that must be lifted, or may need to carry heavy gear over long distances. Such personnel would benefit from augmented force exoskeletons. Further, the gear they must wear (e.g., body armor, weaponry, survival equipment, etc.) creates increasing amounts of thermal barriers and makes cooling an issue for the wearer.

To compensate for the additional weight such personnel must carry, powered exoskeletons are becoming an increasingly important research area. Exoskeleton systems have the potential for force augmentation; however, existing machines are bulky, heavy, unintuitive to operate, and must be tethered or operate for only short durations when untethered. Recently, advancements in soft robotics make it possible to realize soft exoskeletons that can assist in locomotion and manipulation tasks without a hard and restrictive exosuit, and provide a platform for exploring how chemistry can improve the state of the art in exoskeletons.

In another aspect of the present disclosure, flow cell battery chemistry may be used as the working fluid in a hydraulically actuated exoskeleton. Such exoskeletons may provide benefits akin to blood in animals. The use of this fluid may improve the energy density of the system overall by forming a diffuse battery over a large portion (or the entirety) of the robot. In a version, the system includes a robotic circulatory system where the "blood" is actually the anolyte and/or the catholyte of the flow cell battery. The working fluid may also be used for thermal management of the system. While such systems have broad applicability to, for example, vehicles, robots, exoskeletons, etc., in the present example, the presently disclosed techniques are applied to an advanced exoskeleton that not only augments force, but may also monitor the health of the wearer, and sense details of the environment using optoelectronics. When unpowered, the suit may provide no more resistance to motion than would a typical wet suit.

The electro-hydraulically actuated exoskeletal system may allow an individual, such as, for example, a member of the military, to manipulate heavier objects or to compensate for increased difficulty in movement. The use of stretchable, optoelectronic sensing skins or other sensing technologies may allow feedback control during manipulation, and/or a detection system for impacts or damage to the individual. While certain anolytes and catholytes may have higher densities than more traditional hydraulic fluids, there may be no need for the additional weight of a typical on-board battery—yielding a weight savings in the total system. Through intelligent programming of the fluidic actuation, the artificial circulatory system can be used for thermal management with little extra energetic cost.

This example focuses on the materials, control methods, and systems integration necessary to implement a distributed flow cell battery that permeates the volume of an exoskeleton. In an example, of a sub-component of the whole exosuit is an upper body shoulder, glove, and sleeve combination.

The potential impact of this work is vast and includes, without limitation:
Higher energy density exoskeletons
Thermal management via robotic circulatory systems
Force augmentation for carrying greater loads or existing loads for longer duration
More maneuverable exoskeletons
Active sensing of the wearer's motion and suit's integrity for increased safety
Selective stiffening of areas of the suit to prevent injury (e.g., whiplash).
Fluid Powered Exoskeletons Previous exoskeletons are either electrically (e.g., Berkley Bionics' Ekso), hydraulically (e.g., Lockheed Martin's HULC), or passively (University of Twente's XPED 2) powered hard linkages that mimic the joints and bones in the human skeleton in certain locations. The more forceful of these systems are bulky and heavy, requiring a considerable amount of electrical energy when powered and, when unpowered, they severely limit motion and could be detrimental when used in close quarters. The presently-disclosed exoskeleton embodiment may be based on hydraulically-powered soft actuators. However, the example is intended to be non-limiting, and the principles demonstrated may be used with electrochemically active hydraulics in devices beyond soft robotics.

The first soft actuator, the McKibben artificial muscle, like a hydraulic exoskeleton, is powered by fluid pressurization. The McKibben has done a good job of simulating natural muscle; these devices are tubes wound with helical fibers that shorten upon internal pressurization. Some of its analogous properties to natural muscle are: increasing thickness during contraction, similar force versus length curves, and very large strength to weight ratios. They do not, however, match muscle in two important ways: (i) the force versus length relationship is non-parabolic and fails to approximate natural muscle when stretched beyond its resting length and, (ii) the artificial muscle's actuation velocity varies little with applied load, while natural muscle's speeds are only attained at zero loading. By using more complex architectures (e.g., variable recruitment), increasing the numbers of actuators, and matching the micromechanical properties of the synthetic materials to natural muscle, elastomeric fluid actuators may behave more intuitively. For example, previous work has shown that, to the first order, pairs of McKibben actuators could approximate the force-velocity profile of natural muscle. These McKibben actuators have previously been used for a foot-ankle prosthetic. When pressurized pneumatically, the actuator contracts ~25% of its initial length and uses soft strain sensors for feedback controlled torque during walking.

Figure 12A:
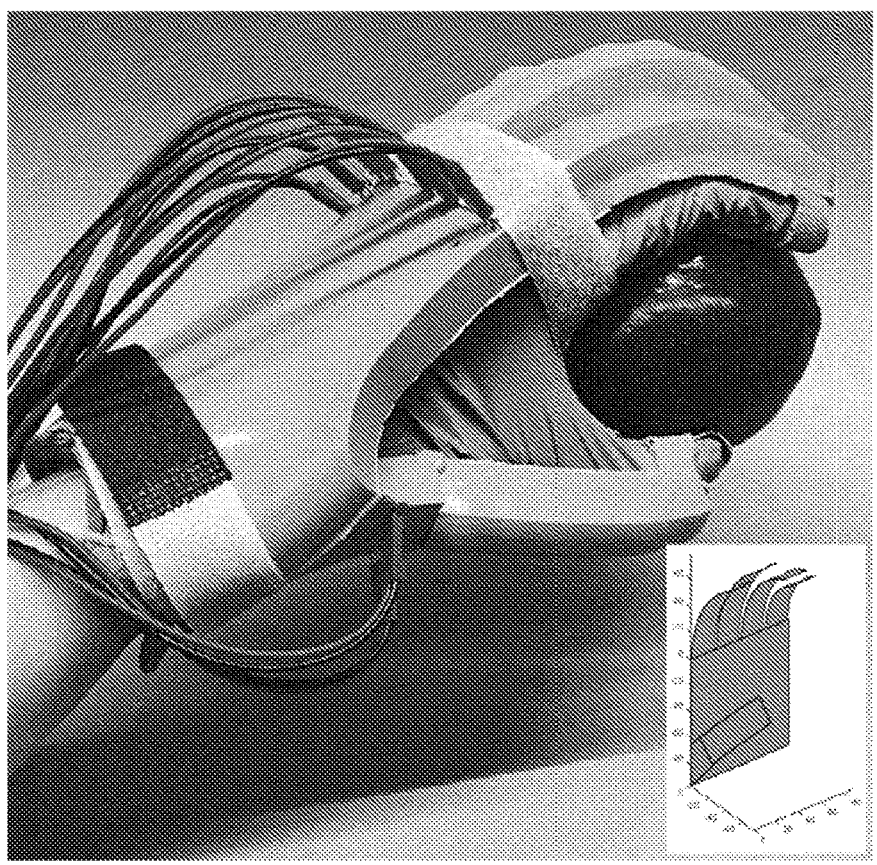
FIG. 12A: Fluidically powered orthotic glove
Figure 12B:
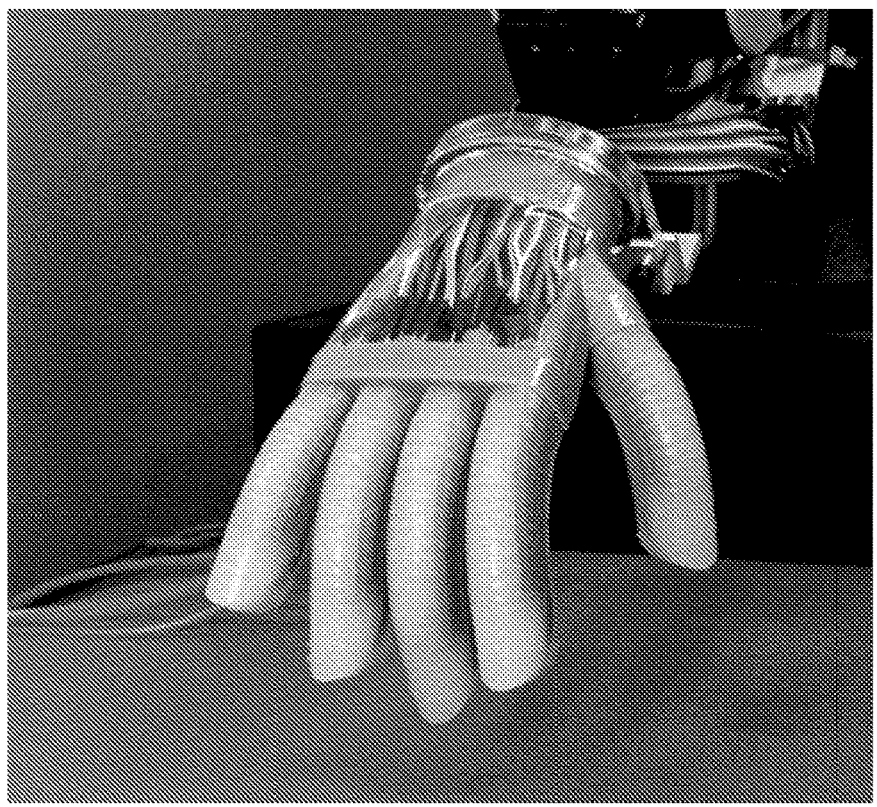
FIG. 12B: Prosthetic hand capable of haptic sensation.

In their present state, however, McKibben actuators are not a good choice for exoskeletons: they are currently pneumatically powered which has associated inefficiencies, their shape is non-conformal to the human body, and their actuation amplitudes (stroke) are low. The present exemplary exoskeleton may use chemically inert silicone actuators that are hydraulically powered; unlike McKibbens, the present fabrication method allows precision control over the actuators morphology, deformation modes, and design of antagonistic pairs. Importantly, the chemical inertness of the selected silicone rubbers may also be compatible with the anolyte and catholyte flow cell battery chemistry. Advanced soft robots have recently been produced for useful endeavors. For example, FIG. 12A shows an orthotic glove capable of augmenting force and FIG. 12B shows a prosthetic hand capable of haptic sensation. The actuators in FIGS. 12A and 12B use pressurized gas (5 psi; 35 kPa) to power morphological changes; as a result they are very soft and conformable at low applied stress. Recently, an industrial manufacturing technique, rotational casting, was adapted to produce soft actuators. Actuators produced using rotational casting are not glued together, but are a monolithic form, which results in no weak point for tearing during inflation. The technique can be used for many material types (e.g., polyurethane and styrene-butadiene compounds). The soft machines made using this technique can apply significant forces (>30 N), particularly useful for upper torso applications.

Thermal Management in Robotics

It is normal to cool electric motors via passive cooling (e.g., heat sinks) or actively via circulating coolant. Recently, an interesting method for cooling via perspiration has been introduced in humanoid robots. This robot uses laser sintered porous aluminum heat sinks to transport pressure driven coolant to the surface for evaporation. The use of circulating electrolyte as a coolant for thermal management could also be combined with a co-circulating fluid for perspiration and more efficient cooling in a similar manner. The use of soft robotics provides a unique opportunity for molding complex channel pathways to direct the circulating electrolyte from internal motors and pumps to surface layers for cooling and evaporation of a co-coolant.

Control in Exoskeletons

The very thing that makes these actuators useful, their high compliance, also makes them very difficult to control. Their interaction with the environment is complex and reliably predicting the shape of the actuator is not currently possible without external or internal sensing. We have used stretchable sensors to enable two things in soft actuators: (i) the shape of the actuators (kinesthetic sense) and (ii) force interactions with the environment (touch). These sensors are necessary for closing the loop in compliant robots without the use of external visualization. Though this example is not focused on sophisticated control of exoskeletons, we may demonstrate a functioning exoskeleton using the robotic blood concept that may require a minimum level of control.

Figure 13A:
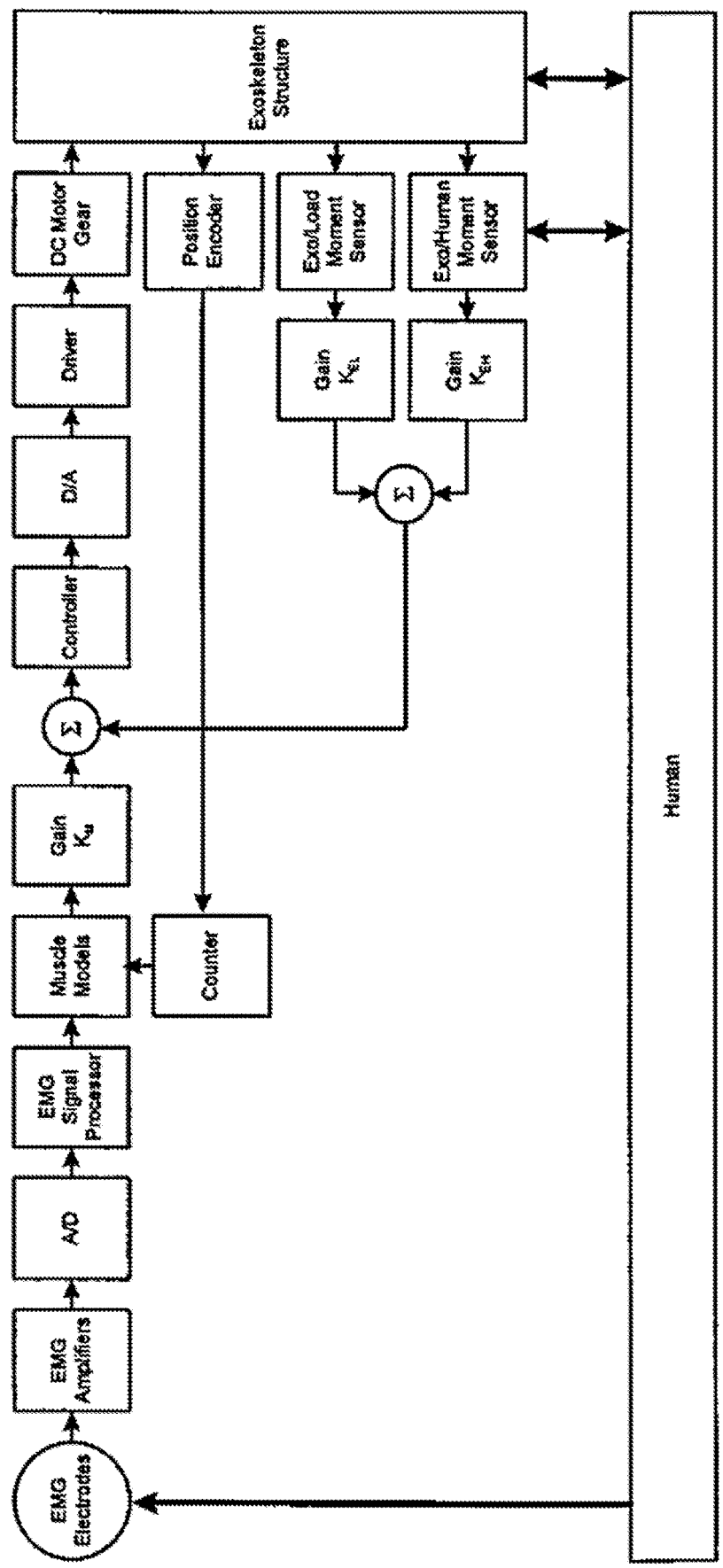
FIG. 13A: A diagram depicting an exemplary feedback control algorithm for EMG sensor—2 link, 2 joint actuator mechanism.

The actual input signals for controlling exoskeletons are myriad. Electromyography (EMG) sensors, however, have previously been used in concert with powered exoskeletons. EMGs detect electric impulses during muscle contraction; a big advantage of using them is the potential for natural integration with the wearer. For example, ideally, a patient with a missing hand could apply them to their forearm and attempt to squeeze the phantom hand; the EMGs would detect that signal and then cause a prosthetic hand to grasp. FIG. 13A describes an example where EMG signals are detected from arm muscle and sent through a "myoprocessor" that matches the motion of the exo-suit to that of the wearer using a conventional Hill-type muscle model. The arm of the exosuit moves to the expected position and uses an encoder to feed back the exact position to the muscle model and compensate when needed. All of the actuators and sensors used in this scenario were stiff and inextensible.

Technical Approach

Figure 14A:
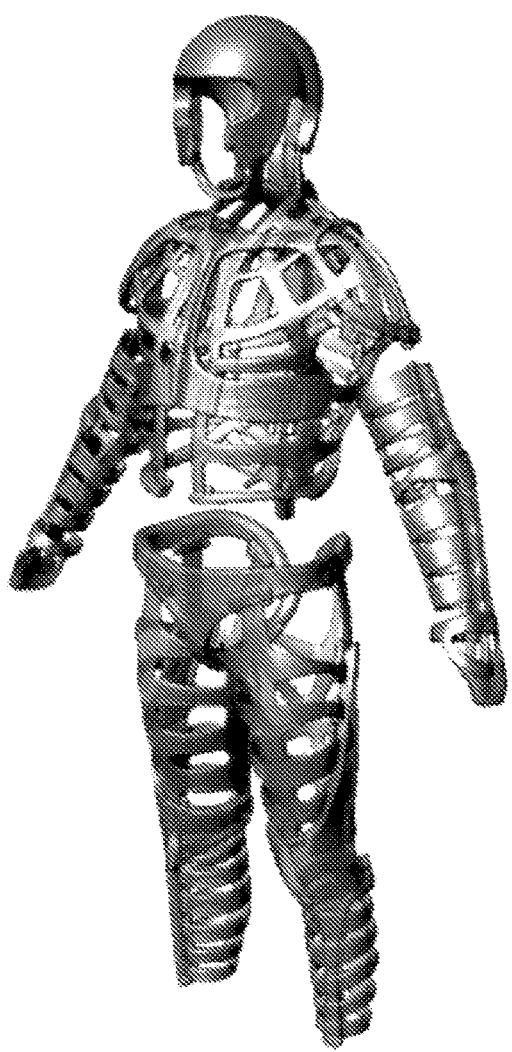
FIG. 14A: Conceptual soft exoskeleton with semi-solid fuel cell electrohydraulic fluid.
Figure 14B:
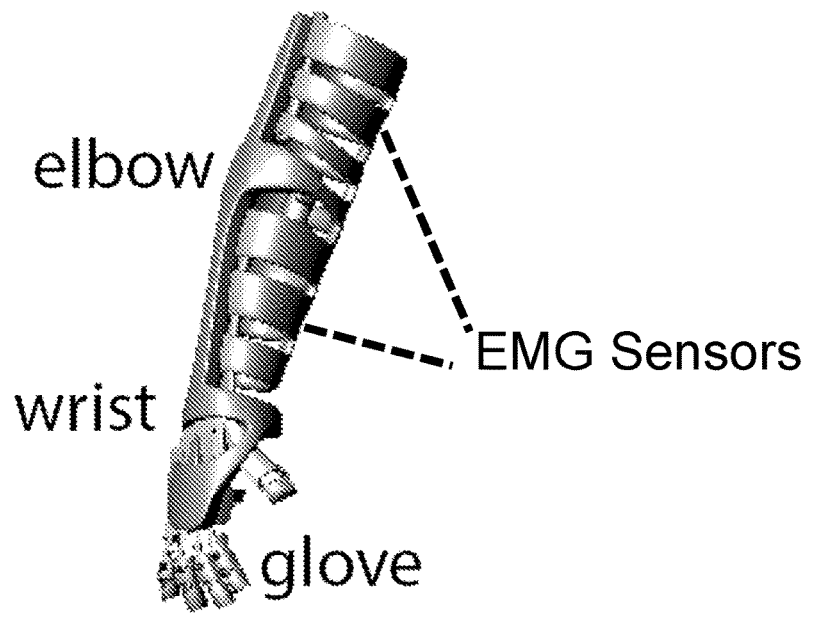
FIG. 14B: Exemplary embodiment of exo-sleeve (partial exoskeleton) and control inputs.

The goal of this example is to develop the chemistry and machinery for semi-solid fuel cell hydraulic fluid for robotics and exoskeletons. The high energy density of the system as well as an additional capability of perspiration thermal management may be demonstrated using a platform: soft robotics. The technology is expected to be broadly applicable to robots, vehicles, and other hydraulically powered exoskeletons. For the soft exoskeletal system, EMG inputs may be used to detect intent by the wearer and then use this signal to trigger hydraulic pressurization of soft actuators that maintain a curvature set by communication between embedded optoelectronic strain sensors. To demonstrate a diffuse battery system, we can:

(i) Develop a rheologically tuned suspension of lithium based SSFC anolyte and catholyte suitable for hydraulic actuation;

(ii) Concurrently, design a flow cell geometry capable of also actuation via hydraulics;

(iii) Form an upper extremity exoskeleton in the form of hand, wrist, and elbow sleeves (FIG. 14B); (iv) Demonstrate operation of the upper extremity exoskeleton using EMG control.

Robot Blood & SSFC Actuator

Figure 15B:
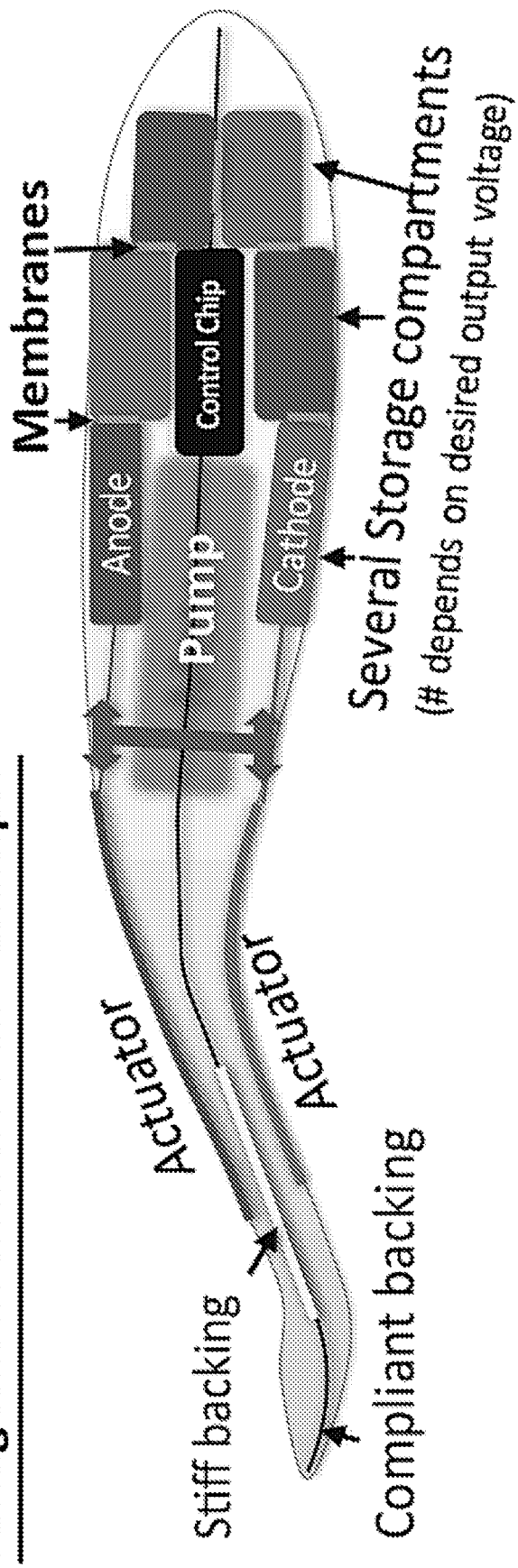
FIG. 15B: Schematic of hydraulically powered robot using electroactive suspension.

Electrohydraulic Actuators. The use of suspensions of active lithium ion compound (i.e., $LiCoO_2$—$Li_4Ti_5O_{12}$ and $LiCoO_2$-graphite as anolyte and catholyte) with percolating networks of conductive particle fillers may form the basis of an electroactive hydraulic fluid according to an exemplary embodiment. These materials may be pumped to the reservoirs of a redox flow cell that may be configured as hydraulic actuators (FIG. 15A, right). A schematic example of building a robot using this concept (a robotic fish), is shown in FIG. 15B. This example robot demonstrates hydraulic actuation of antagonistic actuator pairs which may be a core component of any exoskeletal system.

Figure 16A:
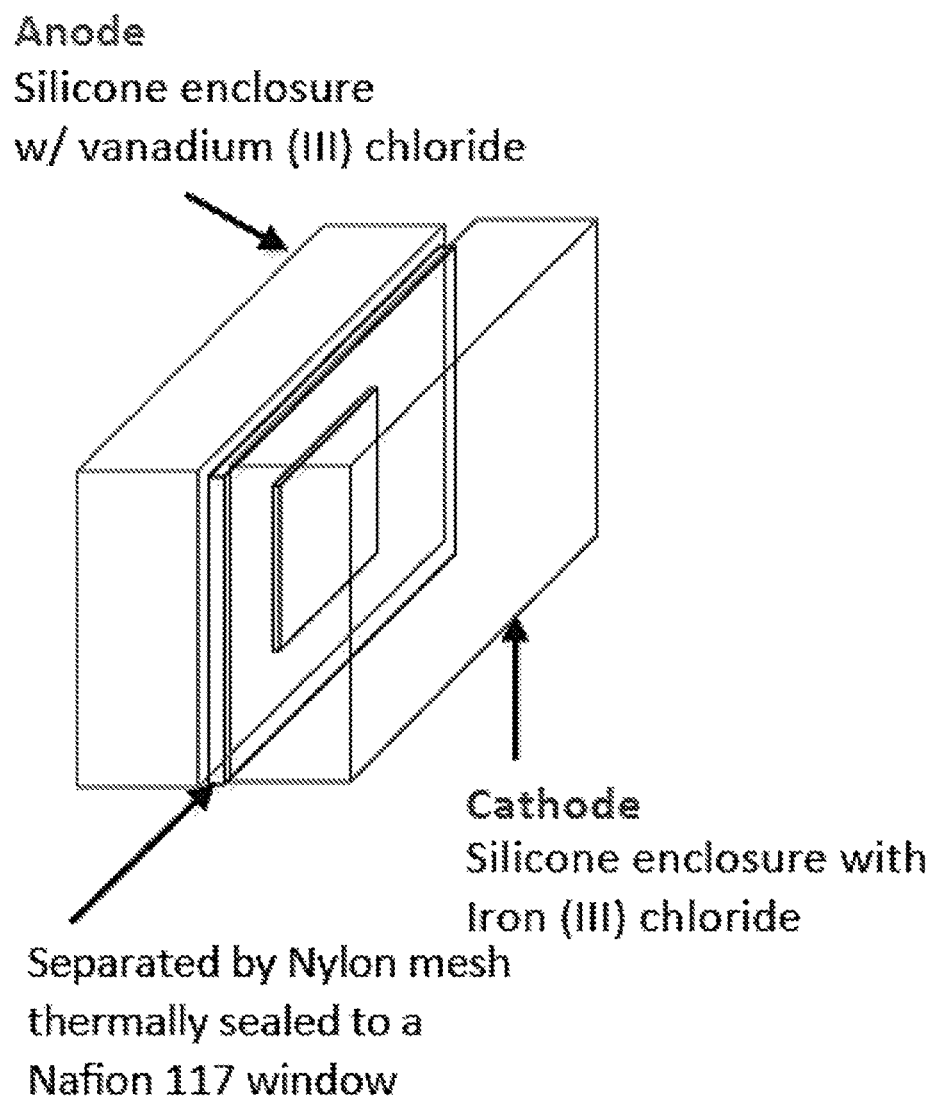
FIG. 16A: Schematic of electrohydraulic actuator cell.
Figure 16B:
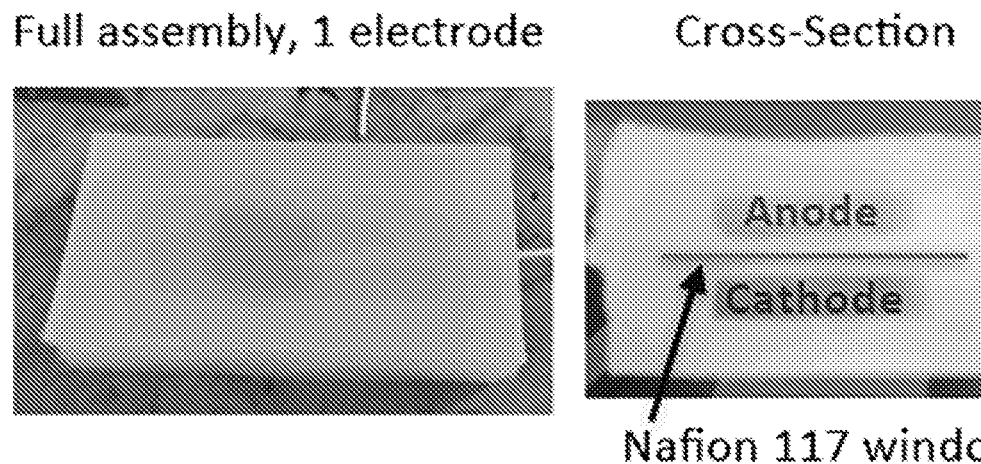
FIG. 16B: Vanadium (III) chloride anolyte and iron (III) chloride catholyte with a cation exchange separator membrane of the cell of FIG. 16A.
Figure 16C:
FIG. 16C: The cell measured 0.4 V during discharge.

FIGS. 16A-16C show preliminary data of a test embodiment using less sophisticated and energy dense anolyte and catholyte chemistry, vanadium (III) chloride and iron (III) chloride. This chemistry is encapsulated in a silicone actuator. The electric potential measured from this soft cell, 0.4 V, is not large but does indicate the circuit is functioning and the chemistry is compatible with the elastomeric actuators; the system was stable over the several days of the experiment, with no degradation in performance.

Actuation

In order to apply this system to a fully functional exoskeleton, hydraulically powered soft actuators may be used. Such actuators may be fabricated using a rotational casting technique developed for applying previously high force, and using a 3D printing technique we have pioneered for direct printing of elastomeric actuators. The forces produced by the silicone and polyurethane based pneumatic actuators we have already fabricated are sufficient for significantly enhancing the gripping force of an operator as well as reducing the metabolic cost to the wearer for routine tasks (FIG. 12A).

Figure 17A:
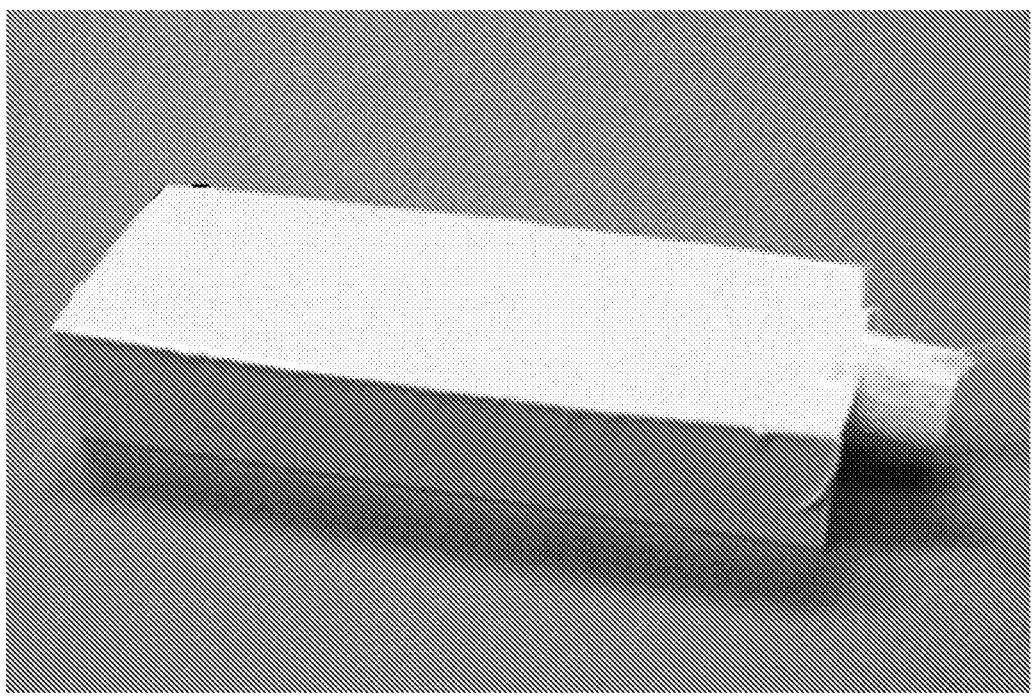
FIG. 17A: A rotocast actuator in an non-actuated state.
Figure 17B:
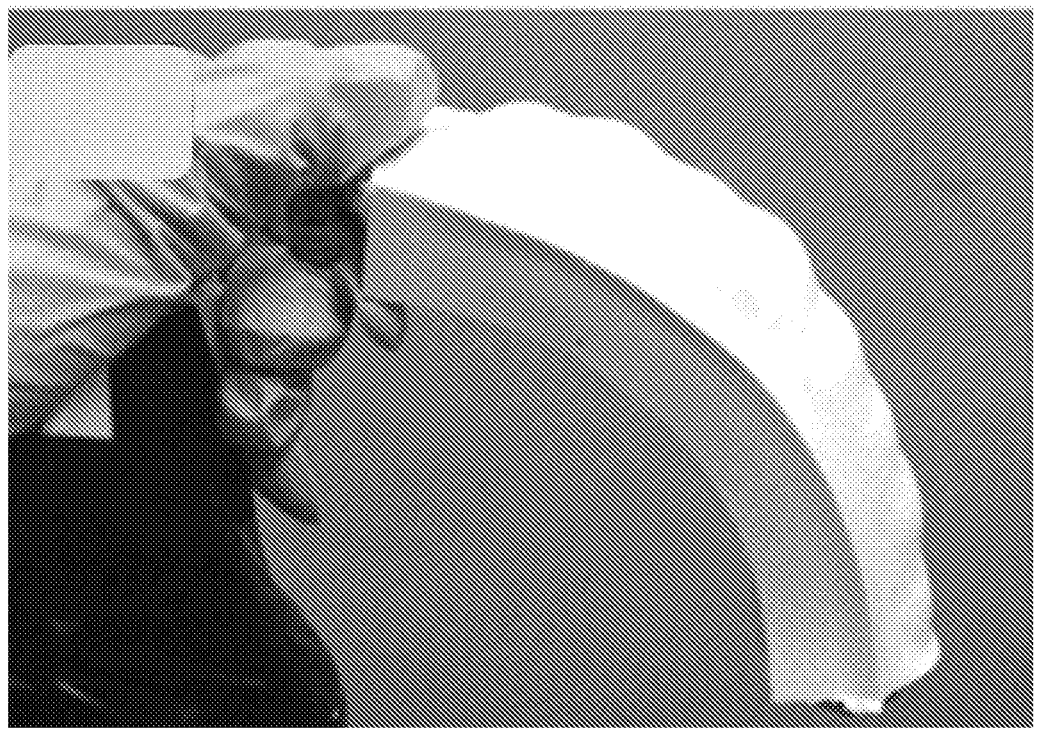
FIG. 17B: The actuator of FIG. 17A in an actuated state.
Figure 18A:
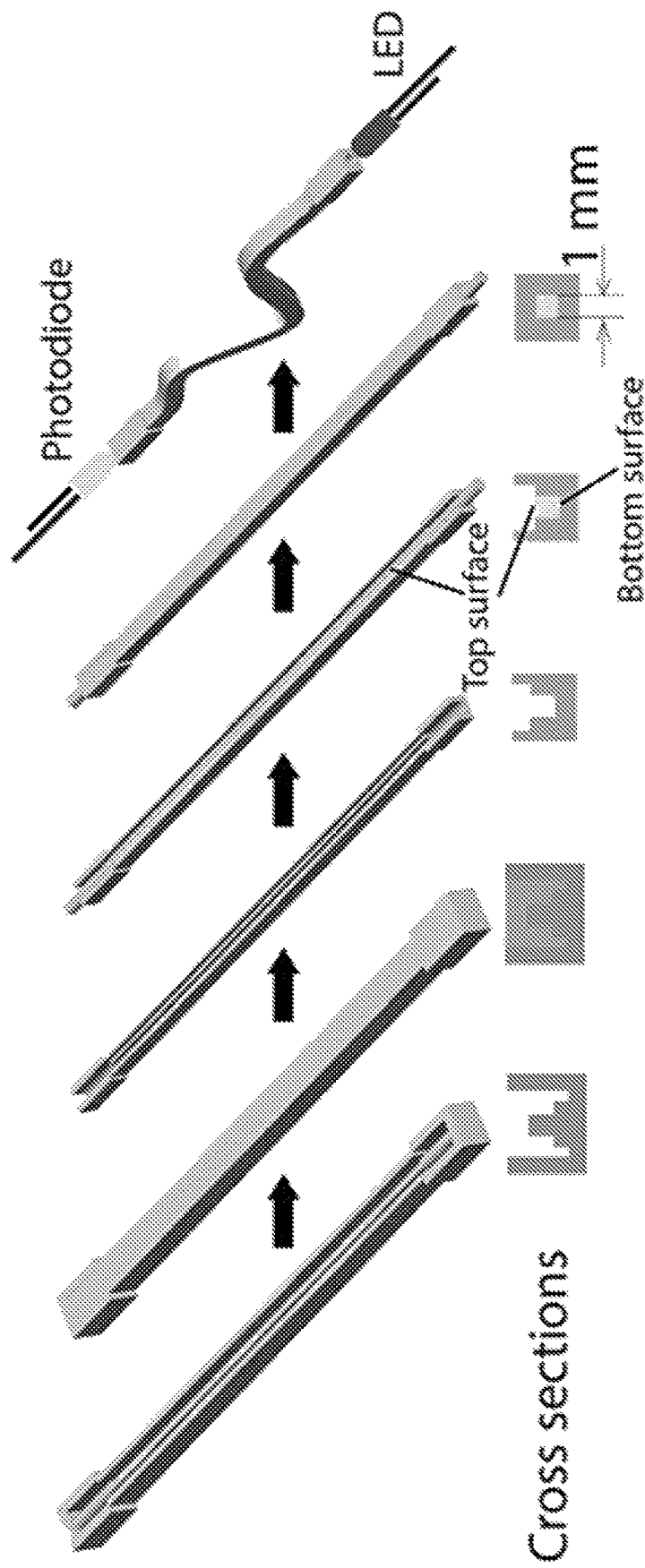
FIG. 18A: Steps for fabricating a waveguide and the corresponding cross section for each step.
Figure 18B:
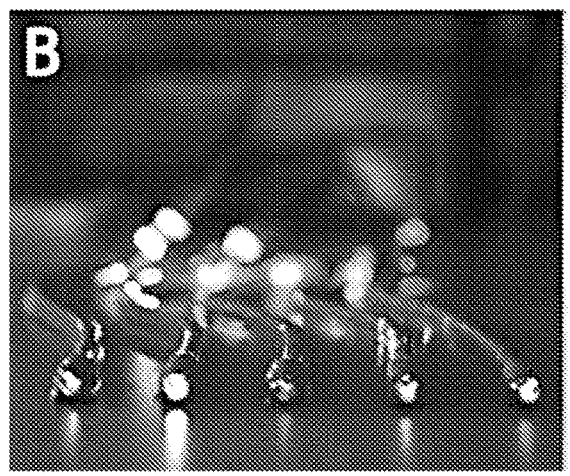
FIG. 18B: Fabricated waveguides with assorted color LEDs inserted from one end in a sinuous shape.
Figure 18C:
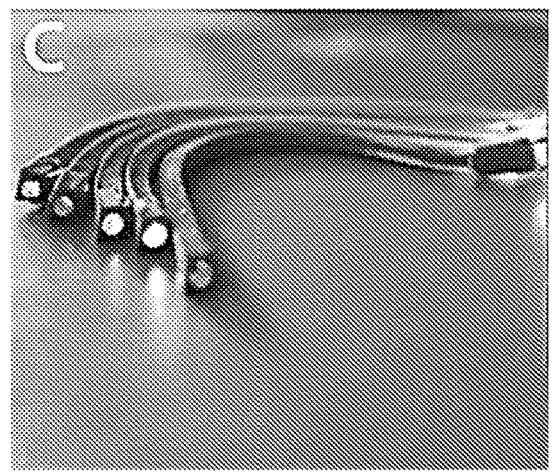
FIG. 18C: Waveguides in a curved shape.
Figure 18D:
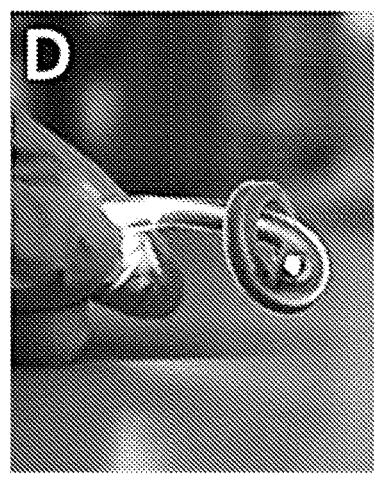
FIG. 18D: Waveguide in a knot.
Figure 18E:
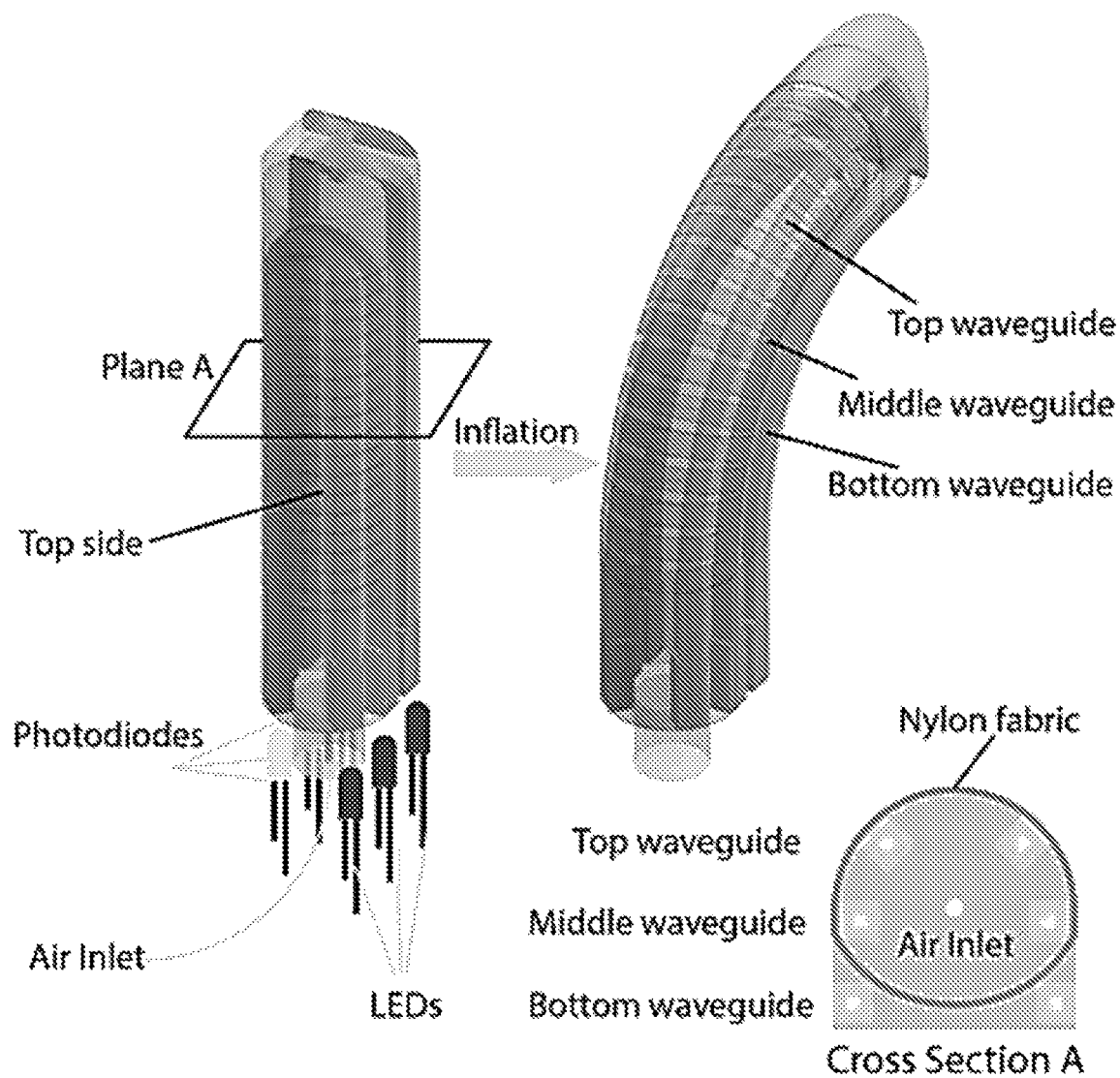
FIG. 18E: Schematic of a soft innervated finger.

These actuators are essentially high strength balloons that operate through a simple principle of anisotropic stretching during internal pressurization. They can be programmed to cause the actuators to change into nearly any motif, such as extension, contraction, or bending (FIGS. 17A and 17B). Whether pneumatic or hydraulic fluid is used for this pressurization, the principle is the same. FIGS. 17A and 17B shows the hydraulic pressurization of a polyurethane bending actuator using a pump. Note, however, that in our exoskeleton, we may also use electrically powered linear motors (or other means) to pressurize the hydraulic fluid. The inert hydraulic liquid which operated these soft actuators can be replaced with active lithium ion suspensions like the black fluid shown in FIG. 11B for in embodiments of the present exoskeleton.

Sensing. To maintain the appropriate curvature state of the actuators, it may be desirable to continuously measure their shape and internal pressure state, as well as monitor for contact from the environment. To achieve this task, we may use two types of sensors: (1) off the shelf piezo-resistive pressure gauges in line with the actuators, and (2) optoelectronic based on optical losses during deformation. The new strain sensors will provide information about the curvature of the actuators and environmental contact forces.

Figure 19A:
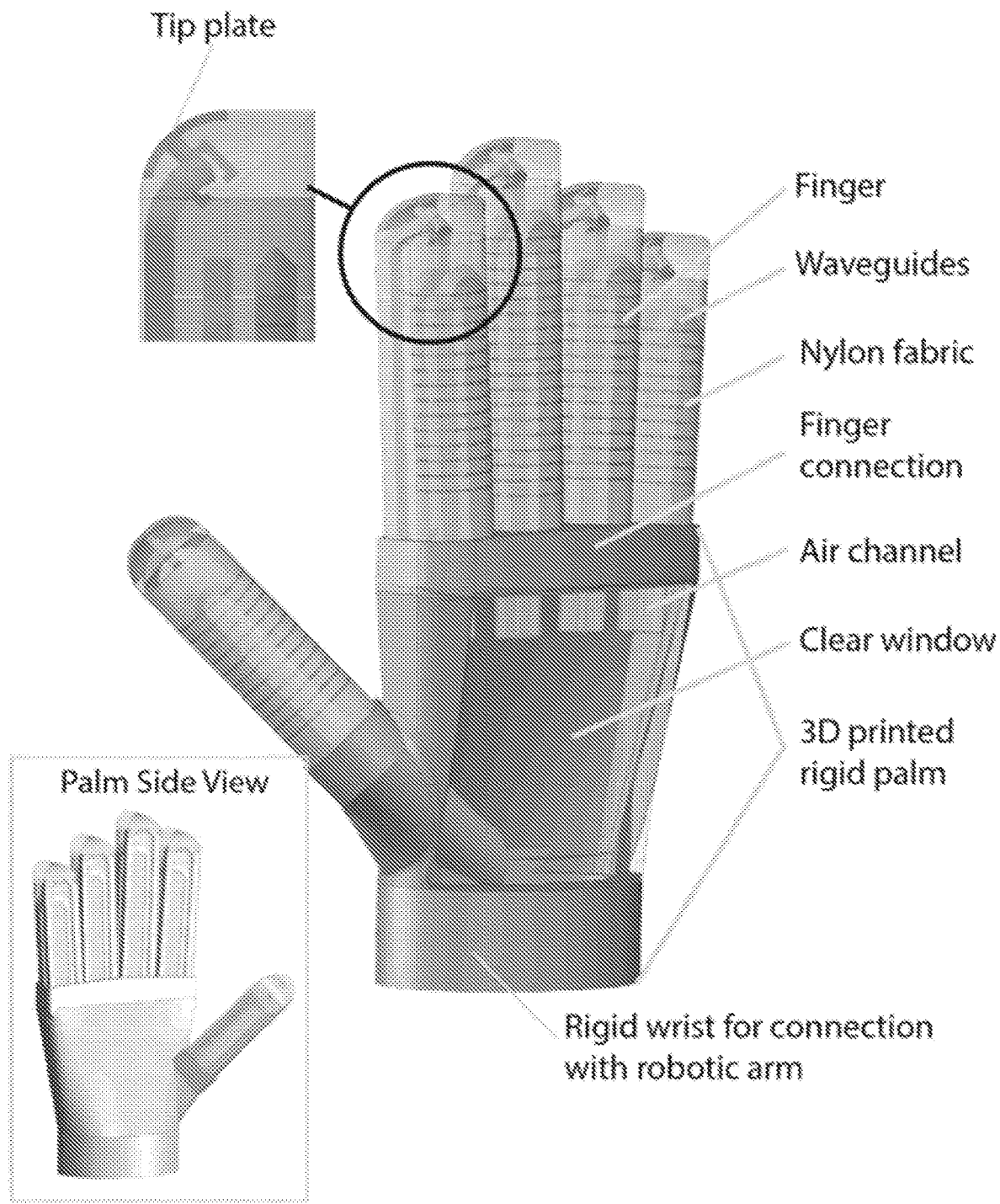
FIG. 19A: Schematic of an innervated prosthetic hand structure and components.
Figure 19B:
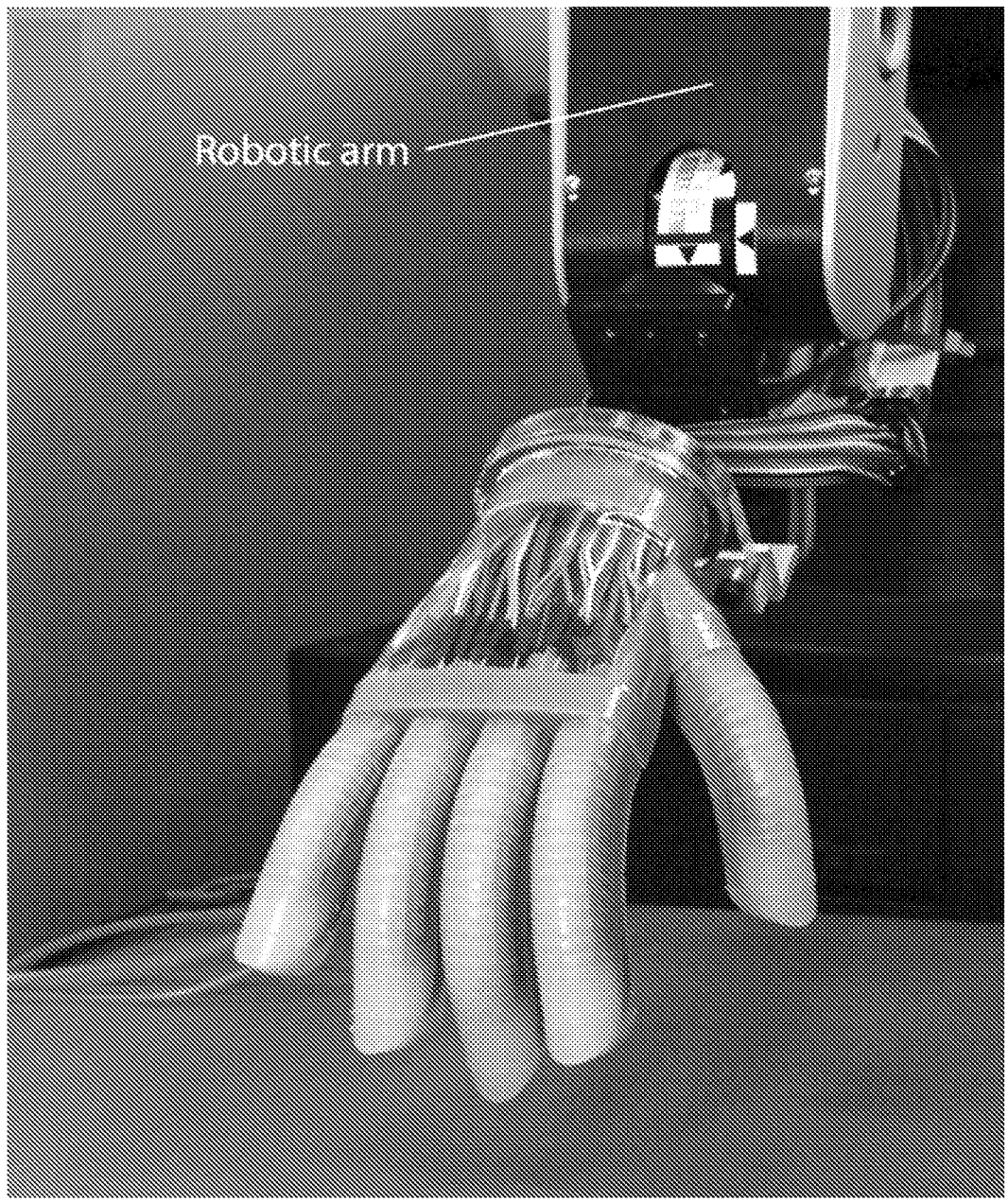
FIG. 19B: An image of the fabricated hand of FIG. 19A mounted on robotic arm with each finger actuated at $\Delta PP=100$ kPa.
Figure 20:
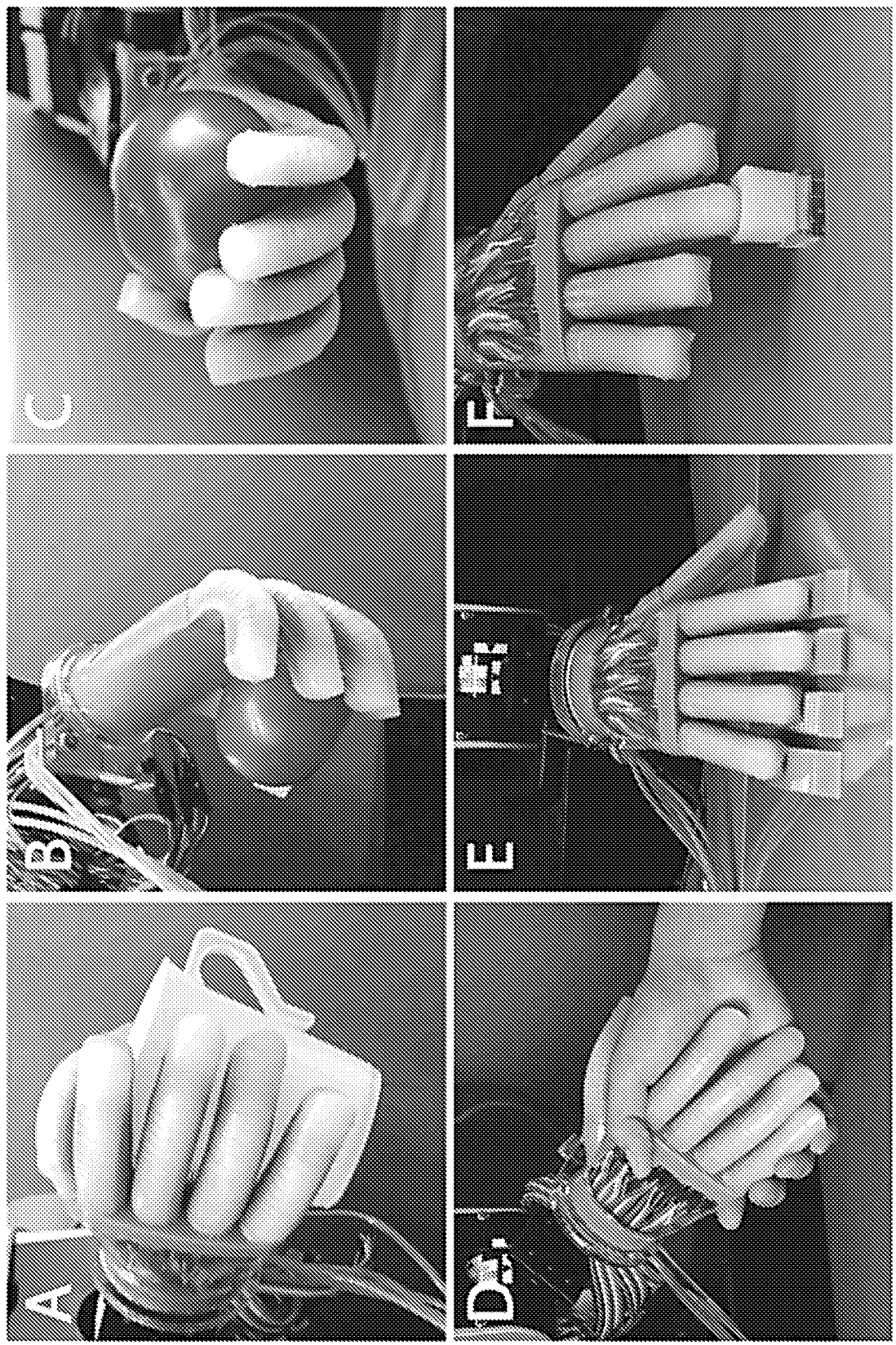
FIG. 20: Capabilities of the hand. (A) Holding a coffee mug; (B) grasping a tomato with the palm facing down and (C) palm facing up; (D) shaking a human hand; (E) lateral scanning over surfaces to detect roughness and shape; and (F) probing the softness of a soft sponge using the middle finger.

These sensors are stretchable optical waveguides. By pumping light into the waveguide and detecting the power output using photodiodes, it is possible to measure the change in transmission during deformation. This output is highly repeatable and relatively insensitive to environmental conditions. FIGS. 18A-18E demonstrate how stretchable waveguides can be integrated into the proposed exoskeleton to measure both (i) external forces (e.g., those experienced when grasping an object or unexpected ones from ballistic impact) and (ii) internal forces that shape the actuators. We have already integrated these sensors into a prosthetic hand (FIGS. 19A and 19B) to manipulate a variety of objects (FIG. 20).

Figure 21A:
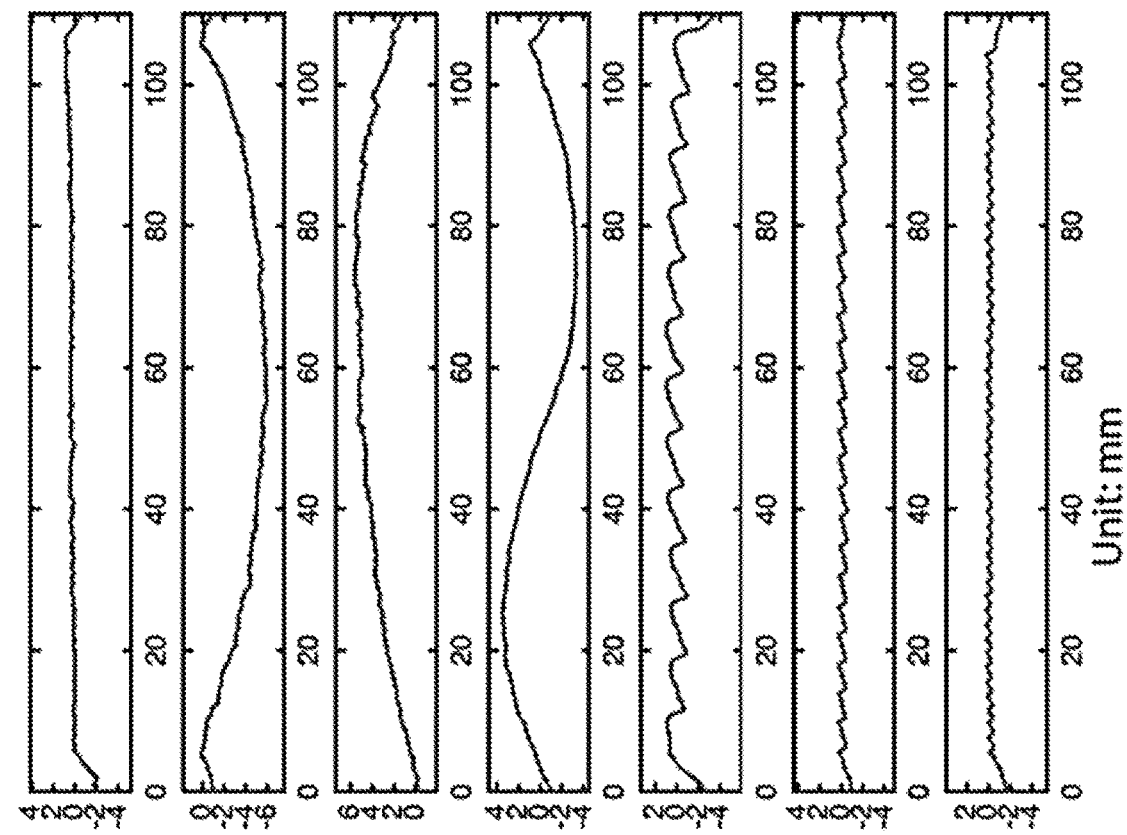
FIG. 21: Shape and texture detection. (A) (left) Seven surfaces of different shape and roughness and (right) the reconstructed surfaces by the hand; (B) picture of the lateral scanning for (A); (C) lateral scanning of a computer mouse; (D) mouse and the reconstructed shape.
Figures 21B, 21C, 21D:
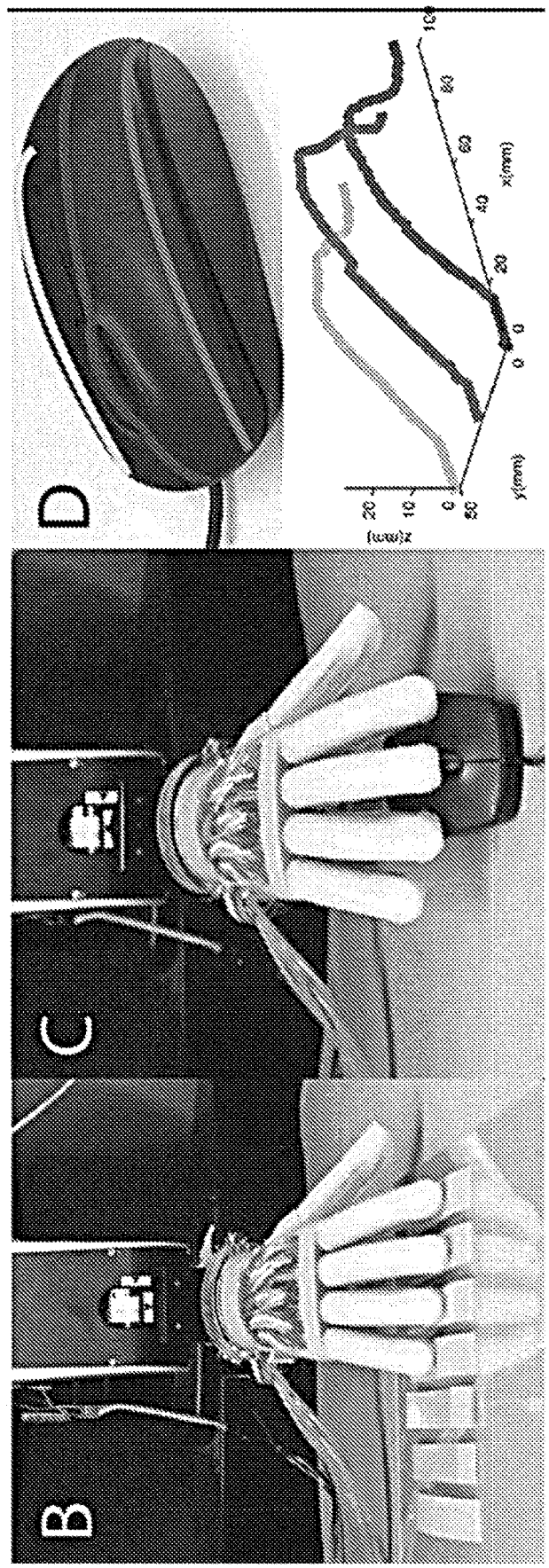

These sensors can be made from the same material as the actuators themselves, and can be integrated in complex, three dimensional motifs. In some embodiments of an exoskeleton, such sensors may be used to perform positional control. In some embodiments, such sensors may be used to sense contact forces with the environment and monitor for damage to the exoskeleton and, potentially, the human wearing it. As an example of the capabilities of such integrated sensors integrated into the actuator, the exemplary hand embodiments was used to measure the roughness and shape of different objects (FIG. 21).

Figure 13B:
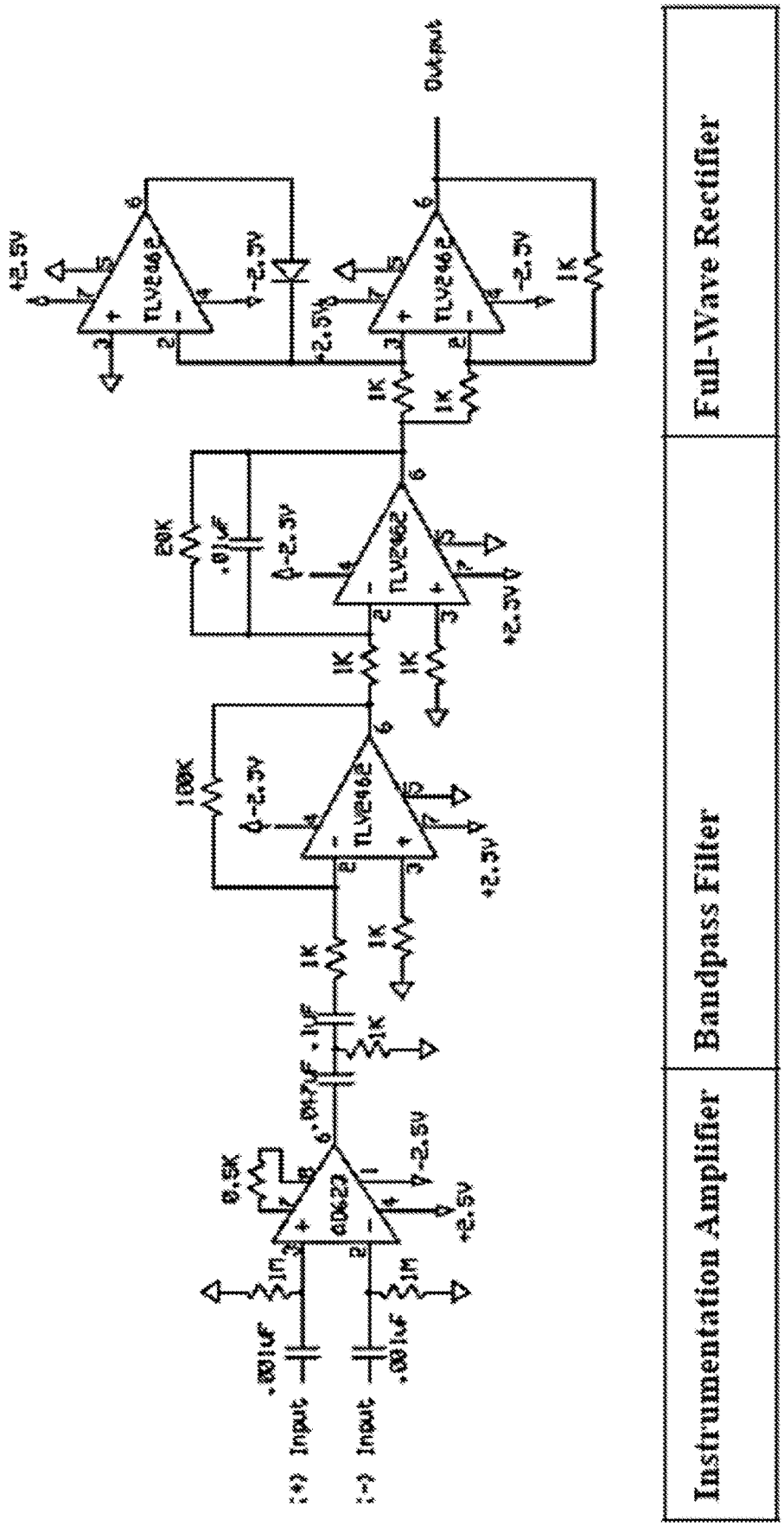
FIG. 13B: A schematic of an exemplary analog EMG Circuit.

While we may use the optoelectronic sensors as an input for proportional position control, we may primarily use electromyographic signals from muscle pairs to move the exoskeleton. Force, duration, and speed of actuation may be determined by comparing the EMG signals of muscular antagonist pairs (e.g., biceps and triceps for flexion/extension at the elbow). An exemplary EMG sensing system included 11 sensor channels, a ground electrode, and an Arduino Mega 2560 microcontroller. Each EMG sensor channel of the exemplary embodiment included two electrodes, placed at strategic locations along the arm, as well as amplification and filtering circuitry (FIG. 13B). The placement of each sensor channel may correspond to a specific movement of the exosuit (FIG. 22). The microcontroller may provide further processing and analysis of the amplified EMG signals to calculate the strength and duration of muscle contractions measured in each of the 11 channels. The stretchable waveguides incorporated into the exosuit's body may provide feedback control of shape and orientation of the actuators for user safety and motion smoothing. Feedback control software may be used to process and analyze data from the EMG and strain sensors and provide control signals to the pumps and other components.

Figure 23:
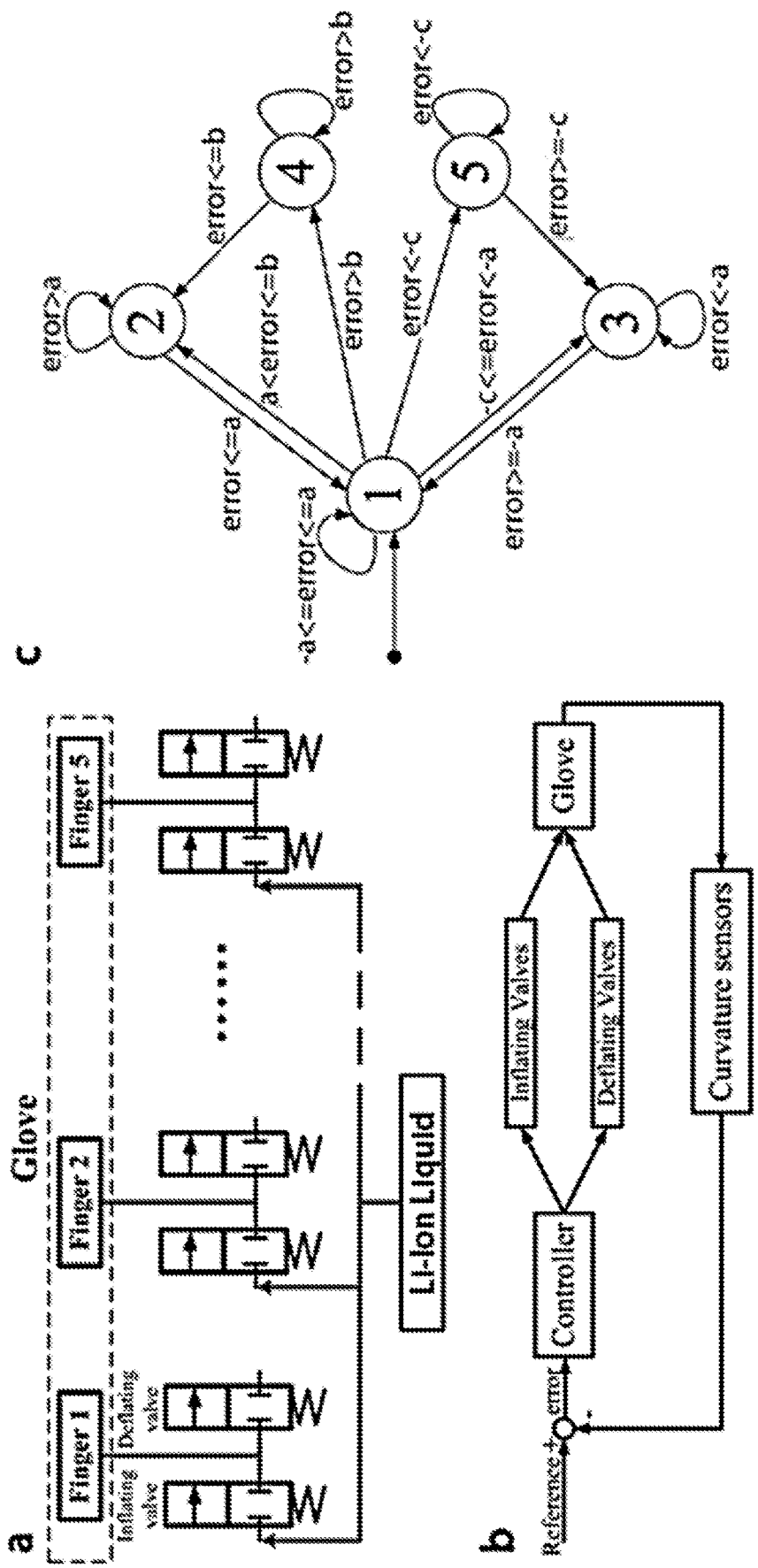
FIG. 23: Control system: (a) diagram shows how each finger is connected to valves and how the valves are connected to the lithiated electrolyte; (b) block diagram of the control system; (c) the controller is represented by a state machine.

Controller. An example of a control system is represented by the state machine shown in FIG. 23 which controls a 3-position valve (in, hold, and out), using two 2-position valves for each finger. For this controller, we simply control the valve position. The control is essentially non-linear and based on simple logic: liquid flows in if there is a desire to increase curvature, liquid is let out if there is a desire to decrease curvature, and if the curvature is close to the target pressure, the flow is stopped. To accomplish this control, we used two 2-way normally-closed valves for each finger (FIG. 23a). The inflating valve connects the electrohydraulic fluid source with the actuator and the deflating valve connects it to the SSFC reservoir. When the inflating valve is open and deflating valve is closed, the anolyte or catholyte goes from the reservoir to the actuator. When the inflating valve is closed and the deflating valve is open, the Robot Blood goes from the actuator to a reservoir or another actuator. When both are closed, the blood stays inside the actuator.

The block diagram of the controller is shown in FIG. 23b. Intuitively, a bang-bang controller should satisfy our requirements; however, due to the time delay of the output (curvature) to input (amount of liquid entering into the actuator) coming from both the viscoelastic properties of the material and the flow rate limit through channels, a bang-bang controller may cause oscillation. To overcome this issue, we have designed a new controller based on state machine shown in FIGS. 23c and 24. Specifically, we added a transition state from fully open and fully closed, where inflating and deflating valves may open and then wait to let the actuator reach its equilibrium state. The accuracy of system affects stability. Increasing b/c (FIG. 23c) may increase stability but decrease the time to achieve the desired curvature. This controller is not sensitive to the change of the pressure or actuator property. If the target reference signal stays constant, no extra anolyte or catholyte is required to maintain that value.

Evaluating Effectiveness of the Upper Extremity Exosuit Using Robot Blood

Figure 25:
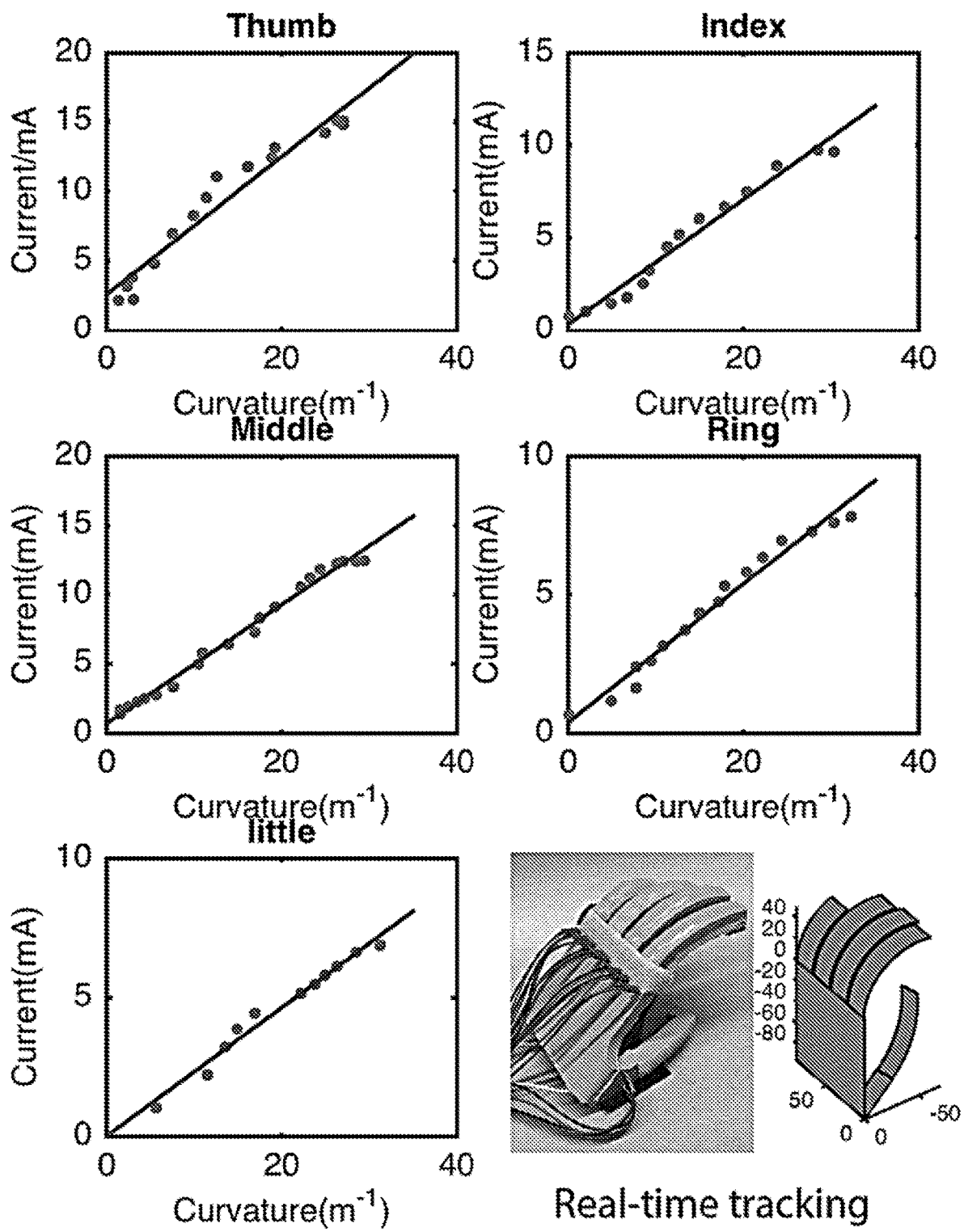
FIG. 25: Force test by wearing the glove: First, the user wearing the soft orthosis press the hand exerciser using his own effort until the force reached 60%; Next inflate the actuator and deflate the actuator twice while the user still hold the exerciser using a constant effort; finally, the user himself press the hand exerciser until it reached the same amount of force generated by the orthosis. During the whole process, force and EMG intensity are recorded.

To quantify the effectiveness of the soft exosuit in aiding upper extremity motion, EMG activity in the selected muscles may be compared with and without the exosuit. Preliminary tests were performed using low cost EMG sensors and an exemplary glove prototype. A healthy user wore the glove and tried to press a hand exerciser as shown in FIG. 25. On each button of the hand exerciser, a force sensor (FlexiForce A301 Sensor from Tekscan) was attached to record the force exerted on it. At the same time, the user wore a Myo armband, a retail EMG array, on the forearm to record his/her own effort of pushing each finger on the exercise device.

First, the user pressed the four buttons to 60% of the maximum normalized force, and then the orthosis was activated to help the user reach 100% force. An increased force from 60% to 100% was measured immediately and then dropped down to 80%. The orthosis was then deactivated and it was observed that force dropped down to 0% immediately, and then went back to 60%. The same process was replicated and similar results were observed. Finally, the user was allowed to press the buttons to reach 100% force using their own effort.

From these experiments, it could be seen that the actuator generates a big force impulse when activated and deactivated and then reaches equilibrium states. During the periods that the user just held the exerciser to reach 60% force, and the orthosis was helping to gain force change, the EMG intensity stayed constant. During the period that the user pressed the button, an increase of the EMG intensity was recorded. This experiment demonstrates the soft orthosis aids the wearer.

Figure 26A:
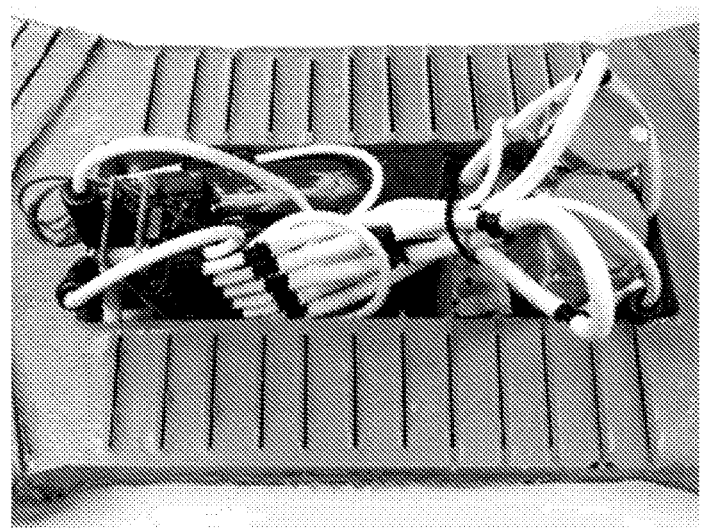
FIG. 26A: A control unit of an untethered quadruped robot, 0.7 m in length.
Figure 26B:
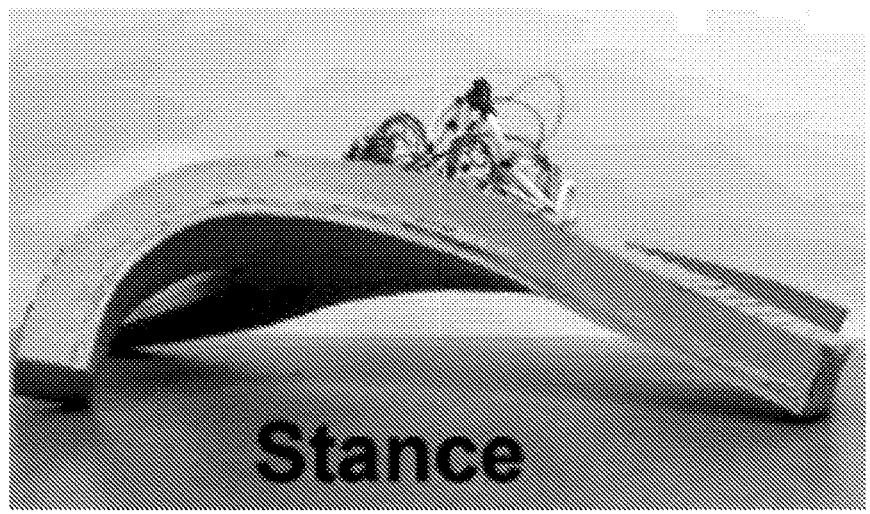
FIG. 26B: The quadruped robot of FIG. 26A in a walking position.
Figure 26C:
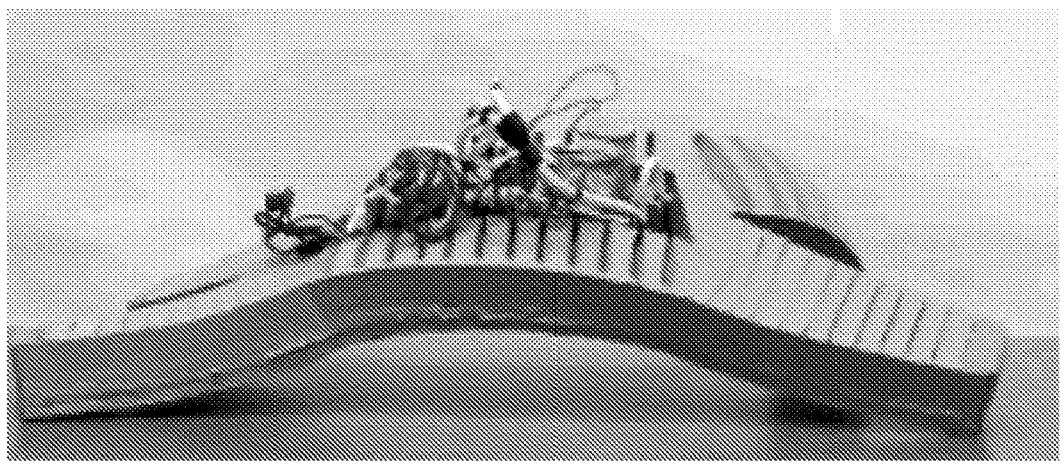
FIG. 26C: The quadruped robot of FIGS. 26A and 26B in another walking position.

Power strategy for exosuit. Recently, an untethered quadrupedal robot was developed (FIGS. 26A-26C). This robot uses two mini-air compressors powered by a lithium polymer battery (3,200 mAh) and controlled by an Arduino board to perform open-loop tasks autonomously. The robot is ~1 meter in length and can carry its weight (~3 kg) and that of its on-board components (~1 kg) using compressed air, 139 kPa (20 psi), to power six different soft actuators. These pressures were necessary to lift the robot's 4 kg against gravity and allow it to undulate (or walk). The robot can also carry an additional 8.0 kg of payload. These actuators may perform even better underwater, where their low density ($\rho$~1.1 $g^{-1}$) is primarily supported by the surrounding seawater ($p$~1.$g^{-1}$).

Powering these exosuits using hydraulics instead of pneumatics may allow for unlimited actuating fluid (using the surrounding ocean water). Both tethered and untethered versions of these exosuits may be developed. Tethered versions may not have limitations on power; however, the untethered versions may require battery packs that can operate a pump. For example, a non-limiting example of a suitable diaphragm pump can move liquid at ~3 L min-1 at ~345 kPa (~30 psi) and weighs only ~0.5 kg. It operates at 12 V and 4 amps (max draw); this pump should therefore allow for temporary assistance off of several LiPo batteries (5,000 mAh, 11.1 V from Mystcry, Inc.) Other pumps may be used, for example, more efficient pumps.

Future Naval Relevance via Historical and Notional Examples. Saipan 1944 and Pearl Harbor 1941. In 1945, a newly created Underwater Demolition Team (UDT) was used to clear the beaches of Saipan for a US invasion. These UDTs were composed of bomb disposal experts and Seabees for removing obstacles off of beaches in France. During the Saipan mission, UDTs cleared 1,200 underwater obstacles in 2 days—under heavy fire. Though many techniques were used by these teams (explosive ordnance for example), the availability of underwater exoskeletons to assist in movement, lifting, and improving safety would have been very helpful. In an imagined scenario, based on UDT operations in Saipan, the ability to adjust the thermal insulation of drysuits would allow members of these teams, and specialists today, to perform near-shore amphibious operations. A diver could adjust their dry suits to have excellent thermal insulation under water for obstacle disposal, and then emerge onto shore and collapse pores in the suits skin—eliminating its insulative properties and allowing the sailor to operate on land. The amphibious capability would eliminate the need for divers to carry extra clothing and supplies.

At 0755 on the morning of Dec. 7, 1941, Pearl Harbor was raided and many US Navy vessels (particularly battleships) were sunk. At 0915, salvage teams were cutting through the hull of the USS Oklahoma to rescue trapped sailors and recover ammunition and magazines.

Though diving technology has greatly improved since WWII, the needs presented by these historical precedents remain. The ability for divers to use greater force than their own bodies can supply to rescue shipmates or recover critical items, without waiting for the wreckage to be raised or specialized equipment to be brought in can save lives and reduce response times to unexpected circumstances.

In another imagined scenario, based on the USS Oklahoma, a fully integrated sensor and actuator network in a soft exo-divesuit would engage an undulatory swimming sequence that maintains a rescue diver's position while they use a Sea-Torch to cut through a sunken ship hull. The hull area the diver removes reveals a pocket of air from which trapped sailors are breathing. The diver grabs onto two of these trapped sailors with augmented force gripping gloves and sleeves, and the undulatory swimming sequence of his legs start kicking at larger amplitudes—allowing the rescue diver to swim the two people to the surface.

Operational Naval Concept. Using fabrication processes such as those discussed above, both the soft actuators and sensors can be co-integrated into a single form. These actuators change shape significantly, allowing for small form factors when unpowered, allowing freedom of motion by the wearer with limited fouling and entrapment danger. When powered, the form factor may increase; however, we may determine the best placement of the actuators to have minimal effect on the diver's performance. The change in shape may also be used to autofit a divesuit specifically to the wearer's comfort and insulation desire.

This example provides the basic science and engineering parameters to build exosuits that, primarily, augment the force of divers for salvage and rescue operations. These same principles can be used to selectively stiffen the exosuit for protection against increased hydrostatic pressure upon deep dives or to protect the diver against sudden trauma like whiplash (e.g., inflatable neck braces). The hydraulically powered, lightweight, and strong artificial muscles may not hinder the diver's freedom of motion when unpowered and still allow infinite passive degrees of freedom while powered.

Figure 27:
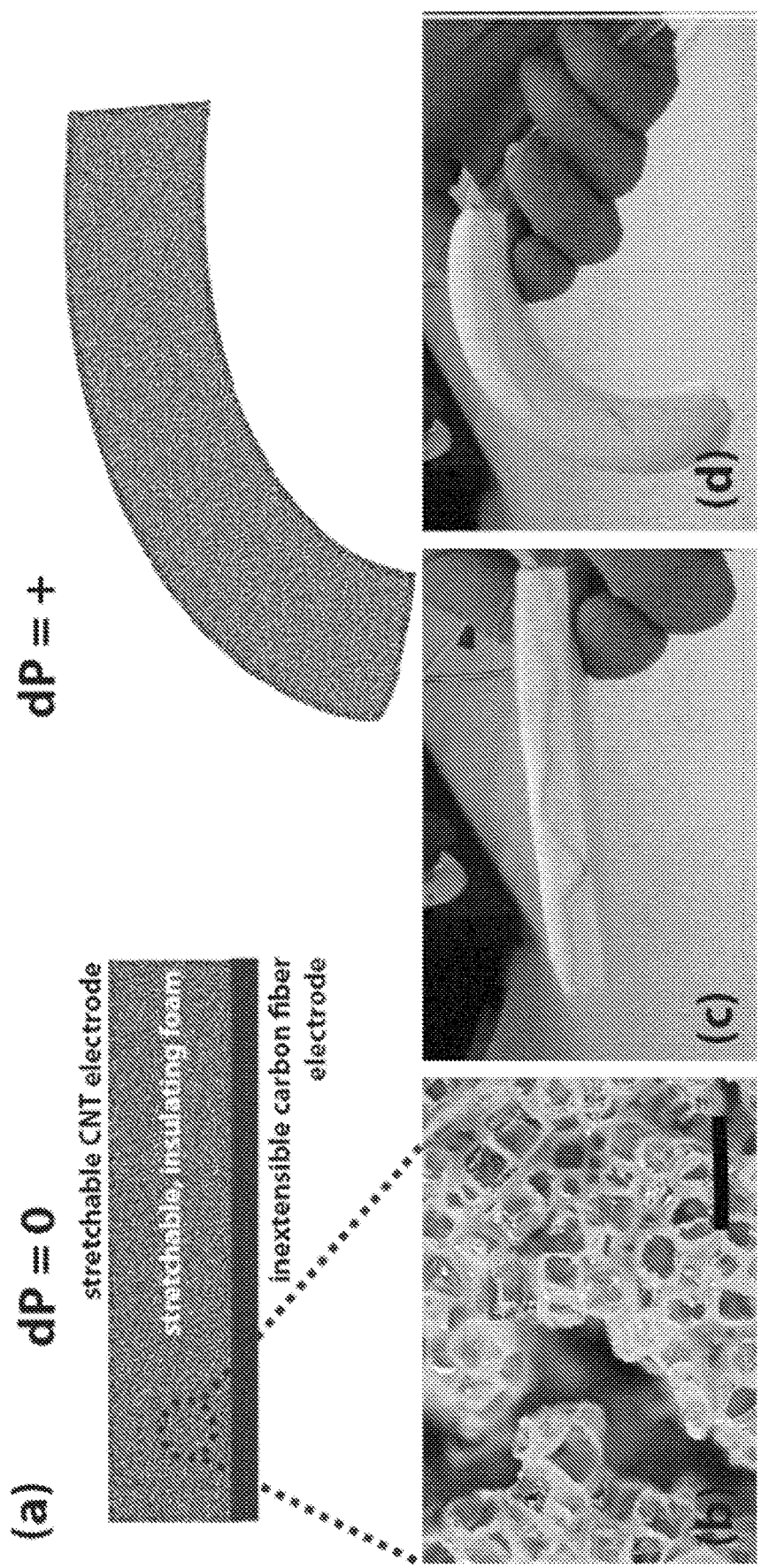
FIG. 27: (a) Schematic representation of elastomer foam not pressurized (left, dP=0 psi) and pressurized (right, dP=20 psi). (b) Microscope image of silicone foam and (c,d) Foam actuator at dP=0 and dP=20 psi.

Poroelastic skins for amphibious thermal management. Actuators (e.g., soft actuators) can be fabricated from elastomeric foams. Such poroelastic actuators can be used as variable thermal insulation skins for amphibious suits. In a particular example, open cell foams may have a continuous network of pores to deliver fluid (e.g., compressed air or liquid) throughout the actuator. FIG. 27 shows a pneumatically actuated foam ("pneu-foam"), pressurized at 20 psi (175 kPa). Because these systems can be injection molded, there is virtually no limitation to their mechanical design. The pneu-foams presented here have less than a third the density, $\rho$~0.2 g $m^{-1}$ of the "pneu-nets" presented in FIGS. 12A and 12B. Because fluidically-powered actuators apply forces in direct proportion to their internal surface area, their specific power may be commensurately higher. Finally, because more material may be stretched per volume in pneu-foams, the actuation amplitudes may be greater for equivalent pressures relative to other soft actuators (e.g., McKibbens or pneu-nets), they may be more energy efficient. By placing stretchable electrodes on either side of the actuators, capacitance changes may be detected for sensing applications. Finally, a vacuum may be pulled or positive pressure applied to expand or collapse the foam network. When the foams are totally collapsed, there may be little or no insulating air and thus an individual, such as, for example, a diver, could operate on land comfortably without changing out of their suit. Upon returning to the cold water, the diver would simply re-inflate the pores air for greater insulation.

Although the present disclosure has been described with respect to one or more particular embodiments, it will be understood that other embodiments of the present disclosure may be made without departing from the spirit and scope of the present disclosure. Hence, the present disclosure is deemed limited only by the appended claims and the reasonable interpretation thereof.

What is claimed is:

1. An electrohydraulic device, comprising:
   a battery having a vessel containing a flowable electrolyte; and
   an actuator in fluidic communication with the vessel of the battery, the actuator configured to be actuated using the flowable electrolyte, and wherein the actuator is a soft actuator configured to be inflated and/or deflated by the flowable electrolyte.

2. The electrohydraulic device of claim 1, wherein the battery is a flow cell battery, and wherein the flowable electrolyte is a catholyte or an anolyte.

3. The electrohydraulic device of claim 1, wherein the battery is a zinc-iodide flow cell battery and the flowable electrolyte is an aqueous catholyte.

4. The electrohydraulic device of claim 1, wherein the flowable electrolyte is a suspension of an active lithium ion compound, a suspension of vanadium (HI) salt, or a suspension of iron (III) salt.

5. The electrohydraulic device of claim 1, wherein the vessel includes a cation exchange membrane separating an anolyte side from a catholyte side, and the actuator is in fluidic communication with the catholyte side of the vessel.

6. The electrohydraulic device of claim 1, wherein the actuator comprises a hydraulic chamber configured to be pressurized by the flowable electrolyte.

7. The electrohydraulic device of claim 1, wherein the soft actuator comprises polyurethane or a styrene-butadiene compound.

8. The electrohydraulic device of claim 1, wherein the actuator makes up at least a portion of the vessel.

9. The electrohydraulic device of claim 1, wherein the actuator is a linear actuator.

10. The electrohydraulic device of claim 1, wherein the actuator comprises an impeller configured to be rotated by a flow of the flowable electrolyte.

11. The electrohydraulic device of claim 1, further comprising a pump for selectively pressurizing or depressurizing the actuator with flowable electrolyte.

12. The electrohydraulic device of claim 1, further comprising a heat exchanger in fluid communication with the battery, wherein the flowable electrolyte is cooled by passage through the heat exchanger.

13. The electrohydraulic device of claim 1, further comprising a sensor configured to detect movement of the actuator.

14. A muscle augmentation system, comprising:
   at least one electrohydraulic device including:
      a battery having a vessel containing a flowable electrolyte; and
      an actuator in fluidic communication with the vessel of the battery, the actuator configured to be actuated using the flowable electrolyte.

15. The muscle augmentation system of claim 14, further comprising a poroelastic skin configured to be selectively expanded or collapsed for thermal management.

16. The muscle augmentation system of claim 14, wherein the actuator is a soft actuator configured to be inflated and/or deflated by the flowable electrolyte.

17. The muscle augmentation system of claim 14, wherein the actuator comprises a linear actuator or an impeller.

* * * * *